United States Patent
Khalili et al.

(10) Patent No.: US 9,925,248 B2
(45) Date of Patent: *Mar. 27, 2018

(54) METHODS AND COMPOSITIONS FOR RNA-GUIDED TREATMENT OF HIV INFECTION

(71) Applicant: TEMPLE UNIVERSITY OF THE COMMONWEALTH SYSTEM OF HIGHER EDUCATION, Philadelphia, PA (US)

(72) Inventors: Kamel Khalili, Bala Cynwyd, PA (US); Wenhui Hu, Cherry Hill, NJ (US)

(73) Assignee: TEMPLE UNIVERSITY OF THE COMMONWEALTH SYSTEM OF HIGHER EDUCATION, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/838,057

(22) PCT Filed: Aug. 29, 2014

(86) PCT No.: PCT/US2014/053441
§ 371 (c)(1),
(2) Date: Dec. 11, 2015

(87) PCT Pub. No.: WO2015/031775
PCT Pub. Date: Mar. 5, 2015

(65) Prior Publication Data
US 2016/0017301 A1    Jan. 21, 2016

Related U.S. Application Data

(60) Provisional application No. 61/871,626, filed on Aug. 29, 2013, provisional application No. 62/026,103, filed on Jul. 18, 2014, provisional application No. 62/018,441, filed on Jun. 27, 2014.

(51) Int. Cl.
| | |
|---|---|
| A61K 48/00 | (2006.01) |
| A61K 38/46 | (2006.01) |
| A61K 9/00 | (2006.01) |
| A61K 35/12 | (2015.01) |
| A61K 45/06 | (2006.01) |
| C12N 7/00 | (2006.01) |
| C12N 9/22 | (2006.01) |
| C12N 15/11 | (2006.01) |
| A61K 39/21 | (2006.01) |
| C12N 15/55 | (2006.01) |
| C12N 15/79 | (2006.01) |
| C12N 15/85 | (2006.01) |
| C12N 15/86 | (2006.01) |

(52) U.S. Cl.
CPC .......... *A61K 38/465* (2013.01); *A61K 9/0034* (2013.01); *A61K 35/12* (2013.01); *A61K 45/06* (2013.01); *A61K 48/00* (2013.01); *A61K 48/005* (2013.01); *C12N 7/00* (2013.01); *C12N 9/22* (2013.01); *C12N 15/111* (2013.01); *C12N 2310/20* (2017.05); *C12N 2320/30* (2013.01); *C12N 2740/16063* (2013.01); *C12Y 301/21* (2013.01)

(58) Field of Classification Search
None
See application file for complete search history.

(56) References Cited

U.S. PATENT DOCUMENTS

| 6,392,029 B1* | 5/2002 | Ludwig ................. C07K 14/005 424/139.1 |
|---|---|---|
| 8,871,516 B2 | 10/2014 | Hauber et al. |
| 8,895,308 B1 | 11/2014 | Zhang et al. |
| 9,023,649 B2 | 5/2015 | Mali et al. |
| 2003/0180756 A1 | 9/2003 | Shi et al. |
| 2004/0132161 A1* | 7/2004 | Finkel .................... A61K 31/00 435/235.1 |

(Continued)

FOREIGN PATENT DOCUMENTS

| WO | WO 97/37005 A1 * | 10/1997 | ............... C12N 5/10 |
|---|---|---|---|
| WO | WO 00/66759 | * 11/2000 | ........... C12N 15/867 |
| WO | WO/2014/165349 | 10/2014 | |

OTHER PUBLICATIONS

Mcintyre et al., "96 shRNAs designed for maximal coverage of HIV-1 variants" 6 Retrovirology 55 1-15 (2009).*

(Continued)

*Primary Examiner* — Nancy J Leith
(74) *Attorney, Agent, or Firm* — Kohn and Associates, PLLC

(57) ABSTRACT

A method of inactivating a proviral DNA integrated into the genome of a host cell latently infected with a retrovirus by treating the host cell with a composition comprising a Clustered Regularly Interspaced Short Palindromic Repeat (CRISPR)-associated endonuclease, and two or more different guide RNAs (gRNAs), wherein each of the at least two gRNAs is complementary to a different target nucleic acid sequence in a long terminal repeat (LTR) in the proviral DNA, and inactivating the proviral DNA. A composition for use in inactivating a proviral DNA integrated into the genome of a host cell latently infected with a retrovirus including isolated nucleic acid sequences comprising a CRISPR-associated endonuclease and a guide RNA, wherein the guide RNA is complementary to a target sequence in a human immunodeficiency virus.

13 Claims, 30 Drawing Sheets
(23 of 30 Drawing Sheet(s) Filed in Color)

(56) References Cited

U.S. PATENT DOCUMENTS

2014/0357530 A1  12/2014  Zhang et al.
2015/0020223 A1   1/2015  Zhang et al.
2016/0040165 A1*  2/2016  Howell ................ C12N 15/111
                                                            514/3.8

OTHER PUBLICATIONS

Hirotaka Ebina, et al., "Harnessing the CRISPR/Cas9 system to disrupt latent HIV-1 provirus." Scientific Reports (Online journal). 3:2510, (2013). DOI: 10.1038/srep02510. Nature Publishing Group.
Ignazio Maggio, et al. "Adenoviral vector delivery of RNA-guided CRISPR/Cas9 nuclease complexes induces targeted mutagenesis in a diverse array of human cells." Scientific Reports (Online journal). 4:5105, (2014). DOI: 10.1038/srep05105. Nature Publishing Group.
N. Manjunath, et al. "Newer Gene Editing Technologies toward HIV Gene Therapy." MDPI (Online journal). Viruses (2013), 5: pp. 2748-2766. Doi: 10.3390/v5112748. Multidisciplinary Digital Publishing Institute.

* cited by examiner

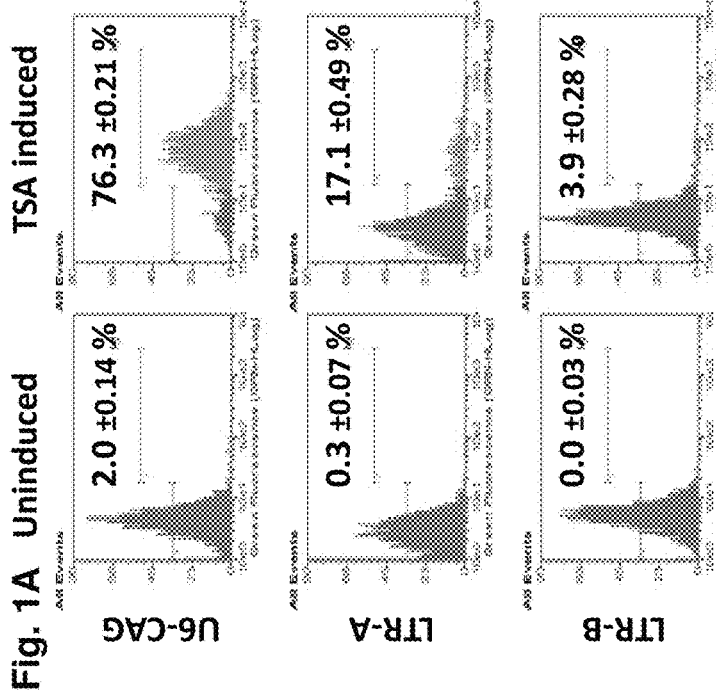

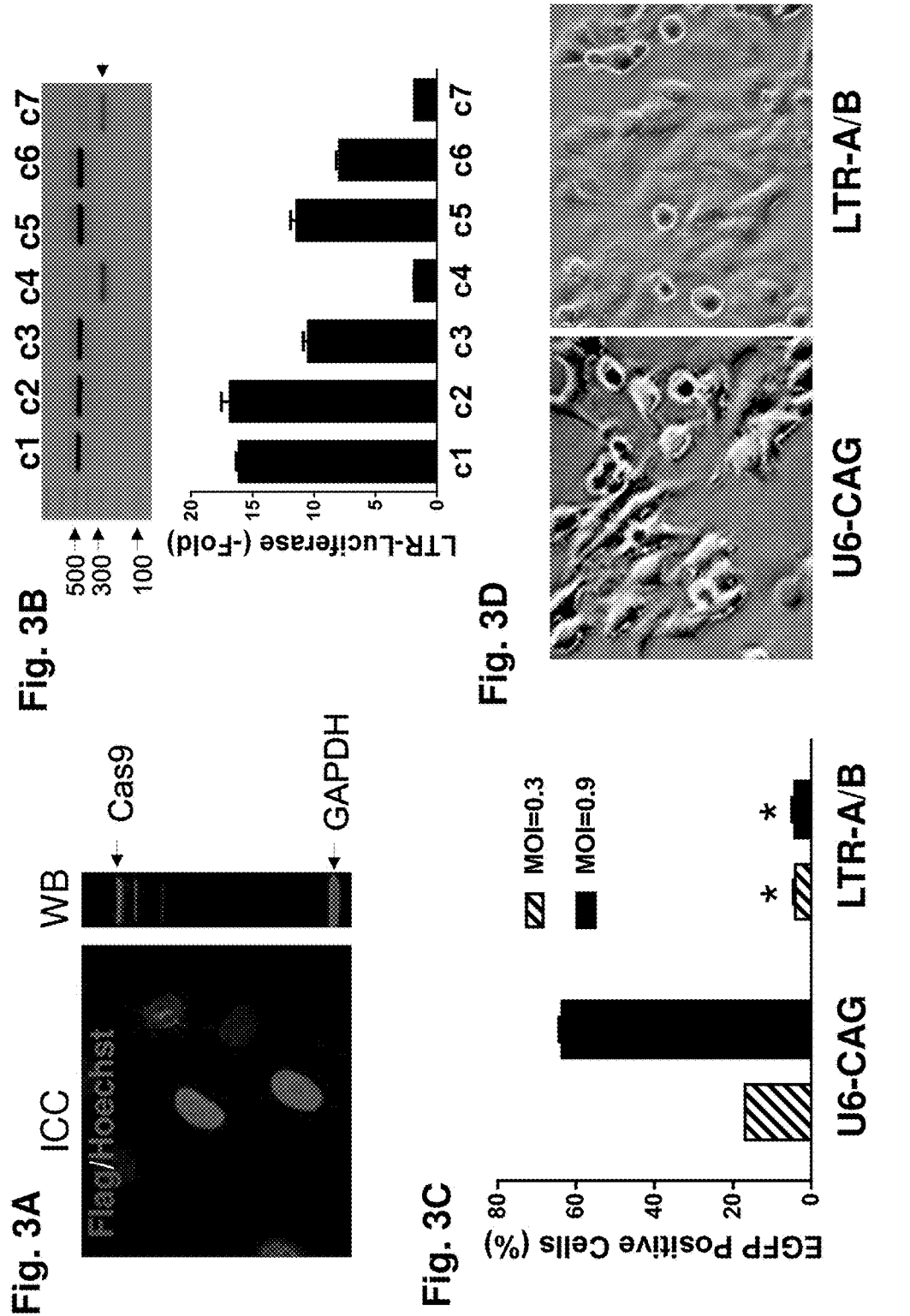

Fig. 4A

| | Off-1 | | Off-5 | | Off-6 | | On-A | |
|---|---|---|---|---|---|---|---|---|
| Cel I | U6 | A/B | U6 | A/B | U6 | A/B | A | U6 |
| TZM-bl | - + | - + | - + | - + | - + | - + | - + | - + |
| U1 | - + | - + | - + | - + | - + | - + | - + | - + |

Fig. 4B

U6-CAG: 159,596
Overlap: 338,904
LTR-A/B: 177,605

Fig. 4D

U6-CAG: 2
Overlap: 6
LTR-A/B: 0

Fig. 4C

| Name | gRNA Target Site | | | | | Indels | | | | | Genotype | |
|---|---|---|---|---|---|---|---|---|---|---|---|---|
| | genome | start | end | strand | genome | start | end | reference | mutation | quality filter | U6-CAG | LTR-A/B |
| LTRA | chr11 | 103532094 | 103532108 | + | chr11 | 1.04E+08 | 103532209 | ATC | A | 272.76 PASS | 1/1 | 1/1 |
| LTRA | chr14 | 241931180 | 241931194 | - | chr14 | 241923852 | 241923875 | GAGATCCGTGTC | G | 86.74 PASS | 0/1 | 0/0 |
| LTRA | chr6 | 989901053 | 989901068 | + | chr6 | 989901264 | 989901267 | CACA | C | 323.75 PASS | 1/1 | 1/1 |
| LTRA | chr6 | 989901053 | 989901068 | - | chr6 | 989901280 | 989901282 | GCA | G | 208.27 PASS | 0/1 | 1/1 |
| LTRA | chr7 | 722110628 | 722110642 | - | chr7 | 722110827 | 722110828 | GT | G | 111.24 LowQual | 0/1 | 0/1 |
| LTRA | chr7 | 722110628 | 722110642 | - | chr7 | 722110829 | 722110832 | GTGT | G | 25.74 PASS | 0/1 | 0/0 |
| LTRA | chr9 | 958871690 | 958871704 | + | chr9 | 958871594 | 958871596 | CCA | C | 456.73 PASS | 0/1 | 0/1 |
| LTRB | HIV | 162 | 184 | + | HIV | 371 | 375 | GTAGA | C | 14.87 LowQual | 0/0 | 0/1 |
| LTRB | chr15 | 82132445 | 82132459 | + | chr15 | 82132704 | 82132704 | T | TTGTG, TTGTGTGTG | 109.78 PASS | 1/1 | 1/1 |
| LTRB | HIV | 9291 | 9313 | - | HIV | 9616 | 9616 | A | A...... | 174.06 PASS | 0/0 | 0/1 | nt 1-22 of SEQ ID NO:14

SEQ ID NO:15

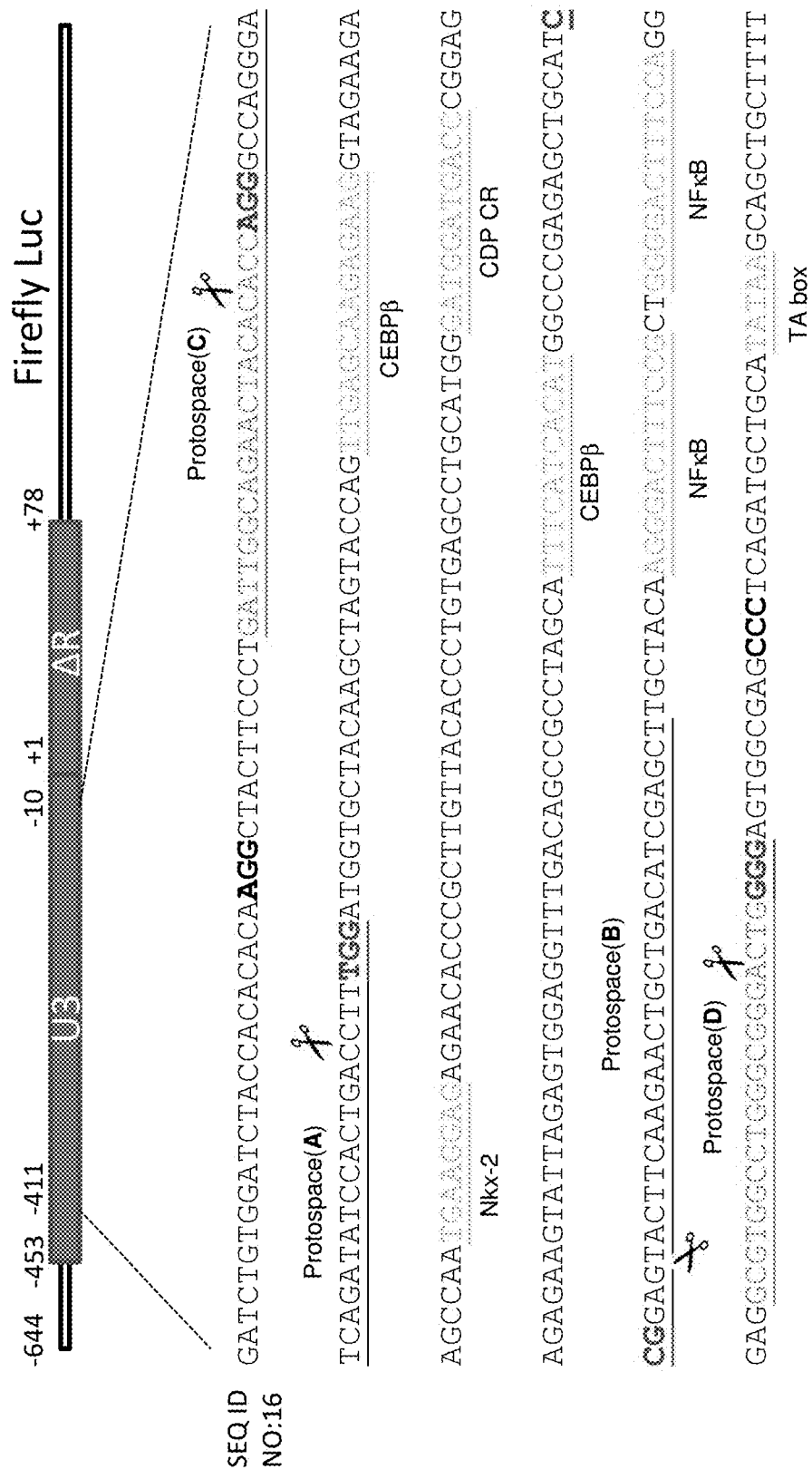

Fig. 7D

```
SEQ ID NO:26  WT     GACTTTCCAGGGAGGCGTGGCCTGGGCGGGACTGGGGAGTGCCAGATGTGCTATATAAGCAGCTGCTTTTTGCCTGTGAAGCCGAATTC
SEQ ID NO:27  A (q)  GACTTTCCAGGGAGGCGTGGCCTGGGCGGG--A--CTGGGGAGTGCCAGATGTGCTATATAAGCAGCTGCTTTTTGCCTGTGAAGCCGAATTC
SEQ ID NO:28  +2     GACTTTCCAGGGAGGCGTGGCCTGGGCGGGTACTGGGGAGTGCCAGATGTGCTATATAAGCAGCTGCTTTTTGCCTGTGAAGCCGAATTC
SEQ ID NO:29  -1     GACTTTCCAGGGAGGCGTGGCCTGGGCGGG--A--CTGGGGAGTGCCAGATGTGCATA-AAGCAGCTGCTTTTTGCCTGTGAAGCCGAATTC
SEQ ID NO:30  -63    GACTTTCCAGG-----------------------------------------------------------------------GAAGCCGAATTC
```

13% (4/30) mutated (LTR-D) in TZMbl cells

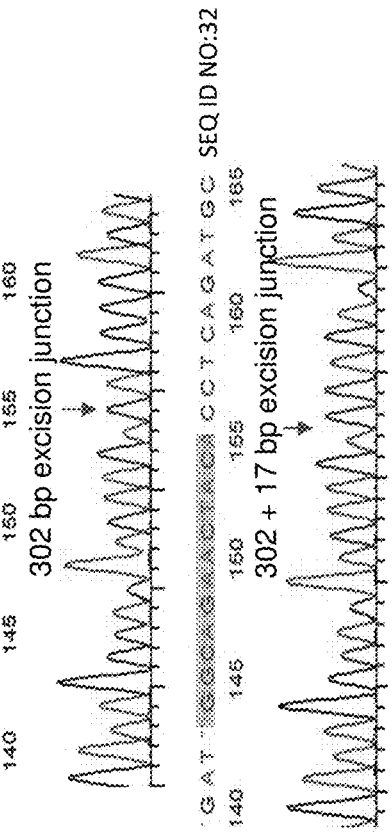

Fig. 7F

302 bp excision junction

302 + 17 bp excision junction

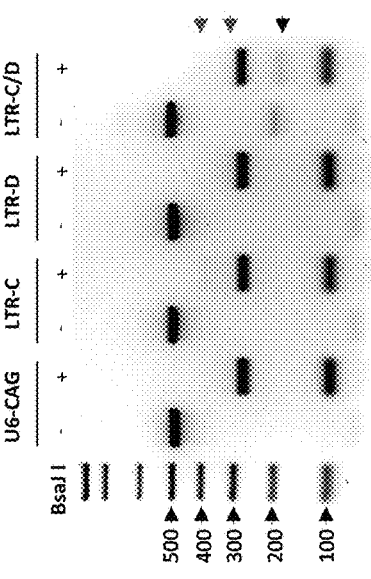

Fig. 7E

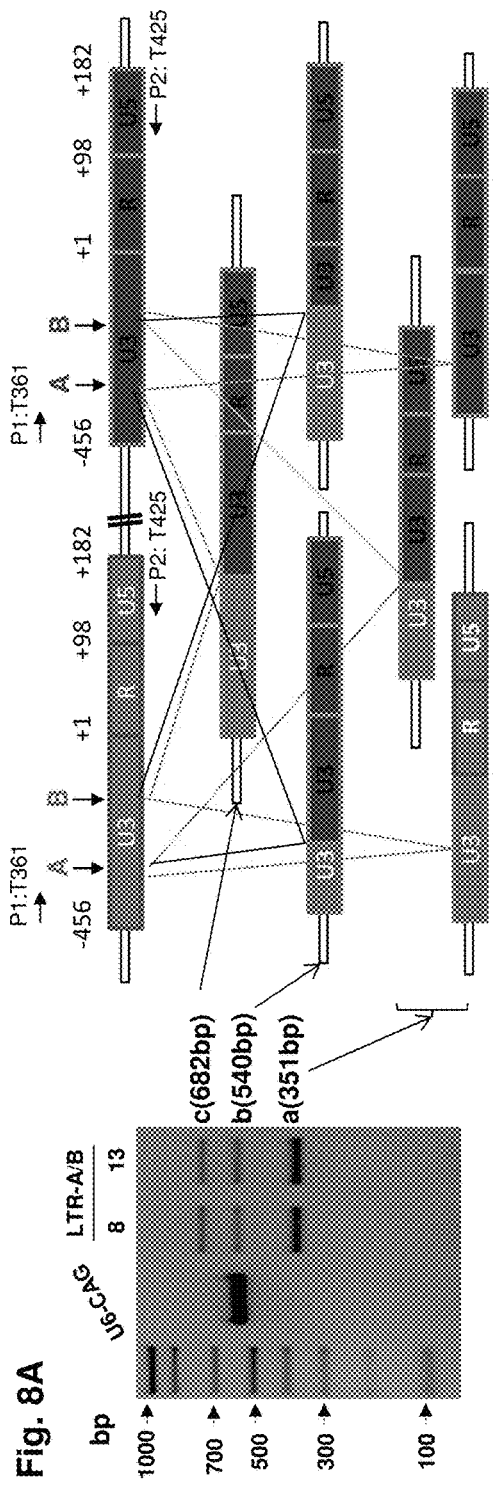
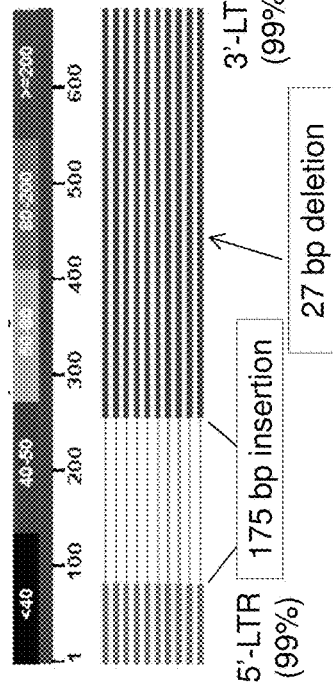
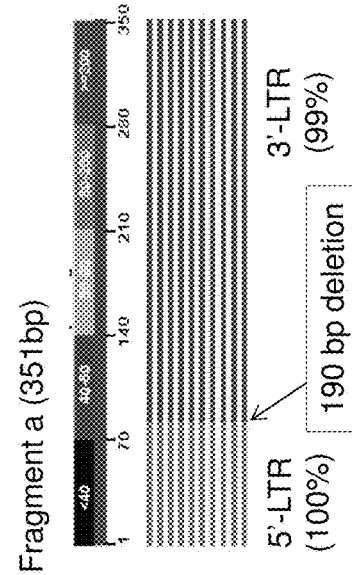
Fig. 8A
Fig. 8B Fragment a (351bp)
Fig. 8C Fragment c(682bp)

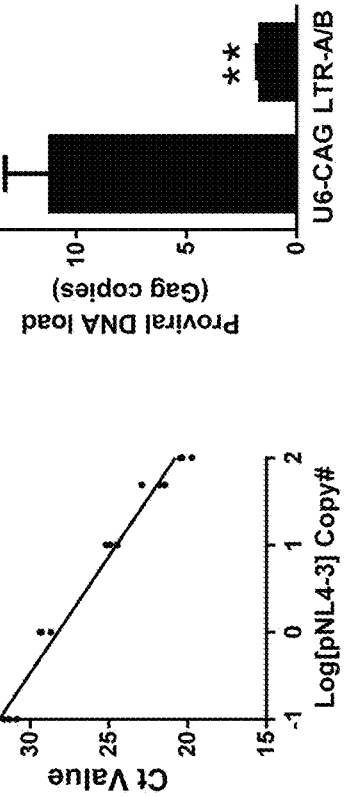
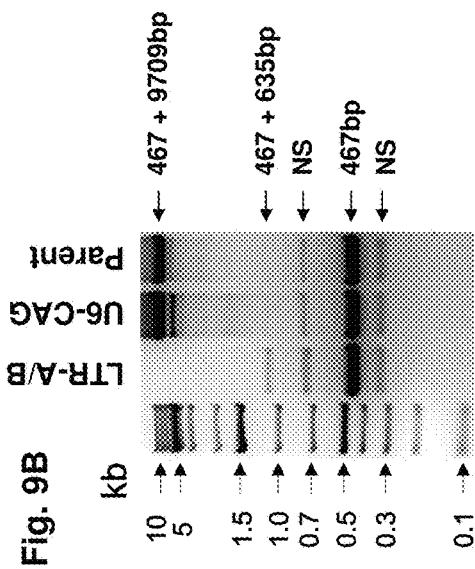
Fig. 9A, Fig. 9B, Fig. 9C, Fig. 9D

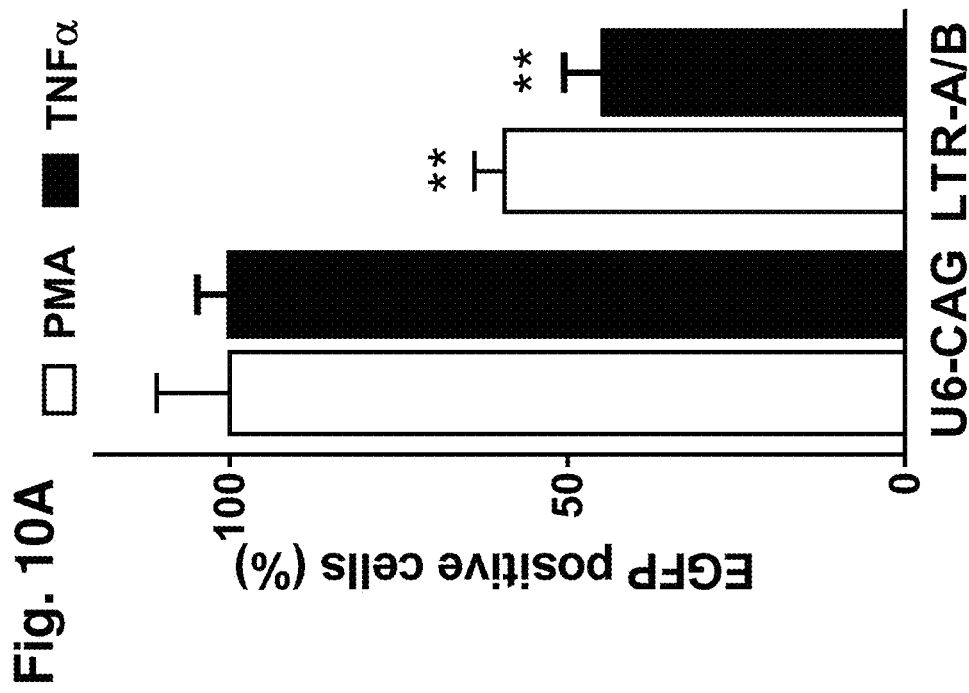

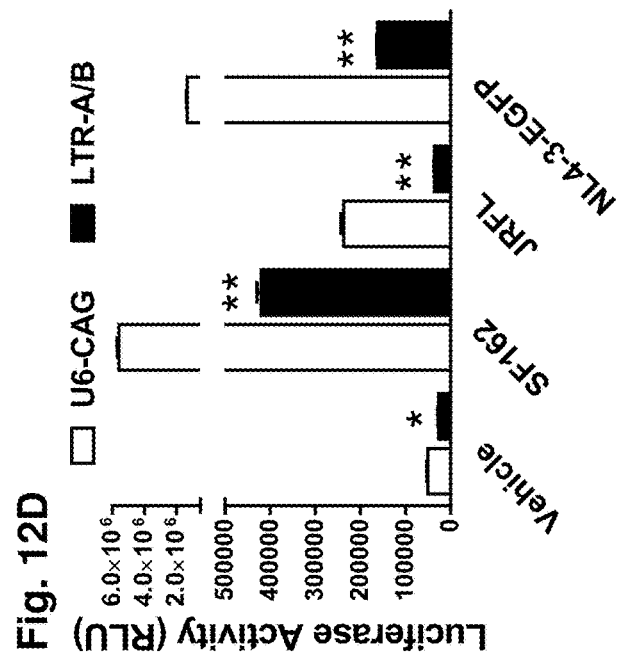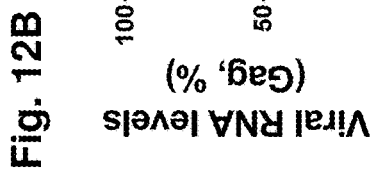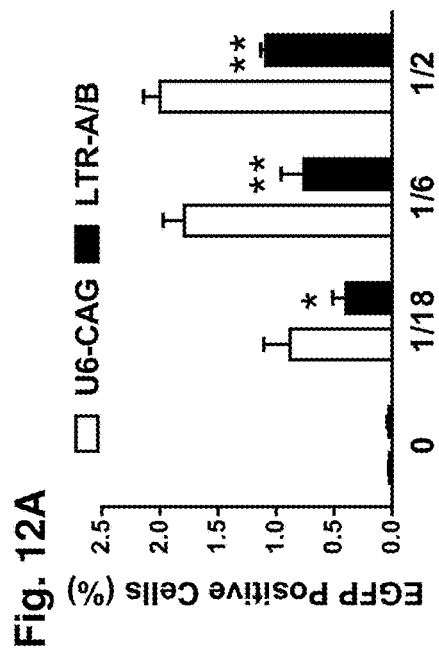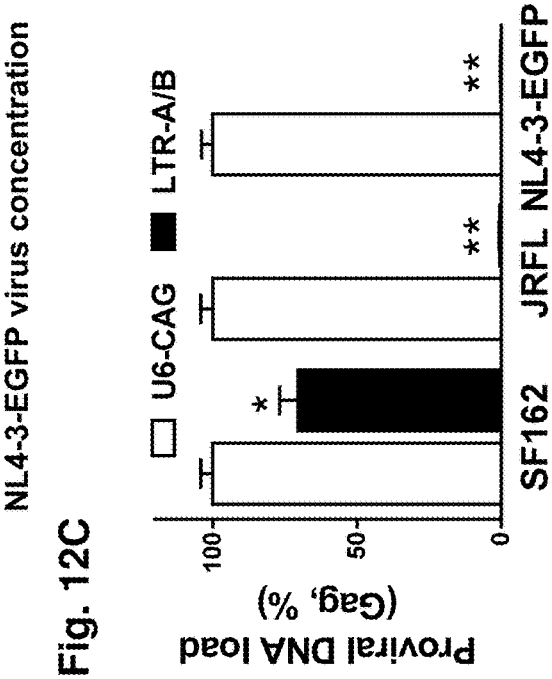

Fig. 13 Predicted LTR gRNAs and their off-target numbers (100% match)

| Name | No. | gRNA sequence (Sense) | 20 | 19 | 18 | 17 | 16 | 15 | 14 | 13 | 12 |
|---|---|---|---|---|---|---|---|---|---|---|---|
| SEQ ID NO: 79 | 1 | TCAAGACCCTTTAGTCAGTGTGG | 0 | 0 | 0 | 0 | 0 | 0 | 0 | 2 | 25 |
| SEQ ID NO: 80 | 2 | TTGCTTGTACTGGGTCTCTTGG | 0 | 0 | 0 | 0 | 0 | 0 | 0 | 3 | 10 |
| SEQ ID NO: 81 | 3 | CAGTTGCTTTTTGCTTGTACTGG | 0 | 0 | 0 | 0 | 0 | 0 | 2 | 4 | 11 |
| SEQ ID NO: 82 | 4 | CTTGACATTGCAGCTTGCTACAAGG | 0 | 0 | 0 | 0 | 0 | 0 | 0 | 0 | 17 |
| SEQ ID NO: 83 | 5 | CCGCTAGCATTTATCACATGG | 0 | 0 | 0 | 0 | 0 | 1 | 2 | 9 | 55 |
| SEQ ID NO: 84 | 6 | CCGAGACAGAAGTATTAGAGTGG | 0 | 0 | 0 | 0 | 0 | 0 | 0 | 3 | 18 |
| SEQ ID NO: 85 | 7 | AGTACCAGTTGACCAAGAGAAGG | 0 | 0 | 0 | 0 | 0 | 0 | 0 | 1 | 18 |
| SEQ ID NO: 86 | 8 | GATATTCACTGACTTTGGATGG | 0 | 0 | 0 | 0 | 0 | 1 | 3 | 22 | 211 |
| SEQ ID NO: 87 LTR-C | 9 | ■■■■■■■■■■■■■■■■■■■ | ■ | ■ | ■ | ■ | ■ | ■ | ■ | ■ | ■ |
| SEQ ID NO: 88 | 10 | CACAAGGCTACTTCCCTGATTGG | 0 | 0 | 0 | 0 | 0 | 0 | 0 | 2 | 11 |
| SEQ ID NO: 89 | 11 | CTGTGGATCTACCACACAAGG | 0 | 0 | 0 | 0 | 0 | 2 | 5 | 12 | 37 |
| SEQ ID NO: 90 | 12 | TGGGAGCTTCTCTGGCTAACTAGG | 0 | 0 | 0 | 0 | 0 | 0 | 0 | 4 | 14 |
| SEQ ID NO: 91 | 13 | GGTTAGACCAGATCTGACCTTGG | 0 | 0 | 0 | 0 | 0 | 0 | 0 | 9 | 33 |
| SEQ ID NO: 92 | 14 | TGCTACAAGGGACTTTTCCGTGG | 0 | 0 | 0 | 0 | 0 | 0 | 0 | 2 | 5 |
| SEQ ID NO: 93 | 15 | AGAGAAGAAGTATTAGAGTGAAGG | 0 | 0 | 0 | 0 | 0 | 0 | 5 | 7 | 16 |
| SEQ ID NO: 94 | 16 | TTACACCCTGTGAGCCTGCATGG | 0 | 0 | 0 | 0 | 0 | 0 | 3 | 14 | 35 |
| SEQ ID NO: 95 | 17 | AAGGTAGAAGAAGCCAATGAAGG | 0 | 0 | 0 | 0 | 0 | 0 | 4 | 36 | 75 |
| SEQ ID NO: 96 LTR-A | 18 | ■■■■■■■■■■■■■■■■■■■ | ■ | ■ | ■ | ■ | ■ | ■ | ■ | ■ | ■ |
| SEQ ID NO: 97 | 19 | GACAAGATATCCTTGATCTGTGG | 0 | 0 | 0 | 0 | 0 | 0 | 0 | 0 | 10 |
| SEQ ID NO: 98 | 20 | GCCGGTCTGTGTGTGACTCTGG | 0 | 0 | 0 | 0 | 0 | 0 | 3 | 7 | 35 |
| SEQ ID NO: 99 | 21 | ATCTGAGCCTGGGAGCTCTTGG | 0 | 0 | 0 | 0 | 1 | 2 | 9 | 32 | 78 |
| SEQ ID NO: 100 | 22 | CTTTCCGCTGGGGACTTTCCAGG | 0 | 0 | 0 | 0 | 0 | 0 | 0 | 0 | 4 |
| SEQ ID NO: 101 | 23 | CAGAACTACACACAGGGCCAGG | 0 | 0 | 0 | 0 | 0 | 0 | 0 | 3 | 20 |
| SEQ ID NO: 102 | 24 | CCTTGCATGGGATGGATGACCCGG | 0 | 0 | 0 | 0 | 2 | 2 | 2 | 5 | 21 |

Fig. 13 cont'd.

| Name | No. | gRNA sequence | 20 | 19 | 18 | 17 | 16 | 15 | 14 | 13 | 12 |
|---|---|---|---|---|---|---|---|---|---|---|---|
| | | Sense | | | | | | | | | |
| SEQ ID NO: 103 | 25 | CCCTGTGAGCCTGCATGGATGG | 0 | 0 | 0 | 0 | 1 | 1 | 2 | 9 | 30 |
| SEQ ID NO: 104 | 26 | CTTTCCAGGGAGGCGTGGCCTGG | 0 | 0 | 0 | 0 | 0 | 8 | 15 | 32 | 75 |
| SEQ ID NO: 105 | 27 | GGGGACTTTCCAGGAGGCGTGG | 0 | 0 | 0 | 0 | 0 | 0 | 0 | 5 | 24 |
| SEQ ID NO: 106 | 28 | CCGCTGGGACTTTCCAGGGAGG | 0 | 0 | 0 | 0 | 0 | 1 | 3 | 9 | 25 |
| SEQ ID NO: 107 | 29 | CATGGCCGAGAGCTGCATCGG | 0 | 0 | 0 | 0 | 1 | 2 | 0 | 0 | 16 |
| SEQ ID NO: 108 | 30 | GCCTGTGGGCGGGACTGGGAGTGG | 0 | 0 | 0 | 0 | 0 | 0 | 7 | 18 | 250 |
| SEQ ID NO: 109 | 31 | AGGCGTGGCCTGGGCTGGACTGG | ■ | ■ | ■ | ■ | ■ | ■ | ■ | 2 | 6 |
| SEQ ID NO: 110 LTR-D | 32 | | | | | | | | | | |
| SEQ ID NO: 111 | 33 | CCAGGGAGGCGTGGCCTGGGCGG | 0 | 0 | 0 | 0 | 2 | 2 | 2 | 11 | 22 |
| | | Antisense | | | | | | | | | |
| SEQ ID NO: 112 | 1 | TGTGGTAGATTCACAGATCAAGG | 0 | 0 | 0 | 0 | 0 | 0 | 0 | 3 | 13 |
| SEQ ID NO: 113 | 2 | GTGTGTAGTTCTGCCAATCAGG | 0 | 0 | 0 | 0 | 0 | 0 | 0 | 8 | 11 |
| SEQ ID NO: 114 | 3 | GTCAGTGGATATTGATCCCTGG | 0 | 0 | 0 | 0 | 0 | 0 | 2 | 2 | 10 |
| SEQ ID NO: 115 | 4 | TAGCACCCATCCAAAGGTCACTGG | 0 | 0 | 0 | 0 | 0 | 0 | 2 | 3 | 10 |
| SEQ ID NO: 116 | 5 | TAGCTTGTAGCACCATCCAAAGG | 0 | 0 | 0 | 0 | 0 | 1 | 1 | 6 | 12 |
| SEQ ID NO: 117 | 6 | TCTACCTTCTTGCTCAACTGG | 0 | 0 | 0 | 0 | 0 | 0 | 1 | 1 | 6 |
| SEQ ID NO: 118 | 7 | CACTCTAATACTTCTCTGG | 0 | 0 | 0 | 0 | 0 | 1 | 0 | 1 | 26 |
| SEQ ID NO: 119 | 8 | CCATGTGATGAAATGCTAGCCGG | 0 | 0 | 0 | 0 | 0 | 0 | 1 | 5 | 17 |
| SEQ ID NO: 120 | 9 | GGGCCATGCATGAAATGCTAGG | ■ | ■ | ■ | ■ | ■ | ■ | ■ | 3 | 48 |
| SEQ ID NO: 121 LTR-B | 10 | | | | | | | | | | |
| SEQ ID NO: 122 | 11 | CTGCTTATATGCAGCATCTGAGG | 0 | 0 | 0 | 0 | 0 | 0 | 0 | 4 | 39 |
| SEQ ID NO: 123 | 12 | CACACTACTTGAAGCACTCAAGG | 0 | 0 | 0 | 0 | 0 | 0 | 0 | 3 | 19 |
| SEQ ID NO: 124 | 13 | TACCAGAGTCACACACAGACGG | 0 | 0 | 0 | 0 | 0 | 0 | 0 | 2 | 12 |

Fig. 13 cont'd.

| Name | No. | gRNA sequence | 20 | 19 | 18 | 17 | 16 | 15 | 14 | 13 | 12 |
|---|---|---|---|---|---|---|---|---|---|---|---|
| | | Antisense | | | | | | | | | |
| SEQ ID NO: 125 | 14 | ACACTGACTAAAAGGGTCTGAGG | 0 | 0 | 0 | 0 | 1 | 2 | 3 | 4 | 15 |
| SEQ ID NO: 126 | 15 | CAAGGATATCTTGTCTTCGTTGG | 0 | 0 | 0 | 0 | 0 | 0 | 0 | 1 | 5 |
| SEQ ID NO: 127 | 16 | CAGGGAAGTAGCCTTGTGTGTGG | 0 | 0 | 0 | 0 | 0 | 1 | 2 | 4 | 17 |
| SEQ ID NO: 128 | 17 | GCGGTGTTCTCTCCTTCATTGG | 0 | 0 | 0 | 0 | 0 | 2 | 2 | 15 | 49 |
| SEQ ID NO: 129 | 18 | TAGTTAGCCAGAGAGTCCCAGG | 0 | 0 | 0 | 0 | 0 | 2 | 4 | 24 | 93 |
| SEQ ID NO: 130 | 19 | CTTTATTGAGGCTTAAGCAGTGG | 0 | 0 | 0 | 0 | 0 | 0 | 0 | 4 | 25 |
| SEQ ID NO: 131 | 20 | ACTCAAGGCAAGTTTATTGAGG | 0 | 0 | 0 | 0 | 0 | 1 | 0 | 1 | 28 |
| SEQ ID NO: 132 | 21 | GGATATCTGATCCCTGGCCCTGG | 0 | 0 | 0 | 0 | 0 | 0 | 2 | 8 | 43 |
| SEQ ID NO: 133 | 22 | GGCTCACAGGGTGTAACAAGCGG | 0 | 0 | 0 | 0 | 0 | 0 | 0 | 2 | 5 |
| SEQ ID NO: 134 | 23 | TCCATCCCATGCAGGCTCACAGG | 0 | 0 | 0 | 0 | 0 | 3 | 3 | 8 | 20 |
| SEQ ID NO: 135 | 24 | AGTACTCCGGATGCAGCTCTCGG | 0 | 0 | 0 | 0 | 0 | 0 | 1 | 5 | 48 |
| SEQ ID NO: 136 | 25 | AGAGCTCCCAGGCTCAGATCTGG | 0 | 0 | 0 | 0 | 0 | 0 | 4 | 15 | 38 |
| SEQ ID NO: 137 | 26 | GATTTTCCACACTGACTAAAAGG | 0 | 0 | 0 | 0 | 0 | 0 | 0 | 8 | 21 |
| SEQ ID NO: 138 | 27 | CCGGGTCATCCATCCATGCAGG | 0 | 0 | 0 | 0 | 0 | 0 | 0 | 4 | 36 |
| SEQ ID NO: 139 | 28 | CCTCCCTGGAAAGTCCCAGCGG | 0 | 0 | 0 | 0 | 0 | 0 | 3 | 14 | 37 |
| SEQ ID NO: 140 | 29 | GCCACTCCCAGTCCGCCCAGG | 0 | 0 | 0 | 0 | 0 | 0 | 1 | 4 | 14 |
| SEQ ID NO: 141 | 30 | CCGCCCAGGCCACGGCTCCTGG | 0 | 0 | 0 | 0 | 0 | 1 | 1 | 6 | 19 |

Fig. 14

| Target name | Direction | Sequences (5' to 3') | SEQ ID NOS. |
|---|---|---|---|
| LTR-A | T353: Sense | aaaaAGGGCCAGGGATCAGATATCCACTGACCTTgt | SEQ ID NO: 36 |
|  | T354: Antisense | taaaaAAGGTCAGTGGATATCTGATCCCTGGCCCT | SEQ ID NO: 37 |
| LTR-B | T355: Anti-sense | aaaaAGCTCGATGTCAGCAGTTCTTGAAGTACTCgt | SEQ ID NO: 38 |
|  | T356: Sense | taaaaGAGTACTTCAAGAACTGCTGACATCGAGCT | SEQ ID NO: 39 |
| LTR-C | T357: Sense | caccGATTGGCAGAACTACACACC | SEQ ID NO: 40 |
|  | T358: Antisense | aaaaGGTGTGTAGTTCTGCCAATC | SEQ ID NO: 41 |
| LTR-D | T359: Sense | aaaaGCGTGGCCTGGGCGGGACTG | SEQ ID NO: 42 |
|  | T360: Antisense | aaaaCAGTCCCGCCCAGGCCACGC | SEQ ID NO: 43 |
| PCR primer | | | |
| LTR -453/F | Sense | TGGAAGGGCTAATTCACTCCCAAC | SEQ ID NO: 44 |
| LTR +43/R | Anti-sense | CCGAGAGCTCCCAGGCTCAGATCT | SEQ ID NO: 45 |
| LTR -411/F | T361: Sense | caccGATCTGTGGATCTACCACACA | SEQ ID NO: 46 |
| LTR +129/R | T363: Anti-sense | aaaaGAGTCACACAACAGACGGGC | SEQ ID NO: 47 |
| Cas-hU6/5'/XhoBm | T351: Sense | cgcctcgaggatccGAGGGCCTATTCCCATGATTCC | SEQ ID NO: 48 |
| Cas-CAG/3'/EcoR | T352: Anti-sense | tgtgaattcAGGCGGCCATTACCGTAAGTTATG | SEQ ID NO: 49 |
| U1-Chromosome X | T485: Sense | ACGACTATCTTATCAATCCTTCCTG | SEQ ID NO: 50 |
|  | T486: Anti-sense | CTAGGTGATTAGGATATTCTACAATC | SEQ ID NO: 51 |
| U1-Chromosome 2 | T492: Sense | GCTATTGTATCTGATCACAAGCTG | SEQ ID NO: 52 |
|  | T493: Anti-sense | TTGATTGTGTGTCCAGGTCCTAGG | SEQ ID NO: 53 |
| d2EGFP | T494: Sense | GCAAGGGCGAGGAGCTGTTCACC | SEQ ID NO: 54 |
|  | T495: Anti-sense | TTGTAGTTGCCGTCGTCCTTGAAG | SEQ ID NO: 55 |
| Gag | T457: Sense | AATGGTACATCAGGCCATATCAC | SEQ ID NO: 56 |
|  | T458: Anti-sense | CCCACTGTGTTTAGCATGGTATT | SEQ ID NO: 57 |
| Cas9 | T477: Sense | CACAGCATCAAGAAGAAACCTGAT | SEQ ID NO: 58 |
|  | T491: Anti-sense | TCTTCCGTCTGGTGTATCTTCTTC | SEQ ID NO: 59 |
| RRE | Sense | CGCCAAGCTTGAATAGGAGCTTTGTTCC | SEQ ID NO: 60 |
|  | Antisense | CTAGGATCCAGGAGCTGTTGATCCTTTAGG | SEQ ID NO: 61 |

Fig. 14 cont'd.

| Target name Off-Target (OT) | Direction | Sequences (5' to 3') | SEQ ID NOS. |
|---|---|---|---|
| LTR-A-OT-1 | T465: Sense | GTGGACTTTGGATGGTGAGATAG | SEQ ID NO: 62 |
| | T466: Anti-sense | GCCTGGCAAGAGTGAACTGAGTC | SEQ ID NO: 63 |
| LTR-A-OT-2 | T467: Sense | AAGATAATGAGTTGTGGCAGAGC | SEQ ID NO: 64 |
| | T468: Anti-sense | TCTACCTGGTAATCCAGCATCTGG | SEQ ID NO: 65 |
| LTR-A-OT-3 | T469: Sense | ATAGGAGGAAGGCACCAAGAGGG | SEQ ID NO: 66 |
| | T470: Anti-sense | AATGATGCTTTGGTCCTACTCCT | SEQ ID NO: 67 |
| LTR-A-OT-4 | T471: Sense | TGCTCTTGCTACTCTGGCATGTAC | SEQ ID NO: 68 |
| | T472: Anti-sense | AATCTACCTCTGAGAGCTGCAGG | SEQ ID NO: 69 |
| LTR-A-OT-5 | T473: Sense | TCAGACACAGCTGAAGCAGAGGC | SEQ ID NO: 70 |
| | T474: Anti-sense | ATGCCAGTGTCAGTAGATGTCAG | SEQ ID NO: 71 |
| LTR-A-OT-6 | T475: Sense | TCAAGATCAGCCAGAGTGCACATG | SEQ ID NO: 72 |
| | T476: Anti-sense | TGCTCTTCCGAGCCTCTCTGAG | SEQ ID NO: 73 |
| Others | | | |
| hU6-sequence | T428: Sense | ATGGACTATCATATGCTTACCG | SEQ ID NO: 74 |
| LSP1 | Sense | GCTTCAGCAAGCCGAGTCCTGCGTCGAG | SEQ ID NO: 75 |
| LSP2 | Anti-sense | GCTCCTCTGGTTTCCCTTTCGCTTTCAA | SEQ ID NO: 76 |
| AP1 | Sense | GTAATACGACTCACTATAGGGC | SEQ ID NO: 77 |
| AP2 | Anti-sense | ACTATAGGGCACGCGTGGT | SEQ ID NO: 78 |

Fig. 15

| name | query Seq | SEQ ID NO: | Subj. ID | Identity (%) | E-Value | start | end | strand | ref Seq | SEQ ID NO: | mismatch (12bp seed) |
|---|---|---|---|---|---|---|---|---|---|---|---|
| LTRA | ATCAGATATCCACTGACCTTTGG | 142 | HIV | 100 | 7.00E-04 | 162 | 184 | + | ATCAGATATCCACTGACCTTTGG | 253 | 0 |
| LTRA | TCAGATATCCACTGACCTTTGG | 143 | HIV | 100 | 0.003 | 163 | 184 | + | TCAGATATCCACTGACCTTTGG | 254 | 0 |
| LTRA | TCAGATATCCACTGACCTTTGG | 144 | HIV | 100 | 0.003 | 9091 | 9112 | + | TCAGATATCCACTGACCTTTGG | 255 | 0 |
| LTRA | CAGATATCCACTGACCTTTGG | 145 | HIV | 100 | 0.009 | 164 | 184 | + | CAGATATCCACTGACCTTTGG | 256 | 0 |
| LTRA | CAGATATCCACTGACCTTTGG | 146 | HIV | 100 | 0.009 | 9092 | 9112 | + | CAGATATCCACTGACCTTTGG | 257 | 0 |
| LTRA | AGATATCCACTGACCTTTGG | 147 | HIV | 100 | 0.033 | 165 | 184 | + | AGATATCCACTGACCTTTGG | 258 | 0 |
| LTRA | AGATATCCACTGACCTTTGG | 148 | HIV | 100 | 0.033 | 9093 | 9112 | + | AGATATCCACTGACCTTTGG | 259 | 0 |
| LTRA | GATATCCACTGACCTTTGG | 149 | HIV | 100 | 0.12 | 166 | 184 | + | GATATCCACTGACCTTTGG | 260 | 0 |
| LTRA | GATATCCACTGACCTTTGG | 150 | HIV | 100 | 0.12 | 9094 | 9112 | + | GATATCCACTGACCTTTGG | 261 | 0 |
| LTRA | ATATCCACTGACCTTTGG | 151 | HIV | 100 | 0.42 | 167 | 184 | + | ATATCCACTGACCTTTGG | 262 | 0 |
| LTRA | ATATCCACTGACCTTTGG | 152 | HIV | 100 | 0.42 | 9095 | 9112 | + | ATATCCACTGACCTTTGG | 263 | 0 |
| LTRA | TATCCACTGACCTTGGG | 153 | chr5 | 100 | 1.5 | 21926317 | 21926333 | + | TATCCACTGACCTTGGG | 264 | 0 |
| LTRA | TATCCACTGACCTTTGG | 154 | HIV | 100 | 1.5 | 168 | 184 | + | TATCCACTGACCTTTGG | 265 | 0 |
| LTRA | TATCCACTGACCTTTGG | 155 | HIV | 100 | 1.5 | 9096 | 9112 | + | TATCCACTGACCTTTGG | 266 | 0 |
| LTRA | TATCCACTGACCTTAAG | 156 | chr3 | 100 | 1.5 | 116712577 | 116712593 | + | TATCCACTGACCTTAAG | 267 | 0 |
| LTRA | TATCCACTGACCTTGAG | 157 | chr6 | 100 | 1.5 | 32460607 | 32460623 | + | TATCCACTGACCTTGAG | 268 | 0 |
| LTRA | ATCCACTGACCTTAGG | 158 | chr3 | 100 | 5.4 | 2669092 | 2669107 | + | ATCCACTGACCTTAGG | 269 | 0 |
| LTRA | ATCCACTGACCTTAGG | 159 | chr3 | 100 | 5.4 | 158293369 | 158293384 | + | ATCCACTGACCTTAGG | 270 | 0 |
| LTRA | ATCCACTGACCTTGGG | 160 | chr20 | 100 | 5.4 | 46918344 | 46918359 | + | ATCCACTGACCTTGGG | 271 | 0 |
| LTRA | ATCCACTGACCTTGGG | 161 | chr14 | 100 | 5.4 | 86310067 | 86310082 | − | ATCCACTGACCTTGGG | 272 | 0 |
| LTRA | ATCCACTGACCTTGGG | 162 | chr5 | 100 | 5.4 | 21926318 | 21926333 | + | ATCCACTGACCTTGGG | 273 | 0 |
| LTRA | ATCCACTGACCTTGGG | 163 | chr4 | 100 | 5.4 | 95491921 | 95491936 | − | ATCCACTGACCTTGGG | 274 | 0 |
| LTRA | ATCCACTGACCTTTGG | 164 | HIV | 100 | 5.4 | 169 | 184 | + | ATCCACTGACCTTTGG | 275 | 0 |
| LTRA | ATCCACTGACCTTTGG | 165 | HIV | 100 | 5.4 | 9097 | 9112 | + | ATCCACTGACCTTTGG | 276 | 0 |
| LTRA | ATCCACTGACCTTTGG | 166 | chr6 | 100 | 5.4 | 98901053 | 98901068 | + | ATCCACTGACCTTTGG | 277 | 0 |
| LTRA | ATCCACTGACCTTAAG | 167 | chr7 | 100 | 5.4 | 155511293 | 155511308 | − | ATCCACTGACCTTAAG | 278 | 0 |
| LTRA | ATCCACTGACCTTAAG | 168 | chr3 | 100 | 5.4 | 116712578 | 116712593 | + | ATCCACTGACCTTAAG | 279 | 0 |
| LTRA | ATCCACTGACCTTCAG | 169 | chr5 | 100 | 5.4 | 152371289 | 152371304 | + | ATCCACTGACCTTCAG | 280 | 0 |

Fig. 15, cont'd.

| name | query Seq | SEQ ID NO: | Subj. ID | Identity (%) | E-Value | start | end | strand | ref Seq | SEQ ID NO: | mismatch (12bp seed) |
|---|---|---|---|---|---|---|---|---|---|---|---|
| LTRA | ATCCACTGACCTTCAG | 170 | chr4 | 100 | 5.4 | 110823169 | 110823184 | − | ATCCACTGACCTTCAG | 281 | 0 |
| LTRA | ATCCACTGACCTTGAG | 171 | chrX | 100 | 5.4 | 74260260 | 74260275 | + | ATCCACTGACCTTGAG | 282 | 0 |
| LTRA | ATCCACTGACCTTGAG | 172 | chr6 | 100 | 5.4 | 32460608 | 32460623 | + | ATCCACTGACCTTGAG | 283 | 0 |
| LTRA | ATCCACTGACCTTGAG | 173 | chr12 | 100 | 20 | 14485012 | 14485026 | − | TCCACTGACCTTAGG | 284 | 0 |
| LTRA | TCCACTGACCTTAGG | 174 | chr7 | 100 | 20 | 72210628 | 72210642 | − | TCCACTGACCTTAGG | 285 | 0 |
| LTRA | TCCACTGACCTTAGG | 175 | chr6 | 100 | 20 | 160845640 | 160845654 | + | TCCACTGACCTTAGG | 286 | 0 |
| LTRA | TCCACTGACCTTAGG | 176 | chr3 | 100 | 20 | 2669093 | 2669107 | + | TCCACTGACCTTAGG | 287 | 0 |
| LTRA | TCCACTGACCTTAGG | 177 | chr3 | 100 | 20 | 158293370 | 158293384 | − | TCCACTGACCTTAGG | 288 | 0 |
| LTRA | TCCACTGACCTTAGG | 178 | chr2 | 100 | 20 | 237551230 | 237551244 | + | TCCACTGACCTTAGG | 289 | 0 |
| LTRA | TCCACTGACCTTGGG | 179 | chr20 | 100 | 20 | 46918345 | 46918359 | + | TCCACTGACCTTGGG | 290 | 0 |
| LTRA | TCCACTGACCTTGGG | 180 | chr14 | 100 | 20 | 86310067 | 86310081 | − | TCCACTGACCTTGGG | 291 | 0 |
| LTRA | TCCACTGACCTTGGG | 181 | chr12 | 100 | 20 | 116054688 | 116054702 | + | TCCACTGACCTTGGG | 292 | 0 |
| LTRA | TCCACTGACCTTGGG | 182 | chr11 | 100 | 20 | 103532094 | 103532108 | + | TCCACTGACCTTGGG | 293 | 0 |
| LTRA | TCCACTGACCTTGGG | 183 | chr10 | 100 | 20 | 132186431 | 132186445 | − | TCCACTGACCTTGGG | 294 | 0 |
| LTRA | TCCACTGACCTTGGG | 184 | chr8 | 100 | 20 | 144600475 | 144600489 | + | TCCACTGACCTTGGG | 295 | 0 |
| LTRA | TCCACTGACCTTGGG | 185 | chr5 | 100 | 20 | 21926319 | 21926333 | − | TCCACTGACCTTGGG | 296 | 0 |
| LTRA | TCCACTGACCTTGGG | 186 | chr4 | 100 | 20 | 95491921 | 95491935 | + | TCCACTGACCTTGGG | 297 | 0 |
| LTRA | TCCACTGACCTTTGG | 187 | HIV | 100 | 20 | 170 | 184 | − | TCCACTGACCTTTGG | 298 | 0 |
| LTRA | TCCACTGACCTTTGG | 188 | HIV | 100 | 20 | 9098 | 9112 | + | TCCACTGACCTTTGG | 299 | 0 |
| LTRA | TCCACTGACCTTTGG | 189 | chr16 | 100 | 20 | 86962569 | 86962583 | + | TCCACTGACCTTTGG | 300 | 0 |
| LTRA | TCCACTGACCTTTGG | 190 | chr11 | 100 | 20 | 68156214 | 68156228 | + | TCCACTGACCTTTGG | 301 | 0 |
| LTRA | TCCACTGACCTTTGG | 191 | chr6 | 100 | 20 | 98901054 | 98901068 | + | TCCACTGACCTTTGG | 302 | 0 |
| LTRA | TCCACTGACCTTTGG | 192 | chr5 | 100 | 20 | 72600080 | 72600094 | + | TCCACTGACCTTTGG | 303 | 0 |
| LTRA | TCCACTGACCTTTGG | 193 | chr5 | 100 | 20 | 136458169 | 136458183 | + | TCCACTGACCTTTGG | 304 | 0 |
| LTRA | TCCACTGACCTTTGG | 194 | chr4 | 100 | 20 | 253353030 | 253353044 | + | TCCACTGACCTTTGG | 305 | 0 |
| LTRA | TCCACTGACCTTTGG | 195 | chr2 | 100 | 20 | 207833373 | 207833387 | + | TCCACTGACCTTTGG | 306 | 0 |
| LTRA | TCCACTGACCTTAAG | 196 | chr15 | 100 | 20 | 678505069 | 678505200 | − | TCCACTGACCTTAAG | 307 | 0 |
| LTRA | TCCACTGACCTTAAG | 197 | chr7 | 100 | 20 | 155511293 | 155511307 | − | TCCACTGACCTTAAG | 308 | 0 |
| LTRA | TCCACTGACCTTAAG | 198 | chr5 | 100 | 20 | 25142541 | 25142555 | − | TCCACTGACCTTAAG | 309 | 0 |

Fig. 15, cont'd.

| name | SEQ ID NO: | query Seq | Subj. ID | Identity (%) | E-Value | start | end | strand | ref Seq | SEQ ID NO: | mismatch (12bp seed) |
|---|---|---|---|---|---|---|---|---|---|---|---|
| LTRA | 199 | TCCACTGACCTTAAG | chr3 | 100 | 20 | 116712579 | 116712593 | + | TCCACTGACCTTAAG | 310 | 0 |
| LTRA | 200 | TCCACTGACCTTAAG | chr1 | 100 | 20 | 163298514 | 163298528 | + | TCCACTGACCTTAAG | 311 | 0 |
| LTRA | 201 | TCCACTGACCTTCAG | chr20 | 100 | 20 | 22136764 | 22136778 | − | TCCACTGACCTTCAG | 312 | 0 |
| LTRA | 202 | TCCACTGACCTTCAG | chr19 | 100 | 20 | 50519462 | 50519476 | − | TCCACTGACCTTCAG | 313 | 0 |
| LTRA | 203 | TCCACTGACCTTCAG | chr18 | 100 | 20 | 74623621 | 74623635 | − | TCCACTGACCTTCAG | 314 | 0 |
| LTRA | 204 | TCCACTGACCTTCAG | chr16 | 100 | 20 | 71402733 | 71402747 | + | TCCACTGACCTTCAG | 315 | 0 |
| LTRA | 205 | TCCACTGACCTTCAG | chr14 | 100 | 20 | 24193180 | 24193194 | − | TCCACTGACCTTCAG | 316 | 0 |
| LTRA | 206 | TCCACTGACCTTCAG | chr11 | 100 | 20 | 133664063 | 133664077 | + | TCCACTGACCTTCAG | 317 | 0 |
| LTRA | 207 | TCCACTGACCTTCAG | chr9 | 100 | 20 | 140394271 | 140394285 | − | TCCACTGACCTTCAG | 318 | 0 |
| LTRA | 208 | TCCACTGACCTTCAG | chr6 | 100 | 20 | 47685256 | 47685270 | − | TCCACTGACCTTCAG | 319 | 0 |
| LTRA | 209 | TCCACTGACCTTCAG | chr5 | 100 | 20 | 152371290 | 152371304 | + | TCCACTGACCTTCAG | 320 | 0 |
| LTRA | 210 | TCCACTGACCTTCAG | chr4 | 100 | 20 | 110823169 | 110823183 | − | TCCACTGACCTTCAG | 321 | 0 |
| LTRA | 211 | TCCACTGACCTTCAG | chr3 | 100 | 20 | 46255327 | 46255341 | + | TCCACTGACCTTCAG | 322 | 0 |
| LTRA | 212 | TCCACTGACCTTCAG | chr3 | 100 | 20 | 186757301 | 186757315 | + | TCCACTGACCTTCAG | 323 | 0 |
| LTRA | 213 | TCCACTGACCTTGAG | chrX | 100 | 20 | 74260261 | 74260275 | − | TCCACTGACCTTGAG | 324 | 0 |
| LTRA | 214 | TCCACTGACCTTGAG | chr11 | 100 | 20 | 76052171 | 76052185 | + | TCCACTGACCTTGAG | 325 | 0 |
| LTRA | 215 | TCCACTGACCTTGAG | chr9 | 100 | 20 | 33927660 | 33927674 | + | TCCACTGACCTTGAG | 326 | 0 |
| LTRA | 216 | TCCACTGACCTTGAG | chr9 | 100 | 20 | 71035331 | 71035345 | − | TCCACTGACCTTGAG | 327 | 0 |
| LTRA | 217 | TCCACTGACCTTGAG | chr9 | 100 | 20 | 95871690 | 95871704 | + | TCCACTGACCTTGAG | 328 | 0 |
| LTRA | 218 | TCCACTGACCTTGAG | chr7 | 100 | 20 | 137681847 | 137681861 | + | TCCACTGACCTTGAG | 329 | 0 |
| LTRA | 219 | TCCACTGACCTTGAG | chr6 | 100 | 20 | 32460609 | 32460623 | + | TCCACTGACCTTGAG | 330 | 0 |
| LTRA | 220 | TCCACTGACCTTGAG | chr3 | 100 | 20 | 42344237 | 42344251 | + | TCCACTGACCTTGAG | 331 | 0 |
| LTRA | 221 | TCCACTGACCTTGAG | chr2 | 100 | 20 | 64643586 | 64643600 | + | TCCACTGACCTTGAG | 332 | 0 |
| LTRA | 222 | TCCACTGACCTTTAG | chr16 | 100 | 20 | 551335552 | 551335566 | + | TCCACTGACCTTTAG | 333 | 0 |
| LTRA | 223 | TCCACTGACCTTTAG | chr15 | 100 | 20 | 90072212 | 90072226 | + | TCCACTGACCTTTAG | 334 | 0 |
| LTRA | 224 | TCCACTGACCTTTAG | chr12 | 100 | 20 | 69006300 | 69006314 | + | TCCACTGACCTTTAG | 335 | 0 |
| LTRA | 225 | TCCACTGACCTTTAG | chr3 | 100 | 20 | 170680338 | 170680352 | − | TCCACTGACCTTTAG | 336 | 0 |
| LTRA | 226 | TCCACTGACCTTTAG | chr2 | 100 | 20 | 215414950 | 215414964 | − | TCCACTGACCTTTAG | 337 | 0 |

Fig. 15, cont'd.

| name | query Seq | SEQ ID NO: | Subj. ID | Identity (%) | E-Value | start | end | strand | ref Seq | SEQ ID NO: | mismatch (12bp seed) |
|---|---|---|---|---|---|---|---|---|---|---|---|
| LTRB | CAGCAGTTCTTGAAGTACTCCGG | 227 | HIV | 100 | 7.00E-04 | 9291 | 9313 | - | CAGCAGTTCTTGAAGTACTCCGG | 338 | 0 |
| LTRB | AGCAGTTCTTGAAGTACTCCGG | 228 | HIV | 100 | 0.003 | 9291 | 9312 | - | AGCAGTTCTTGAAGTACTCCGG | 339 | 0 |
| LTRB | GCAGTTCTTGAAGTACTCCGG | 229 | HIV | 100 | 0.009 | 9291 | 9311 | - | GCAGTTCTTGAAGTACTCCGG | 340 | 0 |
| LTRB | CAGTTCTTGAAGTACTCCGG | 230 | HIV | 100 | 0.033 | 9291 | 9310 | - | CAGTTCTTGAAGTACTCCGG | 341 | 0 |
| LTRB | AGTTCTTGAAGTACTCCGG | 231 | HIV | 100 | 0.12 | 9291 | 9309 | - | AGTTCTTGAAGTACTCCGG | 342 | 0 |
| LTRB | GTTCTTGAAGTACTCCGG | 232 | HIV | 100 | 0.42 | 9291 | 9308 | - | GTTCTTGAAGTACTCCGG | 343 | 0 |
| LTRB | TTCTTGAAGTACTCCGG | 233 | HIV | 100 | 1.5 | 9291 | 9307 | - | TTCTTGAAGTACTCCGG | 344 | 0 |
| LTRB | TCTTGAAGTACTCCGG | 234 | HIV | 100 | 5.4 | 9291 | 9306 | - | TCTTGAAGTACTCCGG | 345 | 0 |
| LTRB | TCTTGAAGTACTCTAG | 235 | chr11 | 100 | 5.4 | 91845834 | 91845849 | - | TCTTGAAGTACTCTAG | 346 | 0 |
| LTRB | CTTGAAGTACTCAGG | 236 | chr19 | 100 | 20 | 45672789 | 45672803 | - | CTTGAAGTACTCAGG | 347 | 0 |
| LTRB | CTTGAAGTACTCAGG | 237 | chr15 | 100 | 20 | 82132445 | 82132459 | - | CTTGAAGTACTCAGG | 348 | 0 |
| LTRB | CTTGAAGTACTCAGG | 238 | chr11 | 100 | 20 | 94282411 | 94282425 | + | CTTGAAGTACTCAGG | 349 | 0 |
| LTRB | CTTGAAGTACTCAGG | 239 | chr2 | 100 | 20 | 193312744 | 193312758 | + | CTTGAAGTACTCAGG | 350 | 0 |
| LTRB | CTTGAAGTACTCCGG | 240 | HIV | 100 | 20 | 9291 | 9305 | - | CTTGAAGTACTCCGG | 351 | 0 |
| LTRB | CTTGAAGTACTCTGG | 241 | chr15 | 100 | 20 | 61274973 | 61274987 | - | CTTGAAGTACTCTGG | 352 | 0 |
| LTRB | CTTGAAGTACTCAAG | 242 | chrX | 100 | 20 | 36051764 | 36051778 | - | CTTGAAGTACTCAAG | 353 | 0 |
| LTRB | CTTGAAGTACTCAAG | 243 | chr15 | 100 | 20 | 31316465 | 31316479 | - | CTTGAAGTACTCAAG | 354 | 0 |
| LTRB | CTTGAAGTACTCAAG | 244 | chr13 | 100 | 20 | 23054474 | 23054488 | - | CTTGAAGTACTCAAG | 355 | 0 |
| LTRB | CTTGAAGTACTCAAG | 245 | chr9 | 100 | 20 | 83208046 | 83208060 | + | CTTGAAGTACTCAAG | 356 | 0 |
| LTRB | CTTGAAGTACTCAAG | 246 | chr8 | 100 | 20 | 13956368 | 13956382 | - | CTTGAAGTACTCAAG | 357 | 0 |
| LTRB | CTTGAAGTACTCCAG | 247 | chr16 | 100 | 20 | 57449025 | 57449039 | - | CTTGAAGTACTCCAG | 358 | 0 |
| LTRB | CTTGAAGTACTCCAG | 248 | chr15 | 100 | 20 | 41397831 | 41397845 | - | CTTGAAGTACTCCAG | 359 | 0 |
| LTRB | CTTGAAGTACTCCAG | 249 | chr11 | 100 | 20 | 70255488 | 70255502 | - | CTTGAAGTACTCCAG | 360 | 0 |
| LTRB | CTTGAAGTACTCCAG | 250 | chr3 | 100 | 20 | 134149643 | 134149657 | + | CTTGAAGTACTCCAG | 361 | 0 |
| LTRB | CTTGAAGTACTCTAG | 251 | chr11 | 100 | 20 | 91845834 | 91845848 | - | CTTGAAGTACTCTAG | 362 | 0 |
| LTRB | CTTGAAGTACTCTAG | 252 | chr1 | 100 | 20 | 224520600 | 224520614 | + | CTTGAAGTACTCTAG | 363 | 0 |

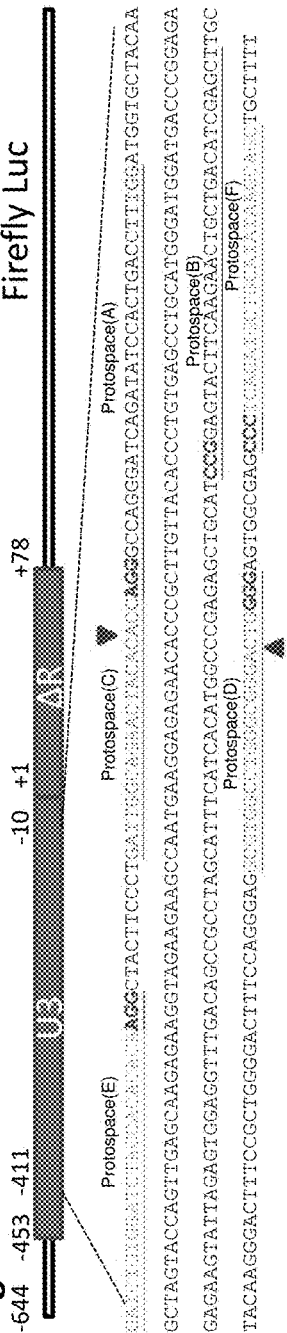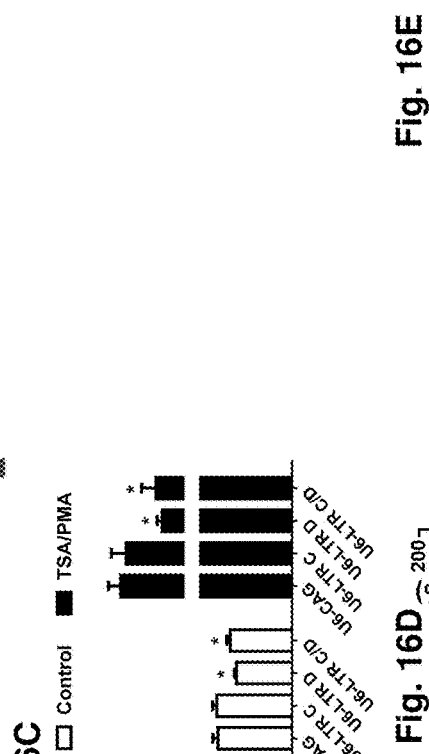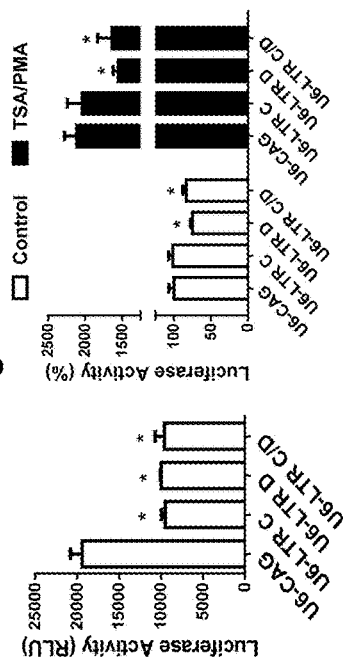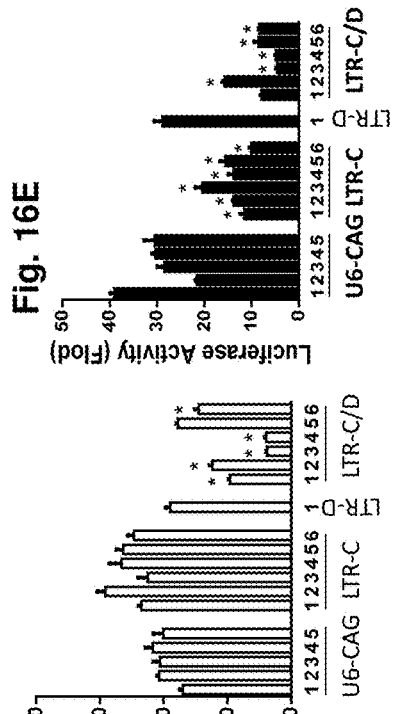

Fig. 18

HIV-1 LTR (634 bp)

Human immunodeficiency virus type 1, NY5/BRU (LAV-1) recombinant clone pNL4-3.
ACCESSION number: M19921

TGGAAGGGCTAATTCACTCCCAACGAAGACAAGATATCCTTGATCTGTGGATCTACCACACACAA

GGCTACTTCCCTGATTGGCAGAACTACACACCAGGGCCAGGGATCAGATATCCACTGACCTTTGG

ATGGTGCTACAAGCTAGTACCAGTTGAGCAAGAGGTAGAAGAAGCCAATGAAGGAGAGAACA

__U3 region__

CCCGCTTGTTACACCCTGTGAGCCTGCATGGGATGGATGACCCGGAGAGAGAAGTATTAGAGTGG

AGGTTTGACAGCCGCCTAGCATTTCATCACATGGCCCGAGAGCTGCATCCGGAGTACTTCAAGAA

CTGCTGACATCGAGCTTGCTACAAGGGACTTTCCGCTGGGGACTTTCCAGGGAGGCGTGGCCTGG

GCGGGACTGGGGAGTGGCGAGCCCTCAGATGCTGCATATAAGCAGCTGCTTTTTGCTTGTACTGG

__R region__

GTCTCTCTGGTTAGACCAGATCTGAGCCTGGGAGCTCTCTGGCTAACTAGGGAACCCACTGCTTA

AGCCTCAATAAAGCTTGCCTTGAGTGCTTCAAGTAGTGTGTGCCCGTCTGTTGTGTGACTCTGGT

__U5 region__

AACTAGAGATCCCTCAGACCCTTTTAGTCAGTGTGGAAAATCTCTAGCA

Fig. 19

SIVmm239-LTR(818bp)

Simian (macaque) immunodeficiency virus, isolate 239
Genebank number: M33262

```
TGGAAGGGATTTATTACAGTGCAAGAAGACATAGAATCTTAGACATATACTTAGAAAAGGAAGAAGGCATCAT
ACCAGATTGGCAGGATTACACCTCAGGACCAGGAATTAGATACCCAAAGACATTTGGCTGGCTATGGAAATTA
```
U3 region
```
GTCCCTGTAAATGTATCAGATGAGGCACAGGAGGATGAGGAGCATTATTTAATGCATCCAGCTCAAACTTCCC
AGTGGGATGACCCTTGGGAGAGGTTCTAGCATGGAAGTTTGATCCAACTCTGGCCTACACTTATGAGGCATA
TGTTAGATACCCAGAAGAGTTTGGAAGCAAGTCAGGCCTGTCAGAGGAAGAGGTTAGAAGAAGGCTAACCGCA
AGAGGCCTTCTTAACATGGCTGACAAGAAGGAAACTCGCTGAAAACAGCAGGAGGACTTTCCACAAGGGGATGTTA
CGGGGAGGTACTGGGGAGGAGCCGGTCGGGGAACGCCCACTTTCTTGATGTATAAATATCACTGCATTTCGCTC
```
R region
```
TGTATTCAGTCGCTCTGCCGAGACTGGCAGATTGAGCCCTGGAGGTTCTCTCCAGCACTAGCAGGTAGAG
CCTGGGTGTTCCCTGCTAGACTCTCACCAGCACTCTTGGCCGGTGCTGGGCAGAGTGACTCCACGCTTGCTTGCT
```
U5 region
```
TAAAGCCCCTCTCTTCAATAAAGCTGCCATTTTAGAAGTAAGCTAGTGTGTGTTCCCATCTCTCCTAGTCGCCGCC
TGGTCAACTCGGTACTCAATAATAAGAAGACCCTGGTCTGTTAGGACCCTTTCTGCTTTGGGAAACGGAAGCA
GGAAAATCCCTAGCA
```

METHODS AND COMPOSITIONS FOR RNA-GUIDED TREATMENT OF HIV INFECTION

STATEMENT REGARDING FEDERALLY SPONSORED RESEARCH

This invention was made with U.S. government support under grant numbers R01MH093271, R01NS087971, and P30MH092177 awarded by the National Institutes of Health. The U.S. government may have certain rights in the invention.

BACKGROUND OF THE INVENTION

1. Technical Field

The present invention relates to compositions that specifically cleave target sequences in retroviruses, for example human immunodeficiency virus (HIV). Such compositions, which can include nucleic acids encoding a Clustered Regularly Interspace Short Palindromic Repeat (CRISPR) associated endonuclease and a guide RNA sequence complementary to a target sequence in a human immunodeficiency virus, can be administered to a subject having or at risk for contracting an HIV infection.

2. Background Art

For more than three decades since the discovery of HIV-1, AIDS remains a major public health problem affecting greater than 35.3 million people worldwide. AIDS remains incurable due to the permanent integration of HIV-1 into the host genome. Current therapy (highly active antiretroviral therapy or HAART) for controlling HIV-1 infection and impeding AIDS development profoundly reduces viral replication in cells that support HIV-1 infection and reduces plasma viremia to a minimal level. But HAART fails to suppress low level viral genome expression and replication in tissues and fails to target the latently-infected cells, for example, resting memory T cells, brain macrophages, microglia, and astrocytes, gut-associated lymphoid cells, that serve as a reservoir for HIV-1. Persistent HIV-1 infection is also linked to co-morbidities including heart and renal diseases, osteopenia, and neurological disorders. There is a continuing need for curative therapeutic strategies that target persistent viral reservoirs.

SUMMARY OF THE INVENTION

Provided herein are compositions and methods relating to treatment and prevention of retroviral infections. The retrovirus can be a lentivirus, for example, a human immunodeficiency virus, a simian immunodeficiency virus, a feline immunodeficiency virus or a bovine immunodeficiency virus. The human immunodeficiency virus can be HIV-1 or HIV-2. In one embodiment, the compositions include a nucleic acid sequence comprising a sequence encoding a CRISPR-associated endonuclease and one or more guide RNAs, wherein the guide RNA is complementary to a target sequence in a human immunodeficiency virus. In some embodiments the nucleic acid is contained within an expression vector. In one embodiment, the compositions include a CRISPR-associated endonuclease polypeptide and one or more guide RNAs, wherein the guide RNA is complementary to a target sequence in a human immunodeficiency virus. Also provided are pharmaceutical compositions that include the nucleic acids, expression vectors, or polypeptides disclosed herein. Also provided herein are methods of treatment of the subject having or at risk for having a human immunodeficiency virus infection, wherein the method of treatment comprises administering to a subject a therapeutically effective amount of a composition comprising a vector encoding a CRISPR-associated endonuclease and one or more guide RNAs, wherein the guide RNA is complementary to a target sequence in the a human immunodeficiency virus. Also provided are methods of inactivating a retrovirus in a human cell by exposing the cell to a composition comprising an isolated nucleic acid encoding a gene editing complex comprising a CRISPR-associated endonuclease and one or more guide RNAs wherein the guide RNA is complementary to a target nucleic acid sequence in the retrovirus. The gene editing complex introduces one or more mutations into the proviral DNA. In some embodiments the mutations can include the deletion, which can comprise all or substantially all of the proviral DNA sequence. In another aspect, a kit comprising a measured amount of the compositions disclosed herein is also provided.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1H show that Cas9/LTR-gRNA suppresses HIV-1 reporter virus production in CHME5 microglial cells latently infected with HIV-1. (1A) Representative gating diagram of EGFP flow cytometry shows a dramatic reduction in TSA-induced reactivation of latent pNL4-3-ΔGag-d2EGFP reporter virus by stably expressed Cas9 plus LTR-A or —B, vs. empty U6-driven gRNA expression vector (U6-CAG). (1B) SURVEYOR Cel-I nuclease assay of PCR product (−453 to +43 within LTR) from selected LTR-A- or -B-expressing stable clones shows dramatic indel mutation patterns (arrows). (1C, 1D) PCR fragment analysis shows a precise deletion of 190-bp region between LTRs A and B cutting sites (arrowhead and arrow in 1D), leaving 306-bp fragment (arrow in 1C) validated by TA-cloning and sequencing results. FIG. 1D discloses SEQ ID NOS 1-3, respectively, in order of appearance. (1E-1G) Subcloning of LTR-A/B stable clones reveals complete loss of reporter reactivation determined by EGFP flow cytometry (1E) and elimination of pNL4-3-ΔGag-d2EGFP proviral genome detected by standard (1F) and real-time (1G) PCR amplification of genomic DNA for EGFP and HIV-1 Rev response element (RRE); β-actin is a DNA purification and loading control. (1H) PCR genotyping of LTR-A/B subclones (#8, 13) using primers to amplify DNA fragment covering HIV-1 LTR U3/R/U5 regions (−411 to +129) shows indels (a, deletion; c, insertion) and "intact" or combined LTR (b).

FIG. 2B discloses SEQ ID NOS 4-13, respectively, in order of appearance. (2C) Functional analysis of LTR-A/B-induced eradication of HIV-1 genome, showing substantial blockade of TSA/PMA reactivation-induced p24 virion release. U1 cells were transfected with pX260-LTRs-A, —B, or -A/B. After 2-week puromycin selection, cells were treated with TSA (250 nM)/PMA for 2 days before p24 Gag ELISA was performed.

FIGS. 3A-3B show that stable expression of Cas9 plus LTR-A/B vaccinates TZM-bl cells against new HIV-1 virus infection. (3A) Immunocytochemistry (ICC) and Western blot (WB) analyses with anti-Flag antibody confirm the expression of Flag-Cas9 in TZM-bl stable clones puromycin (2 μg/ml)-selected for 2 weeks. (3B) PCR genotyping of Cas9/LTR-A/B stable clones (c1-c7) reveals a close correlation of LTR excision with repression of LTR luciferase reporter activation. Fold changes represent TSA/PMA-induced levels over corresponding non-induction levels. (3C) Stable Cas9/LTR-A/B-expressing cells (c4) were infected with pseudotyped-pNL4-3-Nef-EGFP lentivirus at indicated multiplicity of infection (MOI) and infection efficiency measured by EGFP flow cytometry, 2 d post-infection. (3D) Representative phase-contrast/fluorescence micrographs show that LTR-A/B stable, but not control (U6-CAG; black) cells, are resistant to new infection (right panel) by pNL4-3-ΔE-EGFP HIV-1 reporter virus (gray).

FIGS. 4A-4D illustrate the off-target effects of Cas9/LTR-A/B on the human genome. (4A) SURVEYOR assay shows no indel mutations in predicted/potential off-target regions in human TZM-bl and U1 cells. LTR-A on-target region (A) was used as a positive control and empty U6-CAG vector (U6) as a negative control. (4B-4D) Whole-genome sequencing of LTR-A/B stable TZM-bl subclone showing the numbers of called indels in the U6-CAG control and LTR-A/B samples (4B), detailed information on 10 called indels near gRNA target sites in both samples (4C), and distribution of off-target called indels (4D). FIG. 4C discloses SEQ ID NOS 14-15, respectively, in order of appearance.

FIG. 5 shows the LTR U3 sequence of the integrated lentiviral LTR-firefly luciferase reporter identified by TA-cloning and sequencing of PCR product (−411 to −10) from the genomic DNA of human TZM-bl cells. The protospacer and PAM (NGG) sequences of 4 gRNAs (LTR-A to D) and the predicted binding sites of indicated transcription factors are highlighted. The precise cleavage sites are marked with scissors. +1 indicates the transcriptional start site. FIG. 5 discloses SEQ ID NO: 16.

FIGS. 7A-7F show that both LTR-C and LTR-D induced indel mutations and significantly decreased constitutive and TSA/PMA-induced luciferase activity in TZM-bl cells stably incorporated with HIV-1 LTR-firefly luciferase reporter gene. (7A) Functional luciferase reporter assay revealing a significant reduction of LTR reactivation by LTR-C, LTR-D or both. (7B) SURVEYOR assay showing indel mutation in LTR DNA (−453 to +43) induced by LTR-C and LTR-D (upper arrow). A combination of LTR-C and LTR-D generates a 194 bp fragment (lower arrow) resulting from the deletion of 302 bp region between LTR-C and LTR-D. (7C, 7D) Sanger sequencing of 30 clones validating the indel efficiency at 23% for LTR-C and 13% for LTR-D and example chromatograms showing insertion/deletion. FIG. 7C discloses SEQ ID NOS 17-25, respectively, in order of appearance. FIG. 7D discloses SEQ ID NOS 26-30, respectively, in order of appearance. (7E) PCR-restriction fragment length polymorphism (RFLP) analysis using BsaJ I to cut 5 sites (96, 102, 372, 386, 482) of the PCR product covering −453 to +43 of LTR showing two major bands (96 bp and 270 bp) in the U6-CAG control sample, but an additional 372 bp band (upper arrow) after LTR-C-induced indel mutation at the 96/102 sites, a 290 bp band (middle arrow) after LTR-D-induced mutations at the 372 site and a 180 bp fragment (lower arrow) after LTR-C/D-induced excision. (7F) Example chromatograms showing the deletion of a 302 bp fragment between LTR-C and LTR-D (top) and an additional 17 bp deletion (bottom). Red arrows indicate the junction sites. *P<0.05 indicates a significant decrease in LTR-C or LTR-D-mediated luciferase activation compared to U6-CAG control. FIG. 7F discloses SEQ ID NOS 31-32, respectively, in order of appearance.

FIGS. 8A-8C illustrate the TA cloning and Sanger sequencing of PCR products from CHME5 subclones of LTR-A/B and empty U6-CAG control using primers covering HIV-1 LTR U3/R/U5 regions (−411 to +129). (8A) Possible combination of LTR-A and LTR-B cuts on both 5'- and 3'-LTRs generating potential fragments a-c as indicated. (8B) Blasting of fragment a (351 bp) showing 190 bp deletion between LTR-A and LTR-B cut sites. (8C) Blast of fragment c (682 bp) showing a 175 bp insertion at the LTR-A cleavage site and a 27 bp deletion at the LTR-B cleavage site. FIG. 8C discloses SEQ ID NOS 33-34, respectively, in order of appearance.

FIGS. 9A-9D demonstrate that Cas9/LTR-gRNA efficiently eradicates latent HIV-1 virus from U1 monocytic cells. (9A) Sanger sequencing of a 1.1 kb fragment from long-range PCR using a primer pair (T492/T493) targeting a chromosome 2 integration site-flanking sequence (small letters, 467-bp) reveals elimination of the entire HIV-1 genome (9709-bp), leaving combined 5'-LTR (underlined using dashes) and 3'-LTR with a 6-bp insertion (boxed) precisely at the third nucleotide from PAM (TGG) LTR-A targeting site (underlined) and a 4-bp deletion (nnnn). FIG. 9A discloses SEQ ID NO: 35. (9B) The representative DNA gel picture shows specific eradication of the HIV-1 genome. NS, non-specific band. (9C, 9D) Quantitative PCR analysis using the primer pair targeting the Gag gene (T457/T458) shows 85% efficiency of entire HIV-1 genome eradication in Cas9/LTR-A/B-expressing U1 cells. U1 cells were transfected with pX260 empty vector (U6-CAG) or LTRs-A/B-encoding vectors. After 2-week puromycin selection, the cellular genomic DNAs were used for absolute quantitative qPCR analysis using spiked pNL4-3-ΔE-EGFP human genomic DNA as a standard. **P<0.01 indicates a significant decrease compared to the U6-CAG control.

FIGS. 10A-10C show that Cas9/LTR gRNAs effectively eradicates HIV-1 provirus in J-Lat latently infected T cells. (10A) Functional analysis by EGFP flow cytometry reveals approximately 50% reduction of PMA and TNFα-induced reactivation of EGFP reporter viruses. (10B) The SURVEYOR assay shows indel mutations (arrow) in the on-target LTR genome of Cas9/LTR-A/B transfected cells. J-Lat cells were transfected with pX260 empty vector or LTRs-A and -B. After 2-week puromycin selection, cells were treated with PMA or TNFα for 24 h. The genomic DNAs were subject to PCR using primers covering HIV-1 LTR U3/R/U5 regions (−411 to +129) and the SURVEYOR assay was performed. **P<0.01 indicates a significant decrease compared to the U6-CAG control. (10C) PCR fragment analysis using primers covering HIV-1 LTR (−374 to +43) shows a precise deletion of 190-bp region between LTRs A and B cutting sites, leaving 227-bp fragment (arrow). House-keeping gene β-actin serves as a DNA purification and loading control.

FIGS. 12A-12D demonstrate that stable expression of Cas9/LTR-A/B gRNAs in TZM-bl cells vaccinates against pseudotyped or native HIV-1 viruses. (12A) Flow cytometry shows a significant reduction of native pNL4-3-ΔE-EGFP reporter virus infection efficiency in Cas9/LTR-A/B expressing TZM-bl subclones. (12B, 12C) Real-time PCR analysis reveals suppression or elimination of viral RNA (12B) and DNA (12C) by Cas9/LTR-A/B gRNAs. (12D) The firefly-luciferase luminescent assay demonstrates dramatic inhibition of virus infection-stimulated LTR promoter activity by Cas9/LTR-A/B gRNAs. The stable Cas9/LTR-A/B gRNA-expressing TZM-bl cells were infected for 2 hours with indicated native HIV-1 viruses, and washed twice with PBS. At 2 days post-infection, cells were collected, fixed and analyzed by flow cytometry for EGFP expression (12A), or lysed for total RNA extraction and RT-qPCR (12B), genomic DNA purification for qPCR (12C) and luminescence measurement (12D). *P<0.05 and **P<0.01 indicate significant decreases compared to the U6-CAG control.

FIG. 13 shows the predicted LTR gRNAs and their off-target numbers (100% match). The 5'-LTR sense and antisense sequences (SEQ ID NOS 79-111 and 112-141, respectively) (634 bp) of pHR'-CMV-LacZ lentiviral vector (AF105229) were utilized to search for Cas9/gRNA target sites containing a 20-bp guide sequence (protospacer) plus the protospacer adjacent motif sequence (NGG) using Jack Lin's CRISPR/Cas9 g RNA finder tool. Each gRNA plus NGG (AGG, TGG, GGG, CGG) was blasted against available human genomic and transcript sequences with 1000 aligned sequences being displayed. After pressing Control+F, copy/paste the target sequence (1-23 through 9-23 nucleotides) and find the number of genomic targets with 100% match. The number of off-targets for each searching was divided by 3 because of repeated genome library. The number shown indicates the sum of 4 searches (NGG). The top number (for example, for gRNA sequence (sense): 20, 19, 19, 17, 16, 15, 14, 13, 12) indicates the gRNA target sequences farthest from NGG. The sequence and off-target numbers for the selected LTR-A/B and LTR-C/D are highlighted red and green respectively.

FIG. 14 depicts the oligonucleotides for gRNA targeting sites and primers (SEQ ID NOS 36-78, respectively, in order of appearance) used for PCR and sequencing.

FIG. 15 shows the locations of predicted gRNA targeting sites of LTR-A and LTR-B and discloses "query Seq" sequences as SEQ ID NOS 142-252, and "ref Seq" sequences as SEQ ID NOS 253-363, all respectively, in order of appearance.

FIG. 16A, FIG. 16B, FIG. 16C, FIG. 16D, FIG. 16E, FIG. 16F, FIG. 16G, and FIG. 16H show that both LTR-C and LTR-D decreased constitutive and TSA/PMA-induced luciferase activity in TZMBI cells stably incorporated with HIV-1 LTR firefly luciferase reporter gene and combination induced precise genome excision. FIG. 16A shows that six gRNA targets were designed for the promoter region of HIV-LTR. FIG. 16A discloses SEQ ID NO: 16. TZMBI cells were cotransfected with Cas9-EGFP and chimera gRNA expression cassette (PCR products) by LIPOFECTAMINE® 2000. FIG. 16B is a graph showing that after 3 d, EGFP-positive cells were sorted through FACS and 2000 cells per group were collected for luciferase assay. FIG. 16B discloses SEQ ID: 31. FIG. 16C is a graph showing the population sorted cells were cultured for 2 d and treated with TSA/PMA for 1 d before luciferase assay. The single cells were sorted into 96-well plate and cultured till confluence for luciferase assay in the absence (shown in the graph of FIG. 16D) of TSA/PMA for 1 d or presence (shown in the graph of FIG. 1E) of TSA/PMA for 1 d. FIG. 16F and FIG. 16G show the PCR product from the population sorted cells were analyzed with Surveyor Cel-I nuclease assay and restriction fragment length polymorphism with Bsajl (FIG. 16G) showing mutation (FIG. 16F) or uncut (FIG. 16G) band (red arrow). A 200 bp fragment (FIG. 16F, FIG. 16G, black arrow) resulting from the deletion of 321 bp region between LTR-C and LTR-D as predicted (FIG. 16A, red arrowhead) was validated by TA-cloning and sequencing showing precise genomic excision (FIG. 16H). Sanger sequencing of PCR products from individual LTR-C and -D identified % and % indel mutation efficiency respectively. * p<0.05 indicates statistically significant reduction using a student's t test compared to the corresponding U6-CAG control. Protospace(E), Protospace(C), Protospace(A), Protospace(B), Protospace(D), and Protospace(F) correspond to SEQ ID NOS 365, 367, 369, 371, 373, and 375, respectively, in order of appearance.

FIG. 17H discloses SEQ ID NOS 1-3, respectively, in order of appearance.

FIG. 18 shows LTR of a representative HIV-1 sequence (SEQ ID NO: 376). The U3 region extends from nucleotide 1 to nucleotide 432 (SEQ ID NO: 377), the R region extends from nucleotide 432 to nucleotide 559 (SEQ ID NO: 378), and the U5 region extends from 560 to nucleotide 634 (SEQ ID NO: 379).

FIG. 19 shows LTR of a representative SIV sequence (SEQ ID NO: 380). The U3 region extends from nucleotide 1 to nucleotide 517 (SEQ ID NO: 381), the R region extends from nucleotide 518 to nucleotide 693 (SEQ ID NO: 382), and the U5 region extends from 694 to nucleotide 818 (SEQ ID NO: 383).

DETAILED DESCRIPTION OF THE INVENTION

Figure 1F:
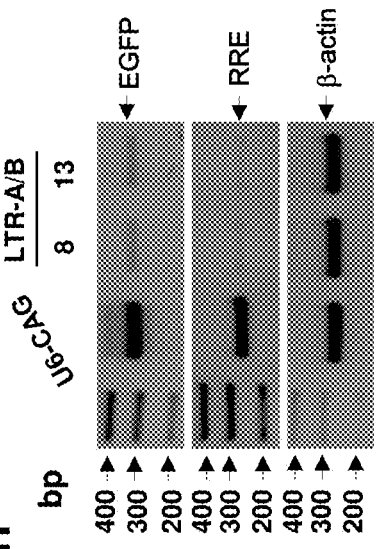

The present invention is based, in part, on our discovery that we could eliminate the integrated HIV-1 genome from HIV-1 infected cells by using the RNA-guided Clustered Regularly Interspace Short Palindromic Repeat (CRISPR)-Cas 9 nuclease system (Cas9/gRNA) in single and multiplex configurations. We identified highly specific targets within the HIV-1 LTR U3 region that were efficiently edited by Cas9/gRNA, inactivating viral gene expression and replication in latently-infected microglial, promonocytic and T cells. Cas9/gRNAs caused neither genotoxicity nor off-target editing to the host cells, and completely excised a 9709-bp fragment of integrated proviral DNA that spanned from its 5'- to 3'-LTRs. Furthermore, the presence of multiplex gRNAs within Cas9-expressing cells prevented HIV-1 infection. Our results suggest that Cas9/gRNA can be engineered to provide a specific, efficacious prophylactic and therapeutic approach against AIDS.

Accordingly, the invention features compositions comprising a nucleic acid encoding a CRISPR-associated endonuclease and a guide RNA that is complementary to a target sequence in a retrovirus, e.g., HIV, as well as pharmaceutical formulations comprising a nucleic acid encoding a CRISPR-associated endonuclease and a guide RNA that is complementary to a target sequence in HIV. Also featured are compositions comprising a CRISPR-associated endonuclease polypeptide and a guide RNA that is complementary to a target sequence in HIV, as well as pharmaceutical formulations comprising a CRISPR-associated endonuclease polypeptide and a guide RNA that is complementary to a target sequence in HIV.

Also featured are methods of administering the compositions to treat a retroviral infection, e.g., HIV infection, methods of eliminating viral replication, and methods of preventing HIV infection. The therapeutic methods described herein can be carried out in connection with other antiretroviral therapies (e.g., HAART).

The clinical course of HIV infection can vary according to a number of factors, including the subject's genetic background, age, general health, nutrition, treatment received, and the HIV subtype. In general, most individuals develop flu-like symptoms within a few weeks or months of infection. The symptoms can include fever, headache, muscle aches, rash, chills, sore throat, mouth or genital ulcers, swollen lymph glands, joint pain, night sweats, and diarrhea. The intensity of the symptoms can vary from mild to severe depending upon the individual. During the acute phase, the HIV viral particles are attracted to and enter cells expressing the appropriate CD4 receptor molecules. Once the virus has entered the host cell, the HIV encoded reverse transcriptase generates a proviral DNA copy of the HIV RNA and the pro-viral DNA becomes integrated into the host cell genomic DNA. It is this HIV provirus that is replicated by the host cell, resulting in the release of new HIV virions which can then infect other cells. The methods and compositions of the invention are generally and variously useful for excision of integrated HIV proviral DNA, although the invention is not so limited, and the compositions may be administered to a subject at any stage of infection or to an uninfected subject who is at risk for HIV infection.

The primary HIV infection subsides within a few weeks to a few months, and is typically followed by a long clinical "latent" period which may last for up to 10 years. The latent period is also referred to as asymptomatic HIV infection or chronic HIV infection. The subject's CD4 lymphocyte numbers rebound, but not to pre-infection levels and most subjects undergo seroconversion, that is, they have detectable levels of anti-HIV antibody in their blood, within 2 to 4 weeks of infection. During this latent period, there can be no detectable viral replication in peripheral blood mononuclear cells and little or no culturable virus in peripheral blood. During the latent period, also referred to as the clinical latency stage, people who are infected with HIV may experience no HIV-related symptoms, or only mild ones. But, the HIV virus continues to reproduce at very low levels. In subjects who have treated with anti-retroviral therapies, this latent period may extend for several decades or more. However, subjects at this stage are still able to transmit HIV to others even if they are receiving antiretroviral therapy, although anti-retroviral therapy reduces the risk of transmission. As noted above, anti-retroviral therapy does not suppress low levels of viral genome expression nor does it efficiently target latently infected cells such as resting memory T cells, brain macrophages, microglia, astrocytes and gut associated lymphoid cells.

Clinical signs and symptoms of AIDS (acquired immunodeficiency syndrome) appear as CD4 lymphocyte numbers decrease, resulting in irreversible damage to the immune system. Many patients also present with AIDS-related complications, including, for example, opportunistic infections such as tuberculosis, *salmonellosis*, cytomegalovirus, candidiasis, cryptococcal meningitis, toxoplasmosis, and cryptosporidiosis, as well as certain kinds of cancers, including for example, Kaposi's sarcoma, and lymphomas, as well as wasting syndrome, neurological complications, and HIV-associated nephropathy.

Compositions

The compositions of the invention include nucleic acids encoding a CRISPR-associated endonuclease, e.g., Cas9, and a guide RNA that is complementary to a target sequence in a retrovirus, e.g., HIV. In bacteria the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR (Clustered Regularly Interspaced Short Palindromic Repeats) RNA (crRNA). The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or H1-promoted RNA expression vector, although cleavage efficiencies of the artificial sgRNA are lower than those for systems with the crRNA and tracrRNA expressed separately.

The compositions of the invention can include a nucleic acid encoding a CRISPR-associated endonuclease. In some embodiments, the CRISPR-associated endonuclease can be a Cas9 nuclease. The Cas9 nuclease can have a nucleotide sequence identical to the wild type *Streptococcus pyrogenes* sequence. In some embodiments, the CRISPR-associated endonuclease can be a sequence from other species, for example other *Streptococcus* species, such as *thermophilus; Psuedomona aeruginosa, Escherichia coli*, or other sequenced bacteria genomes and archaea, or other prokaryotic microorganisms. Alternatively, the wild type *Streptococcus pyrogenes* Cas9 sequence can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, Mass.). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

The Cas9 nuclease sequence can be a mutated sequence. For example the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks.

In some embodiments, compositions of the invention can include a CRISPR-associated endonuclease polypeptide encoded by any of the nucleic acid sequences described above. The terms "peptide," "polypeptide," and "protein" are used interchangeably herein, although typically they refer to peptide sequences of varying sizes. We may refer to the amino acid-based compositions of the invention as "polypeptides" to convey that they are linear polymers of amino acid residues, and to help distinguish them from full-length proteins. A polypeptide of the invention can "constitute" or "include" a fragment of a CRISPR-associated endonuclease, and the invention encompasses polypeptides that constitute or include biologically active variants of a CRISPR-associated endonuclease. It will be understood that the polypeptides can therefore include only a fragment of a CRISPR-associated endonuclease (or a biologically active variant thereof) but may include additional residues as well. Biologically active variants will retain sufficient activity to cleave target DNA.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a CRISPR-associated endonuclease can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

One or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

Alternatively, or in addition, one or more of the amino acid residues in a biologically active variant can be a naturally occurring residue that differs from the naturally occurring residue found in the corresponding position in a wildtype sequence. In other words, biologically active variants can include one or more amino acid substitutions. We may refer to a substitution, addition, or deletion of amino acid residues as a mutation of the wildtype sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a CRISPR-associated endonuclease can be characterized in terms of the extent to which their sequence is similar to or identical to the corresponding wild-type polypeptide. For example, the sequence of a biologically active variant can be at least or about 80% identical to corresponding residues in the wild-type polypeptide. For example, a biologically active variant of a CRISPR-associated endonuclease can have an amino acid sequence with at least or about 80% sequence identity (e.g., at least or about 85%, 90%, 95%, 97%, 98%, or 99% sequence identity) to a CRISPR-associated endonuclease or to a homolog or ortholog thereof.

A biologically active variant of a CRISPR-associated endonuclease polypeptide will retain sufficient biological activity to be useful in the present methods. The biologically active variants will retain sufficient activity to function in targeted DNA cleavage. The biological activity can be assessed in ways known to one of ordinary skill in the art and includes, without limitation, in vitro cleavage assays or functional assays.

Polypeptides can be generated by a variety of methods including, for example, recombinant techniques or chemical synthesis. Once generated, polypeptides can be isolated and purified to any desired extent by means well known in the art. For example, one can use lyophilization following, for example, reversed phase (preferably) or normal phase HPLC, or size exclusion or partition chromatography on polysaccharide gel media such as Sephadex G-25. The composition of the final polypeptide may be confirmed by amino acid analysis after degradation of the peptide by standard means, by amino acid sequencing, or by FAB-MS techniques. Salts, including acid salts, esters, amides, and N-acyl derivatives of an amino group of a polypeptide may be prepared using methods known in the art, and such peptides are useful in the context of the present invention.

The compositions of the invention include sequence encoding a guide RNA (gRNA) comprising a sequence that is complementary to a target sequence in a retrovirus. The retrovirus can be a lentivirus, for example, a human immunodeficiency virus, a simian immunodeficiency virus, a feline immunodeficiency virus or a bovine immunodeficiency virus. The human immunodeficiency virus can be HIV-1 or HIV-2. The target sequence can include a sequence from any HIV, for example, HIV-1 and HIV-2, and any circulating recombinant form thereof. The genetic variability of HIV is reflected in the multiple groups and subtypes that have been described. A collection of HIV sequences is compiled in the Los Alamos HIV databases and compendiums. The methods and compositions of the invention can be applied to HIV from any of those various groups, subtypes, and circulating recombinant forms. These include for example, the HIV-1 major group (often referred to as Group M) and the minor groups, Groups N, O, and P, as well as but not limited to, any of the following subtypes, A, B, C, D, F, G, H, J and K. or group (for example, but not limited to any of the following Groups, N, O and P) of HIV. The methods and compositions can also be applied to HIV-2 and any of the A, B, C, F or G clades (also referred to as "subtypes" or "groups"), as well as any circulating recombinant form of HIV-2.

The guide RNA can be a sequence complimentary to a coding or a non-coding sequence. For example, the guide RNA can be an HIV sequence, such as a long terminal repeat (LTR) sequence, a protein coding sequence, or a regulatory sequence. In some embodiments, the guide RNA comprises a sequence that is complementary to an HIV long terminal repeat (LTR) region. The HIV-1 LTR is approximately 640 bp in length. An exemplary HIV-1 LTR is the sequence of SEQ ID NO: 376. An exemplary SIV LTR is the sequence of SEQ ID NO: 380. HIV-1 long terminal repeats (LTRs) are divided into U3, R and U5 regions. Exemplary HIV-1 LTR U3, R and U5 regions are SEQ ID NOs: 377, 378 and 379, respectively. Exemplary SIV LTR U3, R and U5 regions are SEQ ID NOs: 381, 382, and 383, respectively. The configuration of the U1, R, U5 regions for exemplary HIV-1 and SIV sequences are shown in FIGS. 18 and 19, respectively. LTRs contain all of the required signals for gene expression and are involved in the integration of a provirus into the genome of a host cell. For example, the basal or core promoter, a core enhancer and a modulatory region is found within U3 while the transactivation response element is found within R. In HIV-1, the U5 region includes several sub-regions, for example, TAR or trans-acting responsive element, which is involved in transcriptional activation; Poly A, which is involved in dimerization and genome packaging; PBS or primer binding site; Psi or the packaging signal; DIS or dimer initiation site Useful guide sequences are complementary to the U3, R, or U5 region of the LTR. Exemplary guide RNA sequences that target the U3 region of HIV-1 are shown in FIG. 13. A guide RNA sequence can comprise, for example, a sequence complementary to the target protospacer sequence of:

```
                                      (SEQ ID NO: 96)
LTR A: ATCAGATATCCACTGACCTTTGG, (SEQ ID NO: 121)
LTR B: CAGCAGTTCTTGAAGTACTCCGG, (SEQ ID NO: 87)
LTR C: GATTGGCAGAACTACACACCAGG,
or (SEQ ID NO: 110)
LTR D: GCGTGGCCTGGGCGGGACTGGGG.
```

The locations of LTR A (SEQ ID NO: 96), LTR B (SEQ ID NO: 121), LTR C (SEQ ID NO: 87) and LTR D (SEQ ID NO: 110) within the U3 (SEQ ID NO: 16) region are shown FIG. 5. Additional exemplary guide RNA sequences that target the U3 region are listed in the table shown in FIG. 13 and can have the sequence of any of SEQ ID NOs: 79-111 and SEQ ID NOs: 111-141. In some embodiments, the guide sequence can comprise a sequence having 95% identity to any of SEQ ID NOs: 79-111 and SEQ ID NOs: 111-141. Thus, a guide RNA sequence can comprise, for example, a sequence having 95% identity to a sequence complementary to the target protospacer sequence of:

```
                                      (SEQ ID NO: 96)
LTR A: ATCAGATATCCACTGACCTTTGG, (SEQ ID NO: 121)
LTR B: CAGCAGTTCTTGAAGTACTCCGG, (SEQ ID NO: 87)
LTR C  GATTGGCAGAACTACACACCAGG,
or (SEQ ID NO: 110)
LTR D: GCGTGGCCTGGGCGGGACTGGGG.
```

We may also be refer to the guide RNA sequence as a spacer, e.g., spacer (A), spacer (B), spacer (C), and spacer (D).

The guide RNA sequence can be complementary to a sequence found within an HIV-1 U3, R, or U5 region reference sequence or consensus sequence. The invention is not so limiting however, and the guide RNA sequences can be selected to target any variant or mutant HIV sequence. In some embodiments, more than one guide RNA sequence is employed, for example a first guide RNA sequence and a second guide RNA sequence, with the first and second guide RNA sequences being complimentary to target sequences in any of the above mentioned retroviral regions. In some embodiments, the guide RNA can include a variant sequence or quasi-species sequence. In some embodiments, the guide RNA can be a sequence corresponding to a sequence in the genome of the virus harbored by the subject undergoing treatment. Thus for example, the sequence of the particular U3, R, or U5 region in the HIV virus harbored by the subject can be obtained and guide RNAs complementary to the patient's particular sequences can be used.

In some embodiments, the guide RNA can be a sequence complimentary to a protein coding sequence, for example, a sequence encoding one or more viral structural proteins, (e.g., gag, pol, env and tat). Thus, the sequence can be complementary to sequence within the gag polyprotein, e.g., MA (matrix protein, p17); CA (capsid protein, p24); SP1 (spacer peptide 1, p2); NC (nucleocapsid protein, p7); SP2 (spacer peptide 2, p1) and P6 protein; pol, e.g., reverse transcriptase (RT) and RNase H, integrase (IN), and HIV protease (PR); env, e.g., gp160, or a cleavage product of gp160, e.g., gp120 or SU, and gp41 or TM; or tat, e.g., the 72-amino acid one-exon Tat or the 86-101 amino-acid two-exon Tat. In some embodiments, the guide RNA can be a sequence complementary to a sequence encoding an accessory protein, including, for example, vif, nef (negative factor) vpu (Virus protein U) and tev.

In some embodiments, the sequence can be a sequence complementary to a structural or regulatory element, for example, an LTR, as described above; TAR (Target sequence for viral transactivation), the binding site for Tat protein and for cellular proteins, consists of approximately the first 45 nucleotides of the viral mRNAs in HIV-1 (or the first 100 nucleotides in HIV-2) forms a hairpin stem-loop structure; RRE (Rev responsive element) an RNA element encoded within the env region of HIV-1, consisting of approximately 200 nucleotides (positions 7710 to 8061 from the start of transcription in HIV-1, spanning the border of gp120 and gp41); PE (Psi element), a set of 4 stem-loop structures preceding and overlapping the Gag start codon; SLIP, a TTTTTT "slippery site", followed by a stem-loop structure; CRS (Cis-acting repressive sequences); INS Inhibitory/Instability RNA sequences) found for example, at nucleotides 414 to 631 in the gag region of HIV-1.

The guide RNA sequence can be a sense or anti-sense sequence. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. For example, Cas9 from *S. thermophilus* requires 5'-NNAGAA for CRISPR 1 and 5'-NGGNG for CRISPR3) and *Neiseria menigiditis* requires 5'-NNNNGATT). The specific sequence of the guide RNA may vary, but, regardless of the sequence, useful guide RNA sequences will be those that minimize off-target effects while achieving high efficiency and complete ablation of the genomically integrated HIV-1 provirus. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides. Useful selection methods identify regions having extremely low homology between the foreign viral genome and host cellular genome including endogenous retroviral DNA, include bioinformatic screening using 12-bp+NGG target-selection criteria to exclude off-target human transcriptome or (even rarely) untranslated-genomic sites; avoiding transcription factor binding sites within the HIV-1 LTR promoter (potentially conserved in the host genome); selection of LTR-A- and -B-directed, 30-bp gRNAs and also pre-crRNA system reflecting the original bacterial immune mechanism to enhance specificity/efficiency vs. 20-bp gRNA-, chimeric crRNA-tracRNA-based system and WGS, Sanger sequencing and SURVEYOR assay, to identify and exclude potential off-target effects.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs, for example any combination of sequences in U3, R, or U5. In some embodiments, combinations of LTR A, LTR B, LTR C and LTR D can be used. In some embodiments, combinations of any of the sequences LTR A (SEQ ID NO: 96), LTR B (SEQ ID NO: 121), LTR C (SEQ ID NO: 87), and LTR D (SEQ ID NO: 110), can be used. In some embodiments, any combinations of the sequences having the sequence of SEQ ID NOs: 79-111 and SEQ ID NOs: 111-141 can be used. When the compositions are administered in an expression vector, the guide RNAs can be encoded by a single vector. Alternatively, multiple vectors can be engineered to each include two or more different guide RNAs. Useful configurations will result in the excision of viral sequences between cleavage sites resulting in the ablation of HIV genome or HIV protein expression. Thus, the use of two or more different guide RNAs promotes excision of the viral sequences between the cleavage sites recognized by the CRISPR endonuclease. The excised region can vary in size from a single nucleotide to several thousand nucleotides. Exemplary excised regions are described in the examples.

When the compositions are administered as a nucleic acid or are contained within an expression vector, the CRISPR endonuclease can be encoded by the same nucleic acid or vector as the guide RNA sequences. Alternatively or in addition, the CRISPR endonuclease can be encoded in a physically separate nucleic acid from the guide RNA sequences or in a separate vector.

In some embodiments, the RNA molecules e.g. crRNA, tracrRNA, gRNA are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington D.C.). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyladenosine; N.sup.6N-methyladenosine; $N^6$,$N^6$-dimethyladenosine; $N^6$,2'-O-trimethyladenosine; 2-methylthio-$N^6$N-isopentenyladenosine; $N^6$-(cis-hydroxyisopentenyl)-adenosine; 2-methylthio-$N^6$-(cis-hydroxyisopentenyl)-adenosine; $N^6$-glycinylcarbamoyl) adenosine; $N^6$-threonylcarbamoyl adenosine; $N^6$-methyl-$N^6$-threonylcarbamoyl adenosine; 2-methylthio-$N^6$-methyl-$N^6$-threonylcarbamoyl adenosine; $N^6$-hydroxynorvalylcarbamoyl adenosine; 2-methylthio-$N^6$-hydroxnorvalylcarbamoyl adenosine; 2'-O-ribosyladenosine (phosphate); inosine; 2'O-methyl inosine; 1-methyl inosine; 1;2'-O-dimethyl inosine; 2'-O-methyl guanosine; 1-methyl guanosine; $N^2$-methyl guanosine; $N^2$,$N^2$-dimethyl guanosine; $N^2$,2'-O-dimethyl guanosine; $N^2$,$N^2$,2'-O-trimethyl guanosine; 2'-O-ribosyl guanosine (phosphate); 7-methyl guanosine; $N^2$;7-dimethyl guanosine; $N^2$; $N^2$;7-trimethyl guanosine; wyosine; methylwyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a naturally occurring Cas9 or a biologically active variant thereof and a guide RNA where in the guide RNA is complementary to a sequence in HIV.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of a Cas9-encoding DNA (in accordance with, for example, the formula above).

Two nucleic acids or the polypeptides they encode may be described as having a certain degree of identity to one another. For example, a Cas9 protein and a biologically active variant thereof may be described as exhibiting a certain degree of identity. Alignments may be assembled by locating short Cas9 sequences in the Protein Information Research (PIR) site, followed by analysis with the "short nearly identical sequences." Basic Local Alignment Search Tool (BLAST) algorithm on the NCBI website.

As used herein, the term "percent sequence identity" refers to the degree of identity between any given query sequence and a subject sequence. For example, a naturally occurring Cas9 can be the query sequence and a fragment of a Cas9 protein can be the subject sequence. Similarly, a fragment of a Cas9 protein can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pair wise alignment of nucleic acid sequences, the following default parameters are used: word size: 2; window size: 4; scoring method: percentage; number of top diagonals: 4; and gap penalty: 5. for multiple alignments of nucleic acid sequences, the following parameters are used: gap opening penalty: 10.0; gap extension penalty: 5.0; and weight transitions: yes. For fast pair wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express Cas9 and/or a guide RNA complementary to a target sequence in HIV. A recombinant nucleic acid construct comprises a nucleic acid encoding a Cas9 and/or a guide RNA complementary to a target sequence in HIV as described herein, operably linked to a regulatory region suitable for expressing the Cas9 and/or a guide RNA complementary to a target sequence in HIV in the cell. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for Cas9 can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2µ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Yeast expression systems can also be used. For example, the non-fusion pYES2 vector (XbaI, SphI, ShoI, NotI, GstXI, EcoRI, BstXI, BamH1, SacI, Kpn1, and HindIII cloning sites; Invitrogen) or the fusion pYESHisA, B, C (XbaI, SphI, ShoI, NotI, BstXI, EcoRI, BamH1, SacI, KpnI, and HindIII cloning sites, N-terminal peptide purified with ProBond resin and cleaved with enterokinase; Invitrogen), to mention just two, can be employed according to the invention. A yeast two-hybrid expression system can also be prepared in accordance with the invention.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; Bio Techniques, 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about $10^8$ to about $5\times10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Additional vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.: U.S.A.:*90 7603 (1993); Geller, A. I., et al., *Proc Natl. Acad. Sci USA:* 87:1149 (1990)], Adenovirus Vectors [LeGal LaSalle et al., *Science,* 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV) (Davis, et al., *Hum Gene Ther* 4:151 (1993)), the SV40 early promoter region, the herpes thymidine kinase promoter, the regulatory sequences of the metallothionein (MMT) gene, prokaryotic expression vectors such as the β-lactamase promoter, the tac promoter, promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Feigner and Holm, Bethesda Res. Lab. Focus, 11(2):21 (1989) and Maurer, R. A., Bethesda Res. Lab. Focus, 11(2):25 (1989).

Replication-defective recombinant adenoviral vectors, can be produced in accordance with known techniques. See, Quantin, et al., *Proc. Natl. Acad. Sci. USA,* 89:2581-2584 (1992); Stratford-Perricadet, et al., J. Clin. Invest., 90:626-630 (1992); and Rosenfeld, et al., Cell, 68:143-155 (1992).

Another delivery method is to use single stranded DNA producing vectors which can produce the expressed products intracellularly. See for example, Chen et al, *Bio Techniques,* 34: 167-171 (2003), which is incorporated herein, by reference, in its entirety.

Pharmaceutical Compositions

As described above, the compositions of the present invention can be prepared in a variety of ways known to one of ordinary skill in the art. Regardless of their original source or the manner in which they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment, e.g., the treatment of a subject having an HIV infection or at risk for contracting and HIV infection. When employed as pharmaceuticals, any of the nucleic acids and vectors can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, nucleic acids and vectors described herein in combination with one or more pharmaceutically acceptable carriers. We use the terms "pharmaceutically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are commonly latently infected reservoirs of HIV infection, for example, brain macrophages, microglia, astrocytes, and gut-associated lymphoid cells. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding the an isolated nucleic acid sequence comprising a sequence encoding a CRISPR-associated endonuclease and a guide RNA is operatively linked to a promoter or enhancer-promoter combination. Promoters and enhancers are described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol-modified (PEGylated) low molecular weight LPEI.

The nucleic acids and vectors may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments, the compositions may be formulated as a topical gel for blocking sexual transmission of HIV. The topical gel can be applied directly to the skin or mucous membranes of the male or female genital region prior to sexual activity. Alternatively or in addition the topical gel can be applied to the surface or contained within a male or female condom or diaphragm.

In some embodiments, the compositions can be formulated as a nanoparticle encapsulating a nucleic acid encoding Cas9 or a variant Cas9 and a guide RNA sequence complementary to a target HIV or vector comprising a nucleic acid encoding Cas9 and a guide RNA sequence complementary to a target HIV. Alternatively, the compositions can be formulated as a nanoparticle encapsulating a CRISPR-associated endonuclease polypeptide, e.g., Cas9 or a variant Cas9 and a guide RNA sequence complementary to a target.

The present formulations can encompass a vector encoding Cas9 and a guide RNA sequence complementary to a target HIV. The guide RNA sequence can include a sequence complementary to a single region, e.g. LTR A, B, C, or D or it can include any combination of sequences complementary to LTR A, B, C, and D. Alternatively the sequence encoding Cas9 and the sequence encoding the guide RNA sequence can be on separate vectors.

Methods of Treatment

The compositions disclosed herein are generally and variously useful for treatment of a subject having a retroviral infection, e.g., an HIV infection. We may refer to a subject, patient, or individual interchangeably. The methods are useful for targeting any HIV, for example, HIV-1, HIV-2, and any circulating recombinant form thereof. A subject is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has an HIV infection; and b) providing to the subject a composition comprising a nucleic acid encoding a CRISPR-associated nuclease, e.g., Cas9, and a guide RNA complementary to an HIV target sequence, e.g. an HIV LTR. A subject can be identified using standard clinical tests, for example, immunoassays to detect the presence of HIV antibodies or the HIV polypeptide p24 in the subject's serum, or through HIV nucleic acid amplification assays. An amount of such a composition provided to the subject that results in a complete resolution of the symptoms of the infection, a decrease in the severity of the symptoms of the infection, or a slowing of the infection's progression is considered a therapeutically effective amount. The present methods may also include a monitoring step to help optimize dosing and scheduling as well as predict outcome. In some methods of the present invention, one can first determine whether a patient has a latent HIV-1 infection, and then make a determination as to whether or not to treat the patient with one or more of the compositions described herein. Monitoring can also be used to detect the onset of drug resistance and to rapidly distinguish responsive patients from nonresponsive patients. In some embodiments, the methods can further include the step of determining the nucleic acid sequence of the particular HIV harbored by the patient and then designing the guide RNA to be complementary to those particular sequences. For example, one can determine the nucleic acid sequence of a subject's LTR U3, R or U5 region and then design one or more guide RNAs to be precisely complementary to the patient's sequences.

The compositions are also useful for the treatment, for example, as a prophylactic treatment, of a subject at risk for having a retroviral infection, e.g., an HIV infection. These methods can further include the steps of a) identifying a subject at risk for having an HIV infection; b) providing to the subject a composition comprising a nucleic acid encoding a CRISPR-associated nuclease, e.g., Cas9, and a guide RNA complementary to an HIV target sequence, e.g. an HIV LTR. A subject at risk for having an HIV infection can be, for example, any sexually active individual engaging in unprotected sex, i.e., engaging in sexual activity without the use of a condom; a sexually active individual having another sexually transmitted infection; an intravenous drug user; or an uncircumcised man. A subject at risk for having an HIV infection can be, for example, an individual whose occupation may bring him or her into contact with HIV-infected populations, e.g., healthcare workers or first responders. A subject at risk for having an HIV infection can be, for example, an inmate in a correctional setting or a sex worker, that is, an individual who uses sexual activity for income employment or nonmonetary items such as food, drugs, or shelter.

The compositions can also be administered to a pregnant or lactating woman having an HIV infection in order to reduce the likelihood of transmission of HIV from the mother to her offspring. A pregnant woman infected with HIV can pass the virus to her offspring transplacentally in utero, at the time of delivery through the birth canal or following delivery, through breast milk. The compositions disclosed herein can be administered to the HIV infected mother either perinatally, perinatally or postnatally during the breast-feeding period, or any combination of prenatal, perinatal, and postnatal administration. Compositions can be administered to the mother along with standard antiretroviral therapies as described below. In some embodiments, the compositions of the invention are also administered to the infant immediately following delivery and, in some embodiments, at intervals thereafter. The infant also can receive standard antiretroviral therapy.

The methods and compositions disclosed herein are useful for the treatment of retroviral infections. Exemplary retroviruses include human immunodeficiency viruses, e.g. HIV-1, HIV-2; simian immunodeficiency virus (SIV); feline immunodeficiency virus (FIV); bovine immunodeficiency virus (BIV); equine infectious anemia virus (EIAV); and caprine arthritis/encephalitis virus (CAEV). The methods disclosed herein can be applied to a wide range of species, e.g., humans, non-human primates (e.g., monkeys), horses or other livestock, dogs, cats, ferrets or other mammals kept as pets, rats, mice, or other laboratory animals.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of diseases or conditions as described herein.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

The compositions may also be administered with another therapeutic agent, for example, an anti-retroviral agent, used in HAART. Exemplary antiretroviral agents include reverse transcriptase inhibitors (e.g., nucleoside/nucleotide reverse transcriptase inhibitors, zidovudine, emtricitibine, lamivudine and tenofivir; and non-nucleoside reverse transcriptase inhibitors such as efavarenz, nevirapine, rilpivirine); protease inhibitors, e.g., tipiravir, darunavir, indinavir; entry inhibitors, e.g., maraviroc; fusion inhibitors, e.g., enfuviritide; or integrase inhibitors e.g., raltegrivir, dolutegravir. Exemplary antiretroviral agents can also include multi-class combination agents for example, combinations of emtricitabine, efavarenz, and tenofivir; combinations of emtricitabine; rilpivirine, and tenofivir; or combinations of elvitegravir, cobicistat, emtricitabine and tenofivir.

Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks. The therapeutic agents may be administered under a metronomic regimen, e.g., continuous low-doses of a therapeutic agent.

Dosage, toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As described, a therapeutically effective amount of a composition (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The compositions described herein are suitable for use in a variety of drug delivery systems described above. Additionally, in order to enhance the in vivo serum half-life of the administered compound, the compositions may be encapsulated, introduced into the lumen of liposomes, prepared as a colloid, or other conventional techniques may be employed which provide an extended serum half-life of the compositions. A variety of methods are available for preparing liposomes, as described in, e.g., Szoka, et al., U.S. Pat. Nos. 4,235,871, 4,501,728 and 4,837,028 each of which is incorporated herein by reference. Furthermore, one may administer the drug in a targeted drug delivery system, for example, in a liposome coated with a tissue-specific antibody. The liposomes will be targeted to and taken up selectively by the organ.

Also provided, are methods of inactivating a retrovirus, for example a lentivirus such as a human immunodeficiency virus, a simian immunodeficiency virus, a feline immunodeficiency virus, or a bovine immunodeficiency virus in a mammalian cell. The human immunodeficiency virus can be HIV-1 or HIV-2. The human immunodeficiency virus can be a chromosomally integrated provirus. The mammalian cell can be any cell type infected by HIV, including, but not limited to CD4+ lymphocytes, macrophages, fibroblasts, monocytes, T lymphocytes, B lymphocytes, natural killer cells, dendritic cells such as Langerhans cells and follicular dendritic cells, hematopoietic stem cells, endothelial cells, brain microglial cells, and gastrointestinal epithelial cells. Such cell types include those cell types that are typically infected during a primary infection, for example, a CD4+ lymphocyte, a macrophage, or a Langerhans cell, as well as those cell types that make up latent HIV reservoirs, i.e., a latently infected cell.

The methods can include exposing the cell to a composition comprising an isolated nucleic acid encoding a gene editing complex comprising a CRISPR-associated endonuclease and one or more guide RNAs wherein the guide RNA is complementary to a target nucleic acid sequence in the retrovirus. In a preferred embodiment, as previously described, the method of inactivating a proviral DNA integrated into the genome of a host cell latently infected with a retrovirus includes the steps of treating the host cell with a composition comprising a CRISPR-associated endonuclease, and two or more different guide RNAs (gRNAs), wherein each of the at least two gRNAs is complementary to a different target nucleic acid sequence in the proviral DNA; and inactivating the proviral DNA. The at least two gRNAs can be configured as a single sequence or as a combination of one or more different sequences, e.g., a multiplex configuration. Multiplex configurations can include combinations of two, three, four, five, six, seven, eight, nine, ten, or more different gRNAs, for example any combination of sequences in U3, R, or U5. In some embodiments, combinations of LTR A, LTR B, LTR C and LTR D can be used. In some embodiments, combinations of any of the sequences LTR A (SEQ ID NO: 96), LTR B (SEQ ID NO: 121), LTR C (SEQ ID NO: 87), and LTR D (SEQ ID NO: 110), can be used. In experiments described in the Examples, the use of two different gRNAs caused the excision of the viral sequences between the cleavage sites recognized by the CRISPR endonuclease. The excised region can include the entire HIV-1 genome. The treating step can take place in vivo, that is, the compositions can be administered directly to a subject having HIV infection. The methods are not so limited however, and the treating step can take place ex vivo. For example, a cell or plurality of cells, or a tissue explant, can be removed from a subject having an HIV infection and placed in culture, and then treated with a composition comprising a CRISPR-associated endonuclease and a guide RNA wherein the guide RNA is complementary to the nucleic acid sequence in the human immunodeficiency virus. As described above, the composition can be a nucleic acid encoding a CRISPR-associated endonuclease and a guide RNA wherein the guide RNA is complementary to the nucleic acid sequence in the human immunodeficiency virus; an expression vector comprising the nucleic acid sequence; or a pharmaceutical composition comprising a nucleic acid encoding a CRISPR-associated endonuclease and a guide RNA wherein the guide RNA is complementary to the nucleic acid sequence in the human immunodeficiency virus; or an expression vector comprising the nucleic acid sequence. In some embodiments, the gene editing complex can comprise a CRISPR-associated endonuclease polypeptide and a guide RNA wherein the guide RNA is complementary to the nucleic acid sequence in the human immunodeficiency virus.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

Standard methods, for example, immunoassays to detect the CRISPR-associated endonuclease, or nucleic acid-based assays such as PCR to detect the gRNA, can be used to confirm that the complex has been taken up and expressed by the cell into which it has been introduced. The engineered cells can then be reintroduced into the subject from whom they were derived as described below.

The gene editing complex comprises a CRISPR-associated nuclease, e.g., Cas9, and a guide RNA complementary to the retroviral target sequence, for example, an HIV target sequence. The gene editing complex can introduce various mutations into the proviral DNA. The mechanism by which such mutations inactivate the virus can vary, for example the mutation can affect proviral replication, viral gene expression or proviral excision. The mutations may be located in regulatory sequences or structural gene sequences and result in defective production of HIV. The mutation can comprise a deletion. The size of the deletion can vary from a single nucleotide base pair to about 10,000 base pairs. In some embodiments, the deletion can include all or substantially all of the proviral sequence. In some embodiments the deletion can include the entire proviral sequence. The mutation can comprise an insertion; that is the addition of one or more nucleotide base pairs to the pro-viral sequence. The size of the inserted sequence also may vary, for example from about one base pair to about 300 nucleotide base pairs. The mutation can comprise a point mutation, that is, the replacement of a single nucleotide with another nucleotide. Useful point mutations are those that have functional consequences, for example, mutations that result in the conversion of an amino acid codon into a termination codon or that result in the production of a nonfunctional protein.

In exemplary multiplex methods for inactivating proviral DNA integrated into the genome of a host cell, as demonstrated in Examples 2-5, two different gRNA sequences are deployed, with each gRNA sequence targeting a different site in the proviral DNA. That is, the methods include the steps of exposing the host cell to a composition including an isolated nucleic acid encoding a CRISPR-associated endonuclease; an isolated nucleic acid sequence encoding a first gRNA having a first spacer sequence that is complementary to a first target protospacer sequence in a proviral DNA; and an isolated nucleic acid encoding a second gRNA having a second spacer sequence that is complementary to a second target protospacer sequence in the proviral DNA; expressing in the host cell the CRISPR-associated endonuclease, the first gRNA, and the second gRNA; assembling, in the host cell, a first gene editing complex including the CRISPR-associated endonuclease and the first gRNA; and a second gene editing complex including the CRISPR-associated endonuclease and the second gRNA; directing the first gene editing complex to the first target protospacer sequence by complementary base pairing between the first spacer sequence and the first target protospacer sequence; directing the second gene editing complex to the second target protospacer sequence by complementary base pairing between the second spacer sequence and the second target protospacer sequence; cleaving the proviral DNA at the first target protospacer sequence with the CRISPR-associated endonuclease; cleaving the proviral DNA at the second target protospacer sequence with the CRISPR-associated endonuclease; and inducing at least one mutation in the proviral DNA. The same multiplex method is readily incorporated into methods for treating a subject having a human immunodeficiency virus, and for reducing the risk of a human immunodeficiency virus infection. It will be understood that the term "composition" can include not only a mixture of components, but also separate components that are not necessarily administered simultaneously. As a non-limiting example, a composition according to the present invention can include separate component preparations of nucleic acid sequences encoding a Cas9 nuclease, a first gRNA, and a second gRNA, with each component being administered sequentially in an infusion, during a time frame that results in a host cell being exposed to all three components.

In other embodiments, the compositions comprise a cell which has been transformed or transfected with one or more Cas/gRNA vectors. In some embodiments, the methods of the invention can be applied ex vivo. That is, a subject's cells can be removed from the body and treated with the compositions in culture to excise HIV sequences and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

The gRNA expression cassette can be easily delivered to a subject by methods known in the art, for example, methods which deliver siRNA. In some aspects, the Cas may be a fragment wherein the active domains of the Cas molecule are included, thereby cutting down on the size of the molecule. Thus, the, Cas9/gRNA molecules can be used clinically, similar to the approaches taken by current gene therapy. In particular, a Cas9/multiplex gRNA stable expression stem cell or iPS cells for cell transplantation therapy as well as HIV-1 vaccination will be developed for use in subjects.

Transduced cells are prepared for reinfusion according to established methods. After a period of about 2-4 weeks in culture, the cells may number between $1\times10^6$ and $1\times10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

Articles of Manufacture

The compositions described herein can be packaged in suitable containers labeled, for example, for use as a therapy to treat a subject having a retroviral infection, for example, an HIV infection or a subject at for contracting a retroviral infection, for example, an HIV infection. The containers can include a composition comprising a nucleic acid sequence encoding a CRISPR-associated endonuclease, for example, a Cas9 endonuclease, and a guide RNA complementary to a target sequence in a human immunodeficiency virus, or a vector encoding that nucleic acid, and one or more of a suitable stabilizer, carrier molecule, flavoring, and/or the like, as appropriate for the intended use. Accordingly, packaged products (e.g., sterile containers containing one or more of the compositions described herein and packaged for storage, shipment, or sale at concentrated or ready-to-use concentrations) and kits, including at least one composition of the invention, e.g., a nucleic acid sequence encoding a CRISPR-associated endonuclease, for example, a Cas9 endonuclease, and a guide RNA complementary to a target sequence in a human immunodeficiency virus, or a vector encoding that nucleic acid and instructions for use, are also within the scope of the invention. A product can include a container (e.g., a vial, jar, bottle, bag, or the like) containing one or more compositions of the invention. In addition, an article of manufacture further may include, for example, packaging materials, instructions for use, syringes, delivery devices, buffers or other control reagents for treating or monitoring the condition for which prophylaxis or treatment is required.

In some embodiments, the kits can include one or more additional antiretroviral agents, for example, a reverse transcriptase inhibitor, a protease inhibitor or an entry inhibitor. The additional agents can be packaged together in the same container as a nucleic acid sequence encoding a CRISPR-associated endonuclease, for example, a Cas9 endonuclease, and a guide RNA complementary to a target sequence in a human immunodeficiency virus, or a vector encoding that nucleic acid or they can be packaged separately. The nucleic acid sequence encoding a CRISPR-associated endonuclease, for example, a Cas9 endonuclease, and a guide RNA complementary to a target sequence in a human immunodeficiency virus, or a vector encoding that nucleic acid and the additional agent may be combined just before use or administered separately.

The product may also include a legend (e.g., a printed label or insert or other medium describing the product's use (e.g., an audio- or videotape)). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents and/or an additional therapeutic agent. Alternatively, the compositions can be provided in a concentrated form with a diluent and instructions for dilution.

Example 1: Materials and Methods

Plasmid Preparation:

Vectors containing human Cas9 and gRNA expression cassette, pX260, and pX330 (Addgene) were utilized to create various constructs, LTR-A, B, C, and D.

Cell Culture and Stable Cell Lines:

TZM-b1 reporter and U1 cell lines were obtained from the NIH AIDS Reagent Program and CHME5 microglial cells are known in the art.

Immunohistochemistry and Western Blot:

Standard methods for immunocytochemical observation of the cells and evaluation of protein expression by Western blot were utilized.

Firefly-Luciferase Assay:

Cells were lysed 24 h post-treatment using Passive Lysis Buffer (Promega) and assayed with a Luciferase Reporter Gene Assay kit (Promega) according to the manufacturer's protocol. Luciferase activity was normalized to the number of cells determined by a parallel MTT assay (VYBRANT®, Invitrogen)

p24 ELISA:

After infection or reactivation, the levels of HIV-1 viral load in the supernatants were quantified by p24 Gag ELISA (Advanced BioScience Laboratories, Inc) following the manufacturer's protocol. To assess cell viability upon treatments, MTT assay was performed in parallel according to the manufacturer's manual (VYBRANT®, Invitrogen).

EGFP Flow Cytometry:

Cells were trypsinized, washed with PBS and fixed in 2% paraformaldehyde for 10 min at room temperature, then washed twice with PBS and analyzed using a GUAVA® EasyCyte Mini flow cytometer (Guava Technologies).

HIV-1 Reporter Virus Preparation and Infections:

HEK293T cells were transfected using LIPOFECTAMINE® 2000 reagent (Invitrogen) with pNL4-3-ΔE-EGFP (NIH AIDS Research and Reference Reagent Program). After 48 h, the supernatant was collected, 0.45 µm filtered and tittered in HeLa cells using EGFP as an infection marker. For viral infection, stable Cas9/gRNA TZM-bl cells were incubated 2 h with diluted viral stock, and then washed twice with PBS. At 2 and 4 d post-infection, cells were collected, fixed and analyzed by flow cytometry for EGFP expression, or genomic DNA purification was performed for PCR and whole genome sequencing.

Genomic DNA Amplification, PCR, TA-Cloning, and Sanger Sequencing, GenomeWalker Link PCR:

Standard methods for DNA manipulation for cloning and sequencing were utilized. For identification of the integration sites of HIV-1, we utilized Lenti-XTM integration site analysis kit was used.

Surveyor Assay:

The presence of mutations in PCR products was examined using a SURVEYOR Mutation Detection Kit (Transgenomic) according to the protocol from the manufacturer. Briefly heterogeneous PCR product was denatured for 10 min in 95° C. and hybridized by gradual cooling using a thermocycler. Next, 300 ng of hybridized DNA (9 µl) was subjected to digestion with 0.25 µl of SURVEYOR Nuclease in the presence of 0.25 µl SURVEYOR Enhancer S and 15 mM $MgCl_2$ for 4 h at 42° C. Then Stop Solution was added and samples were resolved in 2% agarose gel together with equal amounts of undigested PCR product controls.

Some PCR products were used for restriction fragment length polymorphism analysis. Equal amounts of the PCR products were digested with BsaJI. Digested DNA was separated on an ethidium bromide-contained agarose gel (2%). For sequencing, PCR products were cloned using a TA Cloning® Kit Dual Promoter with pCRTMII vector (Invitrogen). The insert was confirmed by digestion with EcoRI and positive clones were sent to Genewiz for Sanger sequencing.

Selection of LTR Target Sites, Whole Genome Sequencing and Bioinformatics and Statistical Analysis.

We utilized Jack Lin's CRISPR/Cas9 gRNA finder tool for initial identification of potential target sites within the LTR.

Plasmid Preparation.

DNA segment expressing LTR-A or LTR-B for pre-crRNA was cloned into the pX260 vector that contains the puromycin selection gene (Addgene, plasmid #42229). DNA segments expressing LTR-C or LTR-D for the chimeric crRNA-tracrRNA were cloned into the pX330 vector (Addgene, plasmid #42230). Both vectors contain a humanized Cas9 coding sequence driven by a CAG promoter and a gRNA expression cassette driven by a human U6 promoter. The vectors were digested with BbsI and treated with Antarctic Phosphatase, and the linearized vector was purified with a Quick nucleotide removal kit (Qiagen). A pair of oligonucleotides for each targeting site (FIG. 14, AlphaDNA) was annealed, phosphorylated, and ligated to the linearized vector. The gRNA expression cassette was sequenced with U6 sequencing primer (FIG. 14) in GENEWIZ. For pX330 vectors, we designed a pair of universal PCR primers with overhang digestion sites (FIG. 14) that can tease out the gRNA expression cassette (U6-gRNA-crRNA-stem-tracrRNA) for direct transfection or subcloning to other vectors.

Cell Culture.

TZM-bl reporter cell line from Dr John C. Kappes, Dr Xiaoyun Wu and Tranzyme Inc, U1/Hiv-1 cell line from Dr. Thomas Folks and J-Lat full length clone from Dr. Eric Verdin were obtained through the NIH AIDS Reagent Program, Division of AIDS, NIAID, NIH. CHME5/HIV fetal microglia cell line were generated as previously described. TZM-bl and CHME5 cells were cultured in Dulbecco's minimal essential medium high glucose supplemented with 10% heat-inactivated fetal bovine serum (FBS) and 1% penicillin/streptomycin. U1 and J-Lat cells were cultured in RPMI 1640 containing 2.0 mM L-glutamine, 10% FBS and 1% penicillin/streptomycin.

Stable Cell Lines and Subcloning.

TZM-bl or CHME5/HIV cells were seeded in 6-well plates at 1.5×105 cells/well and transfected using LIPOFECTAMINE® 2000 reagent (Invitrogen) with 1 µg of pX260 (for LTR-A and B) or 1 µg/0.1 µg of pX330/pX260 (for LTR-C and D) plasmids. Next day, cells were transferred into 100-mm dishes and incubated with growth medium containing 1 µg/ml of puromycin (Sigma). Two weeks later, surviving cell colonies were isolated using cloning cylinders (Corning). U1 cells (1.5×105) were electroporated with 1 µg of DNA using 10 µl tip, 3×10 ms 1400 V impulses at The Neon™ Transfection System (Invitrogen). Cells were selected with 0.5 µg/ml of puromycin for two weeks. The stable clones were subcultured using a limited dilution method in 96-well plates and single cell-derived subclones were maintained for further studies.

Immunocytochemistry and Western Blot.

The Cas9/gRNA stable expression TZM-bl cells were cultured in 8-well chamber slides for 2 days and fixed for 10 min in 4% paraformaldehyde/PBS. After three rinses, the cells were treated with 0.5% Triton X-100/PBS for 20 min and blocked in 10% donkey serum for 1 h. Cells were incubated overnight at 4° C. with mouse anti-Flag M2 primary antibody (1:500, Sigma). After rinsing three times, cells were incubated for 1 h with donkey anti-mouse Alexa-Fluor-594 secondary antibodies, and incubated with Hoechst 33258 for 5 min. After three rinses with PBS, the cells were coverslipped with anti-fading aqueous mounting media (Biomeda) and analyzed under a Leica DMI6000B fluorescence microscope.

TZM-bl cells cultured in 6-well plate were solubilized in 200 µl of Triton X-100-based lysis buffer containing 20 mM Tris-HCl (pH 7.4), 1% Triton X-100, 5 mM ethylenediaminetetraacetic acid, 5 mM dithiothreitol, 150 mM NaCl, 1 mM phenylmethylsulfonyl fluoride, 1× nuclear extraction proteinase inhibitor cocktail (Cayman Chemical, Ann Arbor, Mich.), 1 mM sodium orthovanadate and 30 mM NaF. Cell lysates were rotated at 4° C. for 30 min. Nuclear and cellular debris was cleared by centrifugation at 20,000 g for 20 min at 4° C. Equal amounts of lysate proteins (20 µg) were denatured by boiling for 5 min in sodium dodecyl sulphate (SDS) sample buffer, fractionated by SDS-polyacrylamide gel electrophoresis in tris-glycine buffer, and transferred to nitrocellulose membrane (BioRad). The SeeBlue prestained standards (Invitrogen) were used as a molecular weight reference. Blots were blocked in 5% BSA/tris-buffered saline (pH 7.6) plus 0.1% Tween-20 (TBS-T) for 1 h and then incubated overnight at 4° C. with mouse anti-Flag M2 monoclonal antibody (1:1000, Sigma) or mouse anti-GAPDH monoclonal antibody (1:3000, Santa Cruz Biotechnology). After washing with TBS-T, the blots were incubated with IRDye 680LT-conjugated anti-mouse antibody for 1 h at room temperature. Membranes were scanned and analyzed using an Odyssey Infrared Imaging System (LI-COR Biosciences).

Firefly-Luciferase Assay.

Cells were lysed 24 h post-treatment using Passive Lysis Buffer (Promega) and assayed with a Luciferase Reporter Gene Assay kit (Promega) according to the protocol of the manufacturer. Luciferase activity was normalized to the number of cells determined by parallel MTT assay (VYBRANT®, Invitrogen).

p24 ELISA

After infection or reactivation, the HIV-1 viral load levels in the supernatants were quantified by p24 Gag ELISA (Advanced BioScience Laboratories, Inc) following the manufacturer's protocol. To assess the cell viability upon treatments, MTT assay was performed in parallel according to the manufacturer's protocol (VYBRANT®, Invitrogen).

EGFP Flow Cytometry.

Cells were trypsinized, washed with PBS and fixed in 2% paraformaldehyde for 10 min at room temperature, then washed twice with PBS and analyzed using a GUAVA® EasyCyte Mini flow cytometer (Guava Technologies).

Hiv-1 Reporter Virus Preparation and Infections.

HEK293T cells were transfected using LIPOFECTAMINE® 2000 reagent (Invitrogen) with pNL4-3-ΔE-EGFP, SF162 and JRFL (NIH AIDS Research and Reference Reagent Program). For pseudotyped pNL4-3-ΔE-EGFP, the VSVG vector was cotransfected. After 48 h, the supernatant was collected, 0.45 µm filtered and tittered in HeLa cells using expressed EGFP as an infection marker. For viral infection, stable Cas9/gRNA TZM-bl cells were incubated 2 h with a diluted viral stock, and washed twice with PBS. At 2 and 4 days post-infection, cells were collected, fixed and analyzed by flow cytometry for EGFP expression, or genomic DNA purification was performed for PCR and whole genome sequencing.

Genomic DNA Purification, PCR, TA-Cloning and Sanger Sequencing.

Genomic DNA was isolated from cells using an ArchivePure DNA cell/tissue purification kit (5PRIME) according to the protocol recommended by the manufacturer. One hundred ng of extracted DNA were subjected to PCR using a high-fidelity FailSafe PCR kit (Epicentre) using primers listed in FIG. 14. Three steps of standard PCR were carried out for 30 cycles with 55° C. annealing and 72° C. extension. The products were resolved in 2% agarose gel. The bands of interest were gel-purified and cloned into pCRII T-A vector (Invitrogen), and the nucleotide sequence of individual clones was determined by sequencing at Genewiz using universal T7 and/or SP6 primers.

Conventional and Real-Time Reverse Transcription (RT)-PCR.

For total RNA extraction, cells were processed with an RNeasy Mini kit (Qiagen) as per manufacturer's instructions. The potentially residual genomic DNA was removed through on-column DNase digestion with an RNase-Free DNase Set (Qiagen). One µg of RNA for each sample was reversely transcribed into cDNAs using random hexanucleotide primers with a High Capacity cDNA Reverse Transcription Kit (Invitrogen, Grand Island, N.Y.). Conventional PCR was performed using a standard protocol. Quantitative PCR (qPCR) analyses were carried out in a LightCycler480 (Roche) using an SYBR® Green PCR Master Mix Kit (Applied Biosystems). The RT reactions were diluted to 5 ng of total RNA per micro-liter of reactions and 2 µl was used in a 20-µl PCR reaction. For qPCR analysis of HIV-1 proviruses, 50 ng of genomic DNA were used. The primers were synthesized in AlphaDNA and shown in FIG. 14. The primers for human housekeeping genes GAPDH and RPL13A were obtained from RealTimePrimers (Elkins Park, Pa.). Each sample was tested in triplicate. Cycle threshold (Ct) values were obtained graphically for the target genes and house-keeping genes. The difference in Ct values between the housekeeping gene and target gene was represented as ΔCt values. The ΔΔCt values were obtained by subtracting the ΔCt values of control samples from those of experimental samples. Relative fold or percentage change was calculated as 2-ΔΔCt. In some cases, absolute quantification was performed using the pNL4-3-ΔE-EGFP plasmid spiked in human genomic DNA as a standard. The number of HIV-1 viral copies was calculated based on standard curve after normalization with housekeeping gene.

GENOMEWALKER™ Link PCR and Long-Range PCR.

The integration sites of HIV-1 in host cells were identified using a Lenti-X™ Integration Site Analysis kit (Clontech) following the manufacturer's instruction. Briefly, high quality genomic DNAs were extracted from U1 cells using a NUCLEOSPIN® Tissue kit (Clontech). To construct the viral integration libraries, each genomic DNA sample was digested with blunt-end-generating digestion enzymes Dro I, Ssp I or HpaI separately overnight at 37° C. The digestion efficiency was verified by electrophoresis on 0.6% agarose. The digested DNA was purified using a NUCLEOSPIN® Gel and PCR Clean-Up kit followed by ligation of the digested genomic DNA fragments to GENOMEWALKER™ Adaptor at 16° C. overnight. The ligation reaction was stopped by incubation at 70° C. for 5 min and diluted 5 times with TE buffer. The primary PCR was performed on the DNA segments with adaptor primer 1 (AP1) and LTR-specific primer 1 (LSP1) using Advantage 2 Polymerase Mix followed by a secondary (nested) PCR using AP2 and LSP2 primers (FIG. 14). The secondary PCR products were separated on 1.5% ethidium bromide-containing agarose gel. The major bands were gel-purified and cloned into pCRII T-A vector (Invitrogen), and the nucleotide sequence of individual clones was determined by sequencing at Genewiz using universal T7 and SP6 primers. The sequence reads were analyzed by NCBI BLAST searching. Two integration sites of HIV-1 in U1 cells were identified in chromosomes X and 2. A pair of primers covering each integration site (FIG. 14) was synthesized in AlphaDNA. Long-range PCR using the U1 genomic DNA was performed with a PHUSION® High-Fidelity PCR kit (New England Biolabs) following the manufacturer's protocol. The PCR products were visualized on 1% agarose gel and validated by Sanger sequencing.

Surveyor Assay.

The presence of mutations in PCR products was tested using a SURVEYOR Mutation Detection Kit (Transgenomic) according to the protocol of the manufacturer. Briefly heterogeneous PCR products were denatured for 10 min in 95° C. and hybridized by gradual cooling using a thermocycler. Next 300 ng of hybridized DNA (9 ul) was subjected to digestion with 0.25 µl of SURVEYOR Nuclease in the presence of 0.25 µl SURVEYOR Enhancer S and 15 mM $MgCl_2$ for 4 h at 42° C. Then Stop Solution was added and samples were resolved in 2% agarose gel together with equal amounts of undigested PCR products.

Some PCR products were used for restriction fragment length polymorphism analysis. Equal amount of PCR products were digested with BsaJI. Digested DNA was separated on an ethidium bromide-contained agarose gel (2%). For sequencing, PCR products were cloned using a TA Cloning® Kit Dual Promoter with pCR™II vector (Invitrogen). The insert was confirmed by digestion with EcoRI and positive clones were sent to Genwiz for Sanger sequencing.

Selection of LTR Target Sites and Prediction of Potential Off-Target Sites.

For initial studies, we obtained the LTR promoter sequence (−411 to −10) of the integrated lentiviral LTR-luciferase reporter by TA-cloning sequencing of PCR products from the genome of human TZM-bl cells because of potential mutation of LTR during passaging. This promoter sequence has 100% match to the 5'-LTR of pHR'-CMV-LacZ lentiviral vector (AF105229). Thus, sense and antisense sequences of the full-length pHR' 5'-LTR (634 bp) were utilized to search for Cas9/gRNA target sites containing 20 bp gRNA targeting sequence plus the PAM sequence (NRG) using Jack Lin's CRISPR/Cas9 gRNA finder tool. The number of potential off-targets with exact match was predicted by blasting each gRNA targeting sequence plus NRG (AGG, TGG, GGG and CGG; AAG, TAG, GAG, CAG) against all available human genomic and transcript sequences using the NCBI/blastn suite with E-value cutoff 1,000 and word size 7. After pressing Control+F, copy/paste the target sequence (1-23 through 9-23 nucleotides) and find the number of genomic targets with 100% match to the target sequence. The number of off-targets for each search was divided by 3 because of repeated genome library.

Whole Genome Sequencing and Bioinformatics Analysis.

The control subclone C1 and experimental subclone AB7 of TZM-bl cells were validated for target cut efficiency and functional suppression of the LTR-luciferase reporter. The genomic DNA was isolated with NUCLEOSPIN® Tissue kit (Clontech). The DNA samples were submitted to the NextGen sequencing facility at Temple University Fox Chase Cancer Center. Duplicated genomic DNA libraries were prepared from each subclone using a NEBNext Ultra DNA Library Prep Kit for Illumina (New England Biolab) following the manufacturer's instruction. All libraries were sequenced with paired-end 141-bp reads in two Illumina Rapid Run flowcells on HiSeq 2500 instrument (Illumina). Demultiplexed read data from the sequenced libraries were sent to AccuraScience, LLC for professional bioinformatics analysis. Briefly, the raw reads were mapped against human genome (hg19) and HIV-1 genome by using Bowtie2. A genomic analysis toolkit (GATK, version 2.8.1) was used for the duplicated read removal, local alignment, base quality recalibration and indel calling. The confidence scores 10 and 30 were the thresholds for low quality (LowQual) and high confidence calling (PASS). The potential off-target sites of LTR-A and LTR-B with various mismatches were predicted by NCBI/blastn suite as described above and by CRISPR Design Tool. All the potential gRNA target sites (FIG. 15) were used to map the ±300 bp regions around each indel identified by GATK. The locations of the overlapped regions in the human genome and HIV-1 genome were compared between the control C1 and experimental AB7.

Statistical Analysis.

The quantitative data represented mean±standard deviation from 3-5 independent experiments, and were evaluated by Student's t-test or ANOVA and Newman-Keuls multiple comparison test. A p value that is <0.05 or 0.01 was considered as a statistically significant difference.

Example 2: Cas9/LTR-gRNA Suppresses HIV-1 Reporter Virus Production in CHME5 Microglial Cells Latently Infected with HIV-1

Figure 6C:
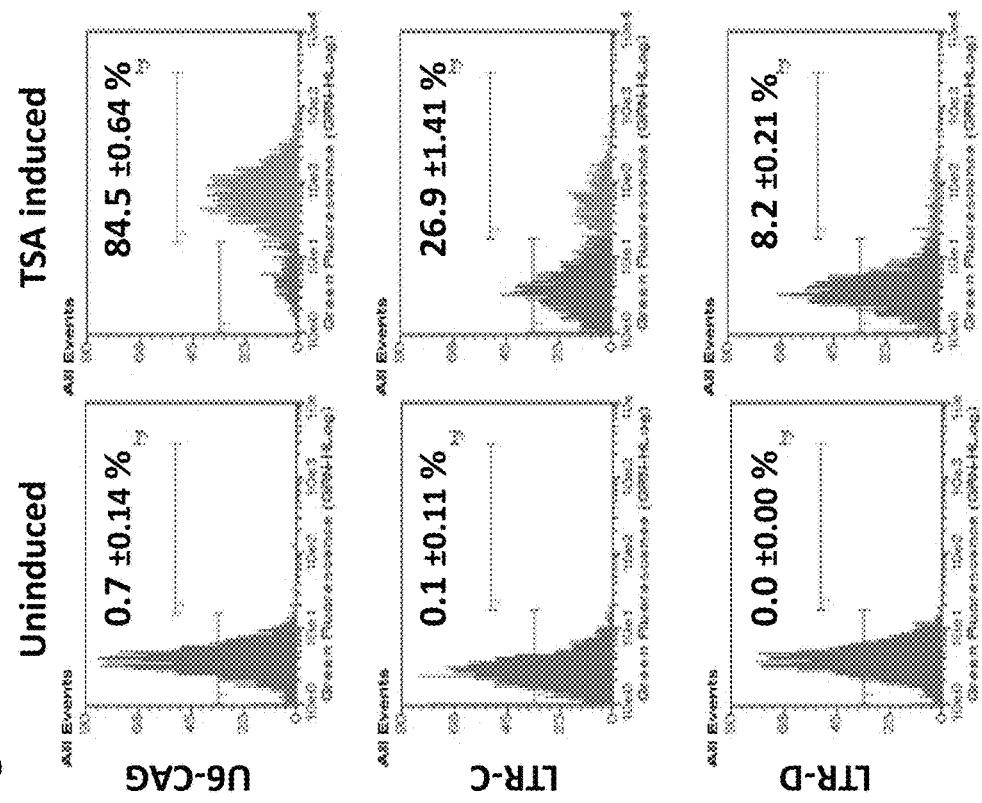
FIGS. 6A-6C show that LTR-C and LTR-D remarkably suppress TSA-induced reactivation of latent pNL4-3-ΔGag-d2EGFP virus in CHME5 microglia cells. (6A) Diagram schematically showing pNL4-3-ΔGag-d2EGFP vector containing Tat, Rev, Env, Vpu, and Nef with the reporter gene d2EGFP. (6B) The SURVEYOR assay showing indel mutations in the on-target LTR genome of Cas9/LTR-D but not Cas9/LTR-C transfected cells. (6C) Representative gating diagram of EGFP flow cytometry showing a dramatic reduction in TSA-induced reactivation of latent pNL4-3-ΔGag-d2EGFP reporter viruses by stable expression of Cas9/LTR-C or LTR-D as compared with empty U6-driven gRNA expression vector (U6-CAG).
Figure 6A:
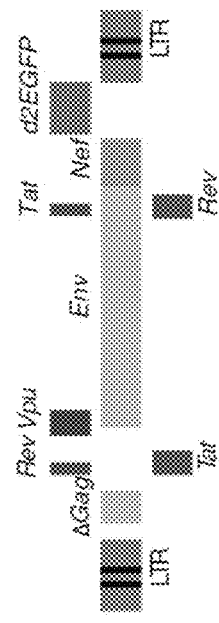
Figure 6B:
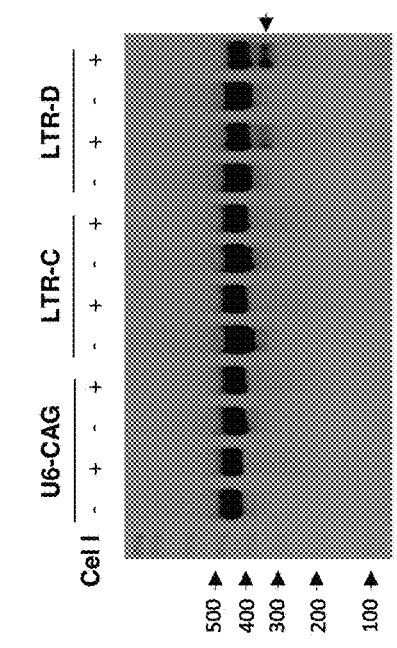
Figure 7A:
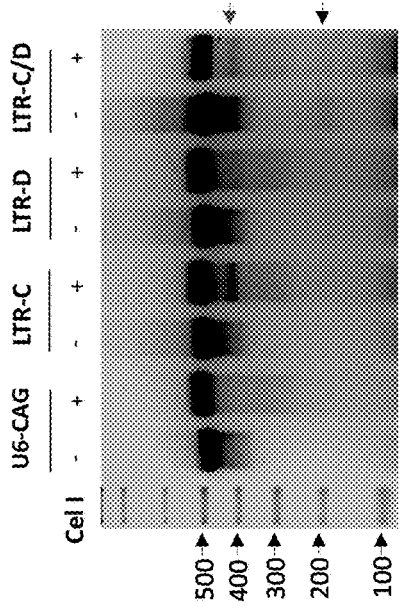
Figure 7B:
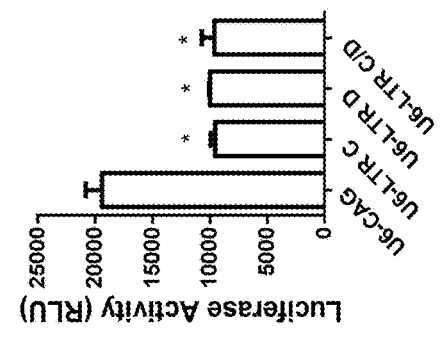
Figure 7C:

We assessed the ability of HIV-1-directed guide RNAs (gRNAs) to abrogate LTR transcriptional activity and eradicate proviral DNA from the genomes of latently-infected myeloid cells that serve as HIV-1 reservoirs in the brain, a particularly intractable target population. Our strategy was focused on targeting the HIV-1 LTR promoter U3 region. By bioinformatic screening and efficiency/off-target prediction, we identified four gRNA targets (protospacers; LTRs A-D) that avoid conserved transcription factor binding sites, minimizing the likelihood of altering host gene expression (FIGS. 5 and 13). We inserted DNA fragments complementary to gRNAs A-D into a humanized Cas9 expression vector (A/B in pX260; C/D in pX330) and tested their individual and combined abilities to alter the integrated HIV-1 genome activity. We first utilized the microglial cell line CHME5, which harbors integrated copies of a single round HIV-1 vector that includes the 5' and 3' LTRs, and a gene encoding an enhanced green fluorescent protein (EGFP) reporter replacing Gag (pNL4-3-ΔGag-d2EGFP). Treating CHME5 cells with trichostatin A (TSA), a histone deacetylase inhibitor, reactivates transcription from the majority of the integrated proviruses and leads to expression of EGFP and the remaining HIV-1 proteome. Expressing of gRNAs plus Cas9 markedly decreased the fraction of TSA-induced EGFP-positive CHME5 cells (FIGS. 1A and 6). We detected insertion/deletion gene mutations (indels) for LTRs A-D (FIGS. 1B and 6B) using a Cel I nuclease-based heteroduplex-specific SURVEYOR assay. Similarly, expressing gRNAs targeting LTRs C and D in HeLa-derived TZM-bl cells, that contain stably incorporated HIV-1 LTR copies driving a firefly-luciferase reporter gene, suppressed viral promoter activity (FIG. 7A), and elicited indels within the LTR U3 region (FIG. 7B-D) demonstrated by SURVEYOR and Sanger sequencing. Moreover, the combined expression of LTR C/D-targeting gRNAs in these cells caused excision of the predicted 302-bp viral DNA sequence, and emergence of the residual 194-bp fragment (FIG. 7E-F).

Figure 1H:
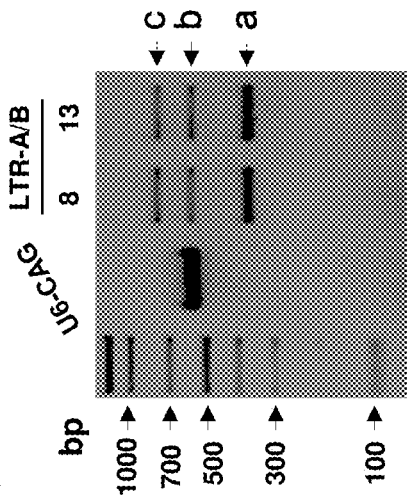
Figure 1E:
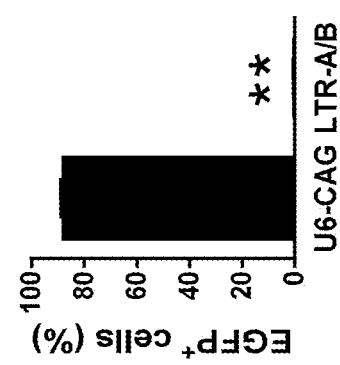
Figure 1G:
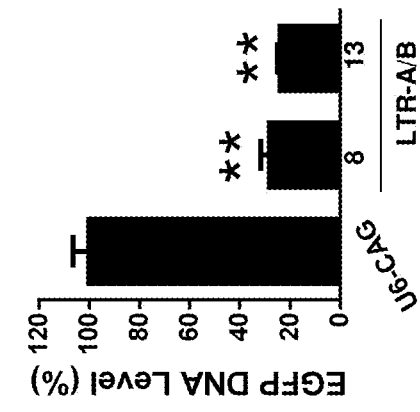

Multiplex expression of LTR-A/B gRNAs in mixed clonal CHME5 cells caused deletion of a 190-bp fragment between A and B target sites and led to indels to various extents (FIG. 1C-D). Among >20 puromycin-selected stable subclones, we found cell populations with complete blockade of TSA-induced HIV-1 proviral reactivation determined by flow cytometry for EGFP (FIG. 1E). PCR-based analysis for EGFP and HIV-1 Rev response element (RRE) in the proviral genome validated the eradication of HIV-1 genome (FIG. 1F, G). Furthermore, sequencing of the PCR products revealed the entire 5'-3' LTR-spanning viral genome was deleted, yielding a 351-bp fragment via a 190-bp excision between cleavage sites A and B (FIGS. 1G and 8), and a 682-bp fragment with a 175-bp insertion and a 27-bp deletion at the LTR-A and -B sites respectively (FIG. 8C). The residual HIV-1 genome (FIG. 1F-H) may reflect the presence of trace Cas9/gRNA-negative cells. These results indicate that LTR-targeting Cas9/gRNAs A/B eradicates the HIV-1 genome and blocks its reactivation in latently infected microglial cells.

Figure 2A:
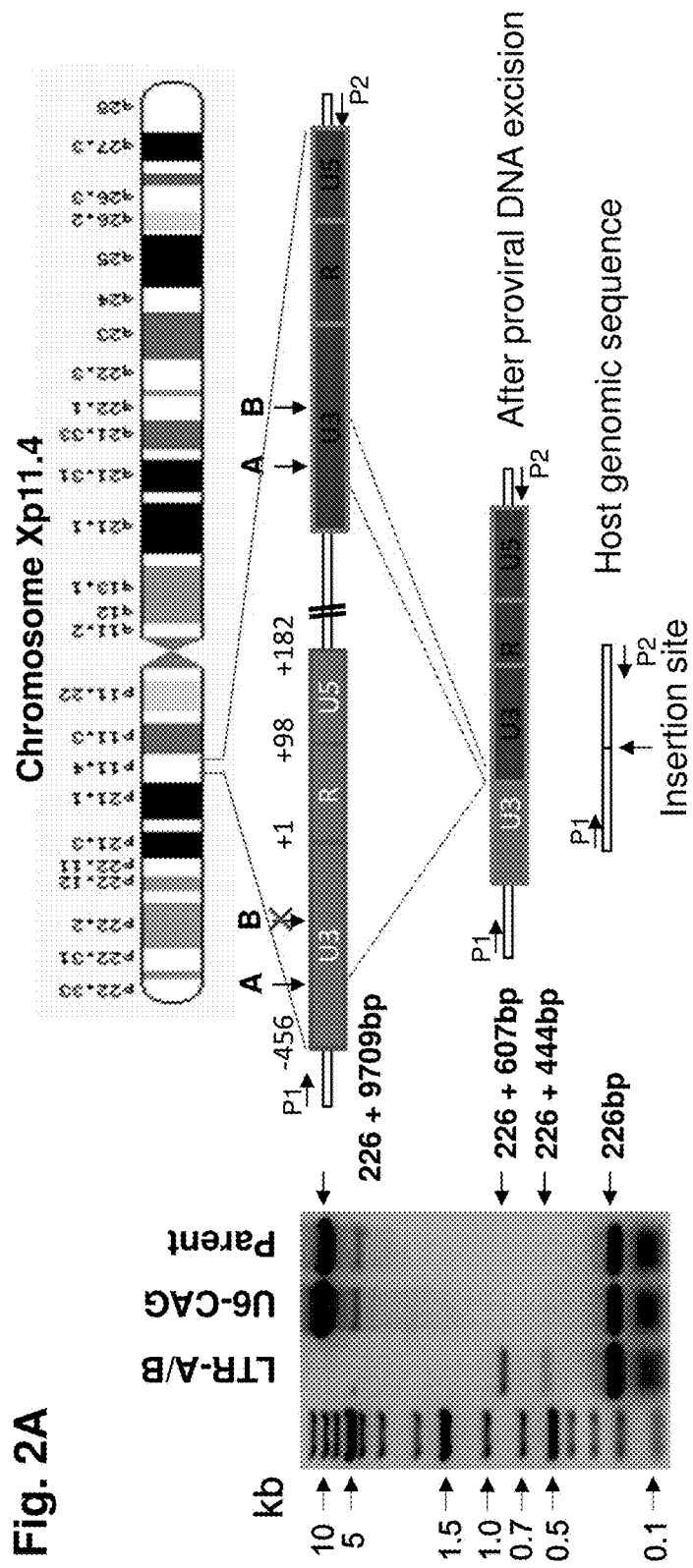
FIGS. 2A-2C show that Cas9/LTR-gRNA efficiently eradicates latent HIV-1 virus from U1 monocytic cells. (2A) Right, diagram showing excision of HIV-1 entire genome in chromosome Xp11.4. HIV-1 integration sites were identified using a Genome-Walker link PCR kit. Left, analysis of PCR amplicon lengths using a primer pair (P1/P2) targeting chromosome X integration site-flanking sequence reveals elimination of the entire HIV-1 genome (9709-bp), leaving two fragments (833- and 670-bp). (2B) TA cloning and sequencing of the LTR fragment (833-bp) showing the host genomic sequence (small letters, 226-bp) and the partial sequences (634−27=607 bp) of 5'-LTR (underlined using dashes) and 3'-LTR (first underlined section) with a 27-bp deletion around the LTR-A targeting site (second underlined section). Bottom, two indel alleles identified from 15 sequenced clonal amplicons. The 670-bp fragment consists of a host sequence (226-bp) and the remaining LTR sequence (634−190=444 bp) after 190-bp excision by simultaneous cutting at LTR-A and B target sites. The underlined and highlighted sequences indicate the gRNA LTR-A target site and PAM.
Figures 2B, 2C:
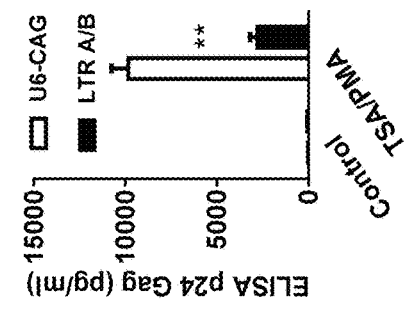

Example 3: Cas9/LTR-gRNA Efficiently Eradicates Latent HIV-1 Virus from U1 Monocytic Cells The promonocytic U-937 cell subclone U1, an HIV-1 latency model for infected perivascular macrophages and monocytes, is chronically HIV-1-infected and exhibits low level constitutive viral gene expression and replication. GENOMEWALKER™, mapping detected two integrated proviral DNA copies at chromosomes Xp11-4 (FIG. 2A) and 2p21 (FIG. 9A) in U1 cells. A 9935-bp DNA fragment representing the entire 9709-bp proviral HIV-1 DNA plus a flanking 226-bp X-chromosome-derived sequence (FIG. 2A), and a 10176-bp fragment containing 9709-bp HIV-1 genome plus its flanking 2-chromosome-derived 467-bp (FIG. 9A, FIG. 9B) were identified by the long-range PCR analysis of the parental control or empty-vector (U6-CAG) U1 cells. The 226-bp and 467-bp fragments represent the predicted segment from the other copy of chromosome X and 2 respectively, which lacked the Integrated proviral DNA. In U1 cells expressing LTR-A/B gRNAs and Cas9, we found two additional DNA fragments of 833 and 670 bp in chromosome X and one additional 1102-bp fragment in chromosome 2. Thus, gRNAs A/B enabled Cas9 to excise the HIV-1 5'-3' LTR-spanning viral genome segment in both chromosomes. The 833-bp fragment includes the expected 226-bp from the host genome and a 607-bp viral LTR sequence with a 27-bp deletion around the LTR-A site (FIG. 2A and FIG. 2B). The 670-bp fragment encompassed a 226-bp host sequence and residual 444-bp viral LTR sequence after 190-bp fragment excision (FIG. 1D), caused by gRNAs-A/B-guided cleavage at both LTRs (FIG. 2A). The additional fragments did not emerge via circular LTR integration, because it was absent in the parental U1 cells, and such circular LTR viral genome configuration occurs immediately after HIV-1 infection but is short lived and intolerant to repeated passaging. These cells exhibited substantially decreased HIV-1 viral load, shown by the functional p24 ELISA replication assay (FIG. 2C) and real-time PCR analysis (FIG. 9C, FIG. 9D). The detectable but low residual viral load and reactivation may result from cell population heterogeneity and/or incomplete genome editing. We also validated the ablation of HIV-1 genome by Cas9/LTR-A/B gRNAs in latently infected J-Lat T hells harboring integrated HIV-R7/E-/EGFP using flow cytometry analysis, SURVEYOR assay and PCR genotyping (FIG. 10), supporting the results of previous reports on HIV-1 proviral deletion in Jurkat T cells by Cas9/gRNA and ZFN. Taken together, our results suggest that the multiplex LTR-RNAs/Cas9 system efficiently suppress HIV-1 replication and reactivation in latently HIV-1-infected "reservoir" (microglial, monocytic and T) cells typical of human latent HIV-1 infection, and in TZM-bl cells highly sensitive for detecting HIV-1 transpiration and reactivation. Single of multiplex gRNAs targeting 5'- and 3'-LTRs effectively eradicated the entire HIV-1 genome.

Figure 11A:
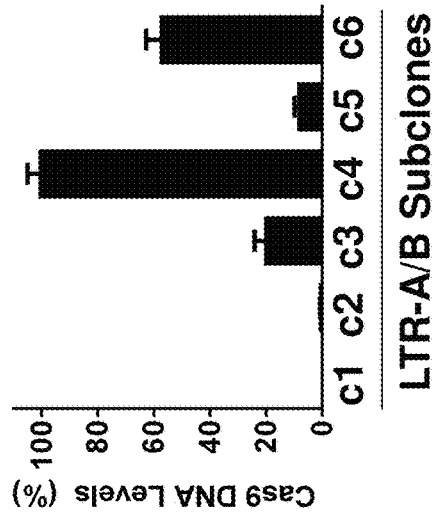
FIGS. 11A-11D show that genome editing efficiency depends upon the presence of Cas9 and gRNAs. (11A, 11B) PCR genotyping reveals the absence of a U6-driven LTR-A or LTR-B expression cassette (11A) and absence/reduction of CMV-driven Cas9 DNA (11B) in puromycin-selected TZM-bl subclones without any indication of genomic editing. Genomic DNAs from indicated subclones were subject to conventional (11A) or real-time (11B) PCR analyses using a primer pair covering U6 promoter (T351) and LTR-A (T354) or -B (T356), and targeting Cas9 (T477/T491). (11C, 11D) Cas9 protein expression is absent in ineffective TZM-bl subclones. The Flag-tagged Cas9 fusion protein was detected by Western blot (WB) and immunocytochemistry (ICC) with anti-Flag monoclonal antibody. HEK293T cell line stably expressing Flag-Cas9 was used as a positive control for WB (11C). GAPDH serves as a protein loading control. Clone c6 contains Cas9 DNA but no Cas9 protein expression, suggesting a potential mechanism of epigenetic repression after puromycin selection. Clone c5 and c3 may represent a truncated Flag-Cas9 (tCas9). Nucleus was stained with Hoechst 33258 (11D).
Figure 11B:
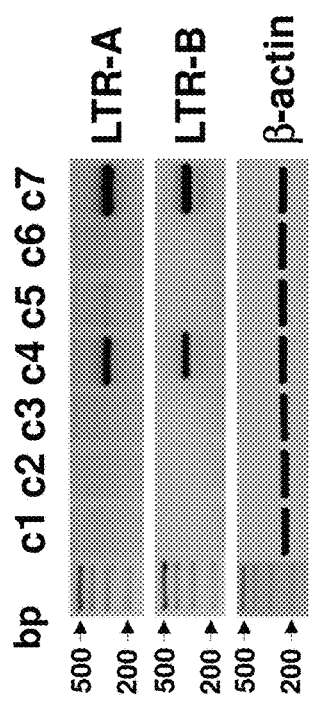
Figure 11C:
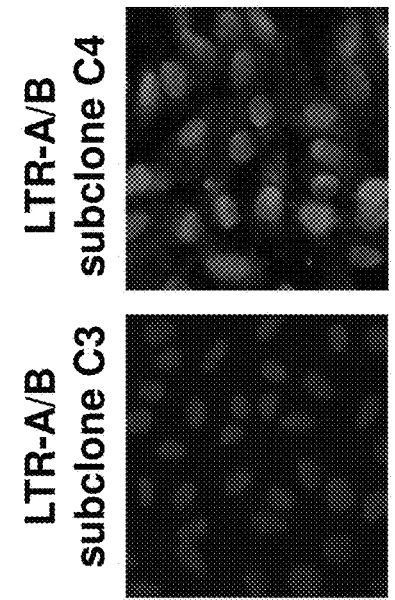
Figure 11D:
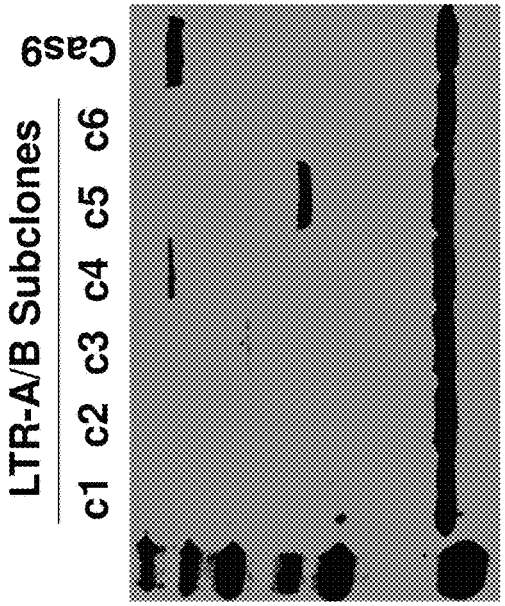
Figure 16F:
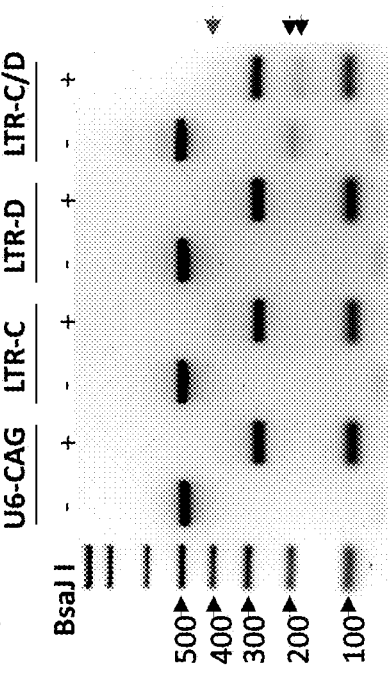
Figure 16G:
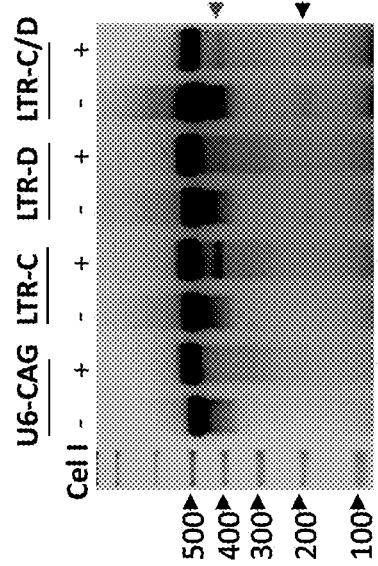
Figure 16H:
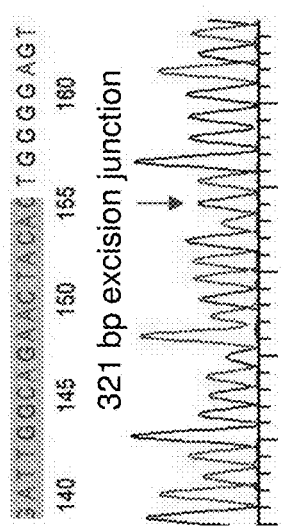
Figure 17A:
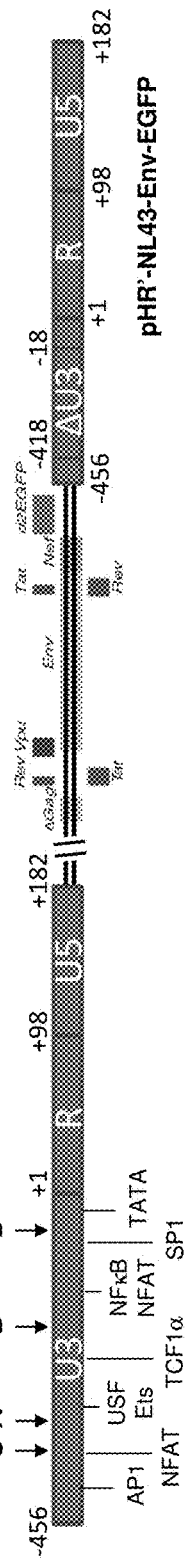
FIGS. 17A-17H show that Cas9/LTR-gRNA inhibited constitutive and inducible production of HIV-1 virus measured by EGFP flow cytometry in HIV-1 latently infected CHME5 microglia cell line. The pHR' lentiviral vector containing Tat, Rev, Env, Vpu, and Nef with the reported gene d2EGFP was transduced into human fetal microglia cell line CHME5 and 400 bp deletion in U3 region of 3'-LTR is illustrated (FIG. 17A). After transient transfection of Cas9/gRNA, Human HIV-1 LTR-A, B, C, D alone or combination decreased the intensity but not percentage of EGFP due to suppression of LTR promoter activity (FIGS. 17B, 17C). After antibiotic selection for 1-2 weeks, the percentage of EGFP cells was also reduced (FIGS. 17D, 17E). The PCR product from the stable selected clones were analyzed with Surveyor Cel-I nuclease assay (FIG. 17F) showing indel mutation dramatically in LTR-A and LTR-B but weakly in the combination of LTR-A/B (red arrow). A 331 bp fragment (FIGS. 17F, 17G, black arrow) resulting from the deletion of 190 bp region between LTR-A and LTR-B as predicted (FIG. 17H, red arrowhead) was validated by TA-cloning and sequencing showing precise genomic excision (FIG. 17H).
Figure 17B:
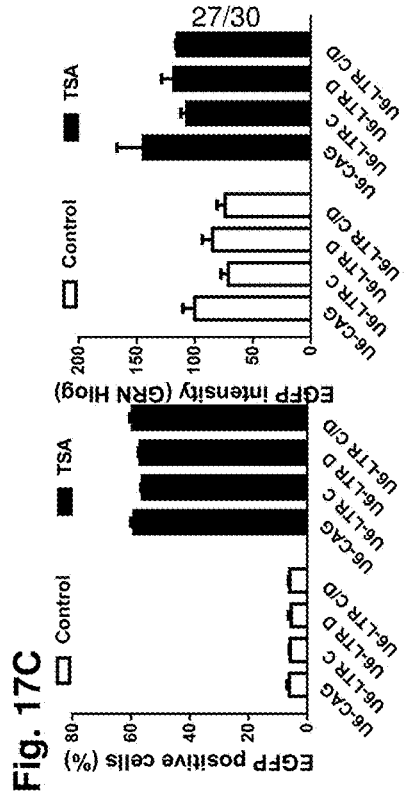
Figure 17C:
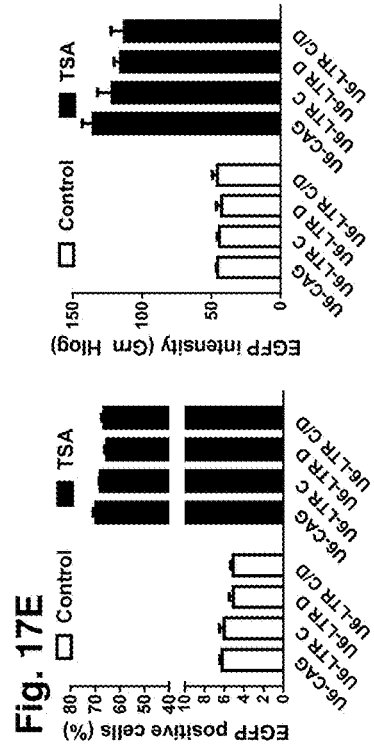
Figure 17D:
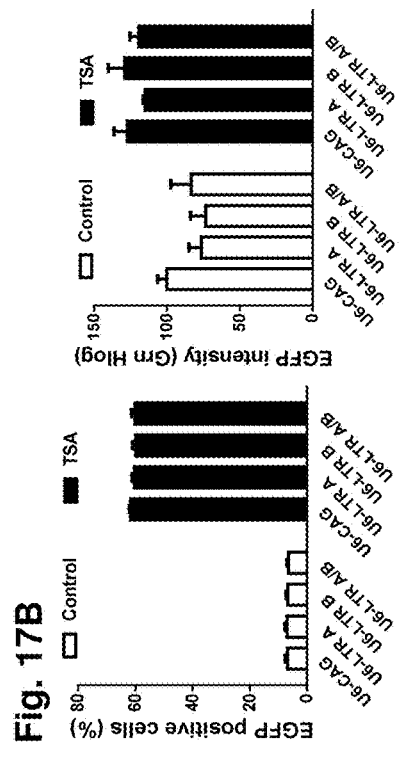
Figure 17E:
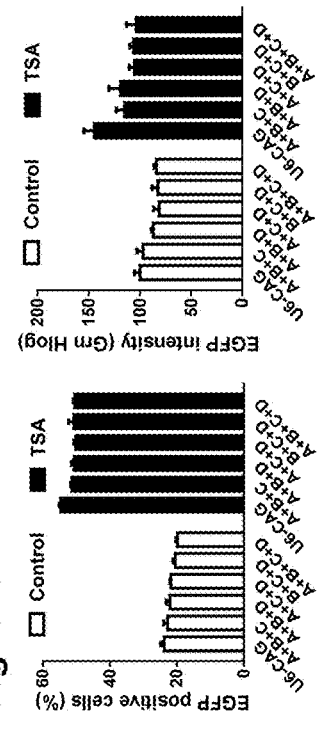
Figure 17G:
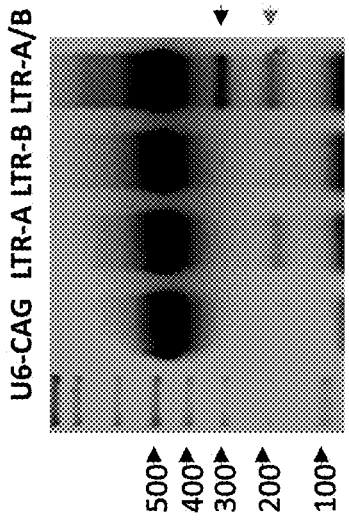
Figure 17F:
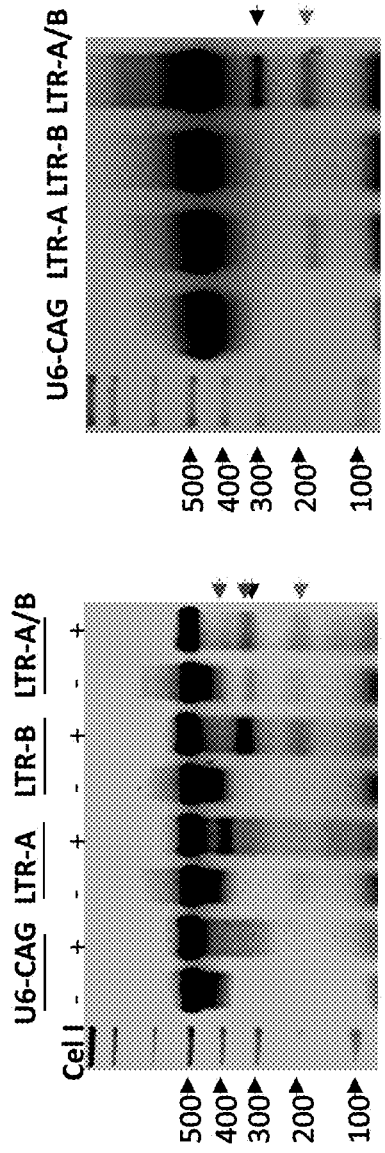
Figure 17H:
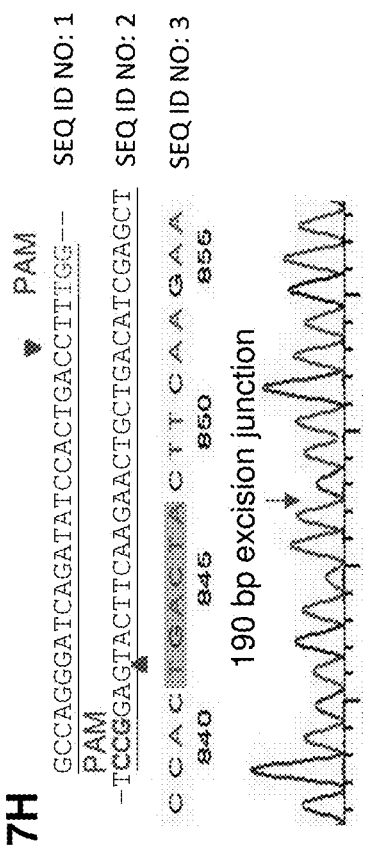

Example 4: Stable Expression of Cas9 Plus LTR-A/B Vaccinates TZM-Bl Cells Against New HIV-1 Virus Infection We next tested whether combined Cas9/LTR gRNAs can immunize cells against HIV-1 infection using stable Cas9/gRNAs-A and -B-expressing TZM-bl-based clones (FIG. 3A). Two of 7 puromycin-selected subclones exhibited efficient excision of the 190-bp LTR-A/B site-spanning DNA fragment (FIG. 3B). However, the remaining 5 subclones exhibited no excision (FIG. 3B) and no indel mutations as verified by Sanger sequencing. PCR genotyping using primers targeting Cas9 and U6-LTR showed that none of these ineffective subclones retained the integrated copies of Cas9/LTR-A/B gRNA expression cassettes. (FIG. 11A, B). As a result, no expression of full-length Cas9 was detected (FIG. 11C, D). The long-term expression of Cas9/LTR-A/B gRNAs did not adversely affect cell growth or viability, suggesting a low occurrence of off-target interference with the host genome or Cas9-induced toxicity in this model. We assessed de novo HIV-1 replication by infecting cells with the VSVG-pseudotyped pNL4-3-ΔE-EGFP reporter virus, with EGFP-positivity by flow cytometry indicating HIV-1 replication. Unlike the control U6-CAG cells, the cells stably expressing Cas9/gRNAs LTRs-A/B failed to support HIV-1 replication at 2 d post infection, indicating that they were immunized effectively against new HIV-1 infection (FIG. 3C-D). A similar immunity against HIV-1 was observed in Cas/LTR-A/B gRNA expressing cells infected with native T-tropic X4 strain pNL4-3-ΔE-EGFP reporter virus (FIG. 12A) or native M-tropic R5 strains such as SF162 and JRFL (FIG. 12B-D).

Example 5: Off-Target Effects of Cas9/LTR-A/B on Human Genome

The appeal of Cas9/gRNA as an interventional approach rests on its highly specific on-target indel-producing cleavage, but multiplex gRNAs could potentially cause host genome mutagenesis and chromosomal disorders, cytotoxicity, genotoxicity, or oncogenesis. Fairly low viral-human genome homology reduces this risk, but the human genome contains numerous endogenous retroviral genomes that are potentially susceptible to HIV-1-directed gRNAs. Therefore, we assessed off-target effects of selected HIV-1 LTR gRNAs on the human genome. Because the 12-14-bp seed sequence nearest the protospacer-adjacent motif (PAM) region (NGG) is critical for cleavage specificity, we searched >14-bp seed+NGG, and found no off-target candidate sites by LTR gRNAs A-D (FIG. 13). It is not surprising that progressively shorter gRNA segments yielded increasing off-target cleavage sites 100% matched to corresponding on-target sequences (i.e., NGG+13 bp yielded 6, 0, 2 and 9 off-target sites, respectively, whereas NGG+12 bp yielded 16, 5, 16 and 29; FIG. 13). From human genomic DNA we obtained a 500-800-bp sequence covering one of predicted off-target sites using high-fidelity PCR, and analyzed the potential mutations by SURVEYOR and Sanger sequencing. We found no mutations (see representative off-target sites #1, 5 and 6 in TZM-bl and U1 cells; FIG. 4A).

To assess risk of off-target effects comprehensively, we performed whole genome sequencing (WGS) using the stable Cas9/gRNA A/B-expressing and control U6-CAG TZM-bl cells (FIG. 4B-D). We identified 676,105 indels, using a genome analysis toolkit (GATK, v.2.8.1) with human (hg19) and HIV-1 genomes as reference sequences. Among the indels, 24% occurred in the U6-CAG control, 26% in LTR-A/B subclone, and 50% in both (FIG. 4B). Such substantial inter-sample indel-calling discrepancy suggests the probable off-target effects, but most likely results from its limited confidence, limited WGS coverage (15-30×), and cellular heterogeneity. GATK reported only confidently-identified indels: some found in the U6-CAG control but not in the LTR-A/B subclone, and others in the LTR-A/B but not in the U6-CAG. We expected abundant missing indel calls for both samples due to the limited WGS coverage. Such limited indel-calling confidence also implies the possibility of false negatives: missed indels occurring in LTR-A/B but not U6-CAG controls. Cellular heterogeneity may reflect variability of Cas9/gRNA editing efficiency and effects of passaging. Therefore, we tested whether each indel was LTR-A/B gRNA-induced, by analyzing ±300 bp flanking each indel against LTRs-A/-B-targeted sites of the HIV-1 genome and predicted/potential gRNA off-target sites of the host genome (FIG. 15). For sequences 100% matched to one containing the seed (12-bp) plus NRG, we identified only 8 overlapped regions of 92 potential off-target sites against 676,105 indels: 6 indels occurring in both samples, and 2 only in the U6-CAG control (FIG. 4C, D). We also identified 2 indels on HIV-1 LTR that occurred only in the LTR-A/B subclone but, as expected, not in the U6-CAG control (FIG. 4C). The results suggest that LTR-A/B gRNAs induce the indicated on-target indels, but no off-target indels, consistent with prior findings using deep sequencing of PCR products covering predicted/potential off-target site.

Our combined approaches minimized off-target effects while achieving high efficiency and complete ablation of the genomically integrated HIV-1 provirus. In addition to an extremely low homology between the foreign viral genome and host cellular genome including endogenous retroviral DNA, the key design attributes in our study included: bioinformatic screening using the strictest 12-bp+NGG target-selection criteria to exclude off-target human transcriptome or (even rarely) untranslated-genomic sites; avoiding transcription factor binding sites within the HIV-1 LTR promoter (potentially conserved in the host genome); selection of LTR-A- and -B-directed, 30-bp gRNAs and also pre-crRNA system reflecting the original bacterial immune mechanism to enhance specificity/efficiency vs. 20-bp gRNA-, chimeric crRNA-tracRNA-based system; and WGS, Sanger sequencing and SURVEYOR assay, to identify and exclude potential off-target effects. Indeed, the use of newly developed Cas9 double-nicking and RNA-guided FokI nuclease may further assist identification of new targets within the various conserved regions of HIV-1 with reduced off-target effects.

Our results show that the HIV-1 Cas9/gRNA system has the ability to target more than one copy of the LTR, which are positioned on different chromosomes, suggesting that this genome editing system can alter the DNA sequence of HIV-1 in latently infected patient's cells harboring multiple proviral DNAs. To further ensure high editing efficacy and consistency of our technology, one may consider the most stable region of HIV-1 genome as a target to eradicate HIV-1 in patient samples, which may not harbor only one strain of HIV-1. Alternatively, one may develop personalized treatment modalities based on the data from deep sequencing of the patient-derived viral genome prior to engineering therapeutic Cas9/gRNA molecules.

Our results also demonstrate that Cas9/gRNA genome editing can be used to immunize cells against HIV-1 infection. The preventative vaccination is independent of HIV-1 strain's diversity because the system targets genomic sequences regardless of how the viruses enter the infected cells. The preexistence of the Cas9/gRNA system in cells led to a rapid elimination of the new HIV-1 before it integrates into the host genome. One may explore various systems for delivery of Cas9/LTR-gRNA for immunizing high-risk subjects, e.g., gene therapies (viral vector and nanoparticle) and transplantation of autologous Cas9/gRNA-modified bone marrow stem/progenitor cells or inducible pluripotent stem cells for eradicating HIV-1 infection.

Here, we demonstrated the high specificity of Cas9/gRNAs in editing HIV-1 target genome. Results from subclone data revealed the strict dependence of genome editing on the presence of both Cas9 and gRNA. Moreover, only one nucleotide mismatch in the designed gRNA target will disable the editing potency. In addition, all of our 4 designed LTR gRNAs worked well with different cell lines, indicating that the editing is more efficient in the HIV-1 genome than the host cellular genome, wherein not all designed gRNAs are functional, which may be due to different epigenetic regulation, variable genome accessibility, or other reasons. Given the ease and rapidity of Cas9/gRNA development, even if HIV-1 mutations confer resistance to one Cas9/gRNA-based therapy, as described above, HIV-1 variants can be genotyped to enable another personalized therapy for individual patients.

A number of embodiments of the invention have been described. Nevertheless, it will be understood that various modifications may be made without departing from the spirit and scope of the invention. Accordingly, other embodiments are within the scope of the following claims.

What is claimed is:

1. A method of inactivating a proviral DNA integrated into the genome of a host cell latently infected with a retrovirus, including the steps of:
   treating the host cell with a composition comprising a Clustered Regularly Interspaced Short Palindromic Repeat (CRISPR)-associated endonuclease, and two or more different multiplex guide RNAs (gRNAs), wherein each of the at least two gRNAs is complementary to a different target nucleic acid sequence in a long terminal repeat (LTR) of the proviral DNA;
   cleaving a double strand of the proviral DNA at a first target protospacer sequence with the CRISPR-associated endonuclease;
   cleaving a double strand of the proviral DNA at a second target protospacer sequence with the CRISPR-associated endonuclease;
   excising an entire HIV-1 proviral genome; and
   eradicating the HIV-1 proviral DNA from the host cell.

2. The method according to claim 1, wherein said step of treating the host cell includes the steps of:
   exposing the host cell to a composition including an isolated nucleic acid encoding the CRISPR-associated endonuclease; an isolated nucleic acid sequence encoding a first multiplex gRNA having a first spacer sequence that is complementary to a first target protospacer sequence in a proviral DNA; and an isolated nucleic acid encoding a second multiplex gRNA having a second spacer sequence that is complementary to a second target protospacer sequence in the proviral DNA;
   expressing in the host cell the CRISPR-associated endonuclease, the first gRNA, and the second gRNA;
   assembling, in the host cell, a first gene editing complex including the CRISPR-associated endonuclease and the first gRNA; and a second gene editing complex including the CRISPR-associated endonuclease and the second gRNA;
   directing the first gene editing complex to the first target protospacer sequence by complementary base pairing between the first spacer sequence and the first target protospacer sequence;

directing the second gene editing complex to the second target protospacer sequence by complementary base pairing between the second spacer sequence and the second target protospacer sequence; and excising the proviral DNA.

3. The method according to claim 2, wherein at least one of the first target protospacer sequence and the second target protospacer sequence is situated within the U3 region of the LTR.

4. The method according to claim 3, wherein the first spacer sequence and the second spacer sequence each include a sequence complementary to a target protospacer sequence selected from the group consisting of SEQ ID NO: 96, SEQ ID NO: 121, SEQ ID NO: 87, and SEQ ID NO: 110.

5. The method according to claim 3, wherein the first spacer sequence and the second spacer sequence include, respectively, a sequence complementary to the target protospacer sequences SEQ ID NO: 96 and SEQ ID NO: 121.

6. The method according to claim 3, wherein the first spacer sequence and the second spacer sequence each include, respectively, a sequence complementary to the target protospacer sequences SEQ ID NO: 87 and SEQ ID NO: 110.

7. The method according to claim 2, wherein the isolated nucleic acids encoding a CRISPR-associated endonuclease, the first gRNA, and the second gRNA, are encoded in at least one expression vector.

8. The method according to claim 7, wherein the at least one expression vector is selected from the group consisting of a plasmid vector, a lentiviral vector, an adenoviral vector, and an adeno-associated virus vector.

9. The method of claim 2, wherein said step of expressing in the host cell the CRISPR-associated endonuclease, the first gRNA, and the second gRNA, is further defined as stably expressing in the host cell the CRISPR-associated endonuclease, the first gRNA, and the second gRNA, and the method additionally includes the step of immunizing the host cell against new retroviral infection.

10. The method according to claim 1, wherein the CRISPR-associated endonuclease is cas9 or a human-optimized cas9.

11. The method according to claim 1, wherein at least one of the gRNAs comprises a CRISPR RNA (crRNA) and a trans-activated small RNA (tracrRNA), which are expressed as separate nucleic acids.

12. The method according to claim 1, wherein at least one of the gRNAs is engineered as an artificial fusion small guide RNA (sgRNA) comprised of a crRNA and a tracrRNA.

13. The method according to claim 1, wherein the host cell latently infected with a retrovirus is a CD4+ T cell, a macrophage, a monocyte, a gut associated lymphoid cell, a microglial cell, or an astrocyte.

* * * * *

UNITED STATES PATENT AND TRADEMARK OFFICE
CERTIFICATE OF CORRECTION

Page 1 of 1

PATENT NO. : 9,925,248 B2
APPLICATION NO. : 14/838057
DATED : March 27, 2018
INVENTOR(S) : Kamel Khalili and Wenhui Hu It is certified that error appears in the above-identified patent and that said Letters Patent is hereby corrected as shown below:

In the Specification

At Column 1, Line numbers 8-12 should read "This invention was made with government support under P30 MH092177, R01 MH093271, and R01 NS087971 awarded by the National Institutes of Health. The government has certain rights in the invention."

Signed and Sealed this
Fourteenth Day of November, 2023

Katherine Kelly Vidal
*Director of the United States Patent and Trademark Office*

SEQUENCE LISTING

```
<160> NUMBER OF SEQ ID NOS: 389

<210> SEQ ID NO 1
<211> LENGTH: 30
<212> TYPE: DNA
<213> ORGANISM: Human immunodeficiency virus 1

<400> SEQUENCE: 1
gccagggatc agatatccac tgacctttgg                                   30

<210> SEQ ID NO 2
<211> LENGTH: 34
<212> TYPE: DNA
<213> ORGANISM: Human immunodeficiency virus 1

<400> SEQUENCE: 2
tccggagtac ttcaagaact gctgacatcg agct                              34

<210> SEQ ID NO 3
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccactgacta cttcaagaa                                                     19

<210> SEQ ID NO 4
<211> LENGTH: 859
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (289)..(313)
<223> OTHER INFORMATION: a, c, t, g, unknown or other
<220> FEATURE:
<221> NAME/KEY: misc_feature
<222> LOCATION: (289)..(313)
<223> OTHER INFORMATION: n is a, c, g, or t

<400> SEQUENCE: 4
ctaggtgatt aggatattct acaatccaaa ttcttaccag tttgggatta ttcaaattgg          60
gcaccttggc agatatgttt tgaaaactgc taggcaaagc attctggaag aatagacaaa         120
gaagtaataa aatataacaa aaagcagtgg aagttacaaa aaaaaatgtt tctcttttgg         180
aagggctaat ttggtcccaa agaagacaag atatccttga tctgtggatc taccacacac         240
aaggctactt ccctgattgg cagaactaca acaccagggc cagggatcnn nnnnnnnnnn         300
nnnnnnnnnn nnnttcaagt tagtaccagt tgagccaggg caggtagaag aggccaatga         360
aggagagaac aaccccttgt tacaccctat gagcctgcat gggatggagg acccggaggg         420
agaagtatta gtgtggaagt ttgacagcct cctagcattt cgtcacatgg cccgagagct         480
gcatccggag tactacaaag actgctgaca tcgagttttc tacaagggac tttccgctgg         540
ggactttcca gggaggtgtg gcctgggcgg gactggggag tggcgagccc tcagatgctg         600
catataagca gctgcttttt gcctgtactg ggtctctctg gttagaccag atctgagcct         660
gggagctctc tggctagcta gggaacccac tgcttaagcc tcaataaagc ttgccttgag         720
tgctacaagt agtgtgtgcc cgtctgttgt gtgactctgg taactagaga tccctcagac         780
ccttttagtc agtgtggaaa atctctagca tctttaaagt acagaatgcc aaaacaggaa         840
ggattgataa gatagtcgt                                                    859

<210> SEQ ID NO 5
<211> LENGTH: 10
<212> TYPE: DNA
<213> ORGANISM: Human immunodeficiency virus 1

<400> SEQUENCE: 5
tcttttggaa                                                               10

<210> SEQ ID NO 6
<211> LENGTH: 76
<212> TYPE: DNA
<213> ORGANISM: Human immunodeficiency virus 1

<400> SEQUENCE: 6
gattggcaga actacacacc agggccaggg atcagatatc cactgacctt tggatggtgc         60
```

```
ttcaagttag taccag                                                    76

<210> SEQ ID NO 7
<211> LENGTH: 10
<212> TYPE: DNA
<213> ORGANISM: Human immunodeficiency virus 1

<400> SEQUENCE: 7
tctttaaagt                                                           10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcttttggaa                                                           10

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gattggcaga actacaacac cagggccagg gatcagatgg atggtgcttc aagttagtac    60
cag                                                                  63

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tctttaaagt                                                           10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcttttggaa                                                           10

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gattggcaga actacaacac cagggccagg gatcttcaag ttagtaccag                50
```

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tctttaaagt                                                                10

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gagatcctgt ctcaaaaaaa agtt                                                24

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atctatccat gagggcg                                                        17

<210> SEQ ID NO 16
<211> LENGTH: 402
<212> TYPE: DNA
<213> ORGANISM: Human immunodeficiency virus 1

<400> SEQUENCE: 16
gatctgtgga tctaccacac acaaggctac ttccctgatt ggcagaacta cacaccaggg         60
ccagggatca gatatccact gacctttgga tggtgctaca agctagtacc agttgagcaa        120
gagaaggtag aagaagccaa tgaaggagag aacacccgct tgttcacccc tgtgagcctg        180
catgggatgg atgaccccgga gagagaagta ttagagtgga ggtttgacag ccgcctagca      240
tttcatcaca tggcccgaga gctgcatccg gagtacttca agaactgctg acatcgagct       300
tgctacaagg gactttccgc tggggacttt ccagggaggc gtggcctggg cgggactggg       360
gagtggcgag ccctcagatg ctgcatataa gcagctgctt tt                          402

<210> SEQ ID NO 17
<211> LENGTH: 31
<212> TYPE: DNA
<213> ORGANISM: Human immunodeficiency virus 1

<400> SEQUENCE: 17
ccctgattgg cagaactaca caccagggcc a                                        31

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 18
ccctgattgg cagaactaca acaccagggc ca                                          32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccctgattgg cagaactaca acaccagggc ca                                          32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccctgattgg cagaactaca acaccagggc ca                                          32

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccctgattgg cagaactaca accagggcca                                             30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccctgattgg cagaactaca ccagggcca                                              29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccctgattgg cagaactaca ccagggcca                                              29

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccctgattgg cagaactaca gggcca                                          26

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccctgattgg cagaactaca gggccaggg                                       29

<210> SEQ ID NO 26
<211> LENGTH: 86
<212> TYPE: DNA
<213> ORGANISM: Human immunodeficiency virus 1

<400> SEQUENCE: 26
gactttccag ggaggcgtgg cctgggcggg actggggagt ggcgagccct cagatgctgc    60
atataagcag cggtgaagcc gaattc                                          86

<210> SEQ ID NO 27
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gactttccag ggaggcgtgg cctgggcggg actgggggt ggcgagccct cagatgctgc     60
atataagcag cggtgaagcc gaattc                                          86

<210> SEQ ID NO 28
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gactttccag ggaggcgtgg cctgggcggg tatctgggga gtggcgagcc ctcagatgct    60
gcatataagc agcggtgaag ccgaattc                                        88

<210> SEQ ID NO 29
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gactttccag gggggcgtgg cctgggcggg actggggagt ggcgagccct cagatgctgc    60
ataaagcagc ggtgaagccg aattc                                           85

<210> SEQ ID NO 30
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 30
gactttccag ggaagccgaa ttc                                           23

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gattggcaga actacactgg ggagt                                         25

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gattggcaga actacacctc agatgc                                        26

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
catcacatgg cccgctgctg acatcgag                                      28

<210> SEQ ID NO 34
<211> LENGTH: 55
<212> TYPE: DNA
<213> ORGANISM: Human immunodeficiency virus 1

<400> SEQUENCE: 34
catcacgtgg cccgagagct gcatccggag tacttcaaga actgctgaca tcgag        55

<210> SEQ ID NO 35
<211> LENGTH: 1106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (152)..(155)
<223> OTHER INFORMATION: a, c, t, g, unknown or other
<220> FEATURE:
<221> NAME/KEY: misc_feature
<222> LOCATION: (152)..(155)
<223> OTHER INFORMATION: n is a, c, g, or t

<400> SEQUENCE: 35
gctattgtat ctgatcacaa gctgttaaaa gcggtcatgc cacttcttga atgctttgca   60
gctggaaggg ctaatttggt cccaaagaag acaagatatc cttgatctgt ggatctacca  120
```

```
cacacaaggc tacttccctg attggcagaa cnnnncacca gggccaggga tcagatatcc      180
actgaccatc cactttggat ggtgcttcaa gttagtacca gttgagccag ggcaggtaga      240
agaggccaat gaaggagaga acaacacctt gttacaccct atgagcctgc atgggatgga      300
ggacccggag ggagaagtat tagtgtggaa gtttgacagc ctcctagcat ttcgtcacat      360
ggcccgagag ctgcatccgg agtactacaa agactgctga catcgagttt tctacaaggg      420
actttccgct ggggactttc cagggaggtg tggcctgggc gggactgggg agtggcgagc      480
cctcagatgc tgcatataag cagctgcttt ttgcctgtac tgggtctctc tggttagacc      540
agatctgagc ctgggagctc tctggctagc tagggaaccc actgcttaag cctcaataaa      600
gcttgccttg agtgctacaa gtagtgtgtg cccgtctgtt gtgtgactct ggtaactaga      660
gatccctcag acccttttag tcagtgtgga aaatctctag cagcagctta gaaatttttt      720
ccaccagagg ccgggcgtgg tggctcacgc ctgtaatccc agcactttgg gaggccgagg      780
tgggcggatc acctgaagtc aggagttcga ccagcctc aacatggaga aaccccatct       840
ctactaaaaa tacaaaatta gctgggcgtg gtggtgcatg cctgtaatcc cagctacttg      900
ggaggctgag acaggataat tgcttgaacc tggaaggcag aggttgcggt gagccgagat      960
tgcgccattg cattccagcc tgggcaacag gagcgaaact tcgtctcaaa aaaaaaaaa     1020 aaagacattt tttccaccag ataccctaga tcatgactgt taagtctggc cttccacgaa     1080
gccctaggac ctggacacac aatcaa                                          1106

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaacagggcc agggatcaga tatccactga ccttgt                                36

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
taaacaaggt cagtggatat ctgatccctg gccct                                 35

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aaacagctcg atgtcagcag ttcttgaagt actcgt                                36

<210> SEQ ID NO 39
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 39
taaacgagta cttcaagaac tgctgacatc gagct                           35

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caccgattgg cagaactaca cacc                                       24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aaacggtgtg tagttctgcc aatc                                       24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caccgcgtgg cctgggcggg actg                                       24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aaaccagtcc cgcccaggcc acgc                                       24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tggaagggct aattcactcc caac                                       24

<210> SEQ ID NO 45
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 45
ccgagagctc ccaggctcag atct                                              24

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caccgatctg tggatctacc acacaca                                           27

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaacgagtca cacaacagac gggc                                              24

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgcctcgagg atccgagggc ctatttccca tgattcc                                37

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgtgaattca ggcgggccat ttaccgtaag ttatg                                  35

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acgactatct tatcaatcct tcctg                                             25

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 51
ctaggtgatt aggatattct acaatc                                                                        26

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctattgtat ctgatcacaa gctg                                                                        24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttgattgtgt gtccaggtcc tagg                                                                        24

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcaagggcga ggagctgttc acc                                                                        23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttgtagttgc cgtcgtcctt gaag                                                                       24

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aatggtacat caggccatat cac                                                                       23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cccactgtgt ttagcatggt att                                              23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cacagcatca agaagaacct gat                                              23

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tcttccgtct ggtgtatctt cttc                                             24

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cgccaagctt gaataggagc tttgttcc                                         28

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctaggatcca ggagctgttg atcctttagg                                       30

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gtggactttg gatggtgaga tag                                              23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 63
gcctggcaag agtgaactga gtc                                           23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aagataatga gttgtggcag agc                                           23

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tctacctggt aatccagcat ctgg                                          24

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ataggaggaa ggcaccaaga ggg                                           23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aatgatgctt tggtcctact cct                                           23

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgctcttgct actctggcat gtac                                          24

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
```
aatctacctc tgagagctgc agg                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tcagacacag ctgaagcaga ggc                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atgccagtgt cagtagatgt cag                                              23

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tcaagatcag ccagagtgca catg                                             24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgctcttccg agcctctctg gag                                              23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atggactatc atatgcttac cg                                               22

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gcttcagcaa gccgagtcct gcgtcgag					28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gctcctctgg tttcccttc gctttcaa					28

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gtaatacgac tcactatagg gc					22

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
actatagggc acgcgtggt					19

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tcagaccctt ttagtcagtg tgg					23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ttgcttgtac tgggtctctc tgg					23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagctgcttt ttgcttgtac tgg					23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctgacatcga gcttgctaca agg                                            23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ccgcctagca tttcatcaca tgg                                            23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cggagagaga agtattagag tgg                                            23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agtaccagtt gagcaagaga agg                                            23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gatatccact gacctttgga tgg                                            23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gattggcaga actacacacc agg                                            23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cacaaggcta cttccctgat tgg                                             23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctgtggatct accacacaca agg                                             23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tgggagctct ctggctaact agg                                             23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggttagacca gatctgagcc tgg                                             23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tgctacaagg gactttccgc tgg                                             23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agagagaagt attagagtgg agg                                             23

```
<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ttacaccctg tgagcctgca tgg                                            23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaggtagaag aagccaatga agg                                            23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
atcagatatc cactgacctt tgg                                            23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gacaagatat ccttgatctg tgg                                            23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gcccgtctgt tgtgtgactc tgg                                            23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
atctgagcct gggagctctc tgg                                            23

<210> SEQ ID NO 100
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctttccgctg gggactttcc agg                                                 23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cagaactaca caccagggcc agg                                                 23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cctgcatggg atggatgacc cgg                                                 23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccctgtgagc ctgcatggga tgg                                                 23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ctttccaggg aggcgtggcc tgg                                                 23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggggactttc cagggaggcg tgg                                                 23

<210> SEQ ID NO 106
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ccgctgggga ctttccaggg agg                                                23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
catggcccga gagctgcatc cgg                                                23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gcctgggcgg gactggggag tgg                                                23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aggcgtggcc tgggcgggac tgg                                                23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gcgtggcctg ggcgggactg ggg                                                23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ccagggaggc gtggcctggg cgg                                                23

<210> SEQ ID NO 112
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 112
tgtggtagat ccacagatca agg                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggtgtgtagt tctgccaatc agg                                              23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gtcagtggat atctgatccc tgg                                              23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tagcaccatc caaaggtcag tgg                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tagcttgtag caccatccaa agg                                              23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tctaccttct cttgctcaac tgg                                              23

<210> SEQ ID NO 118
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 118
cactctaata cttctctctc cgg                                              23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ccatgtgatg aaatgctagg cgg                                              23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gggccatgtg atgaaatgct agg                                              23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cagcagttct tgaagtactc cgg                                              23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctgcttatat gcagcatctg agg                                              23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cacactactt gaagcactca agg                                              23

<210> SEQ ID NO 124
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 124
taccagagtc acacaacaga cgg                                           23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
acactgacta aaagggtctg agg                                           23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
caaggatatc ttgtcttcgt tgg                                           23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cagggaagta gccttgtgtg tgg                                           23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcgggtgttc tctccttcat tgg                                           23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tagttagcca gagagctccc agg                                           23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 130
ctttattgag gcttaagcag tgg                                            23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
actcaaggca agctttattg agg                                            23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggatatctga tccctggccc tgg                                            23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggctcacagg gtgtaacaag cgg                                            23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tccatcccat gcaggctcac agg                                            23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
agtactccgg atgcagctct cgg                                            23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
agagctccca ggctcagatc tgg                                              23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gattttccac actgactaaa agg                                              23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ccgggtcatc catcccatgc agg                                              23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cctccctgga aagtccccag cgg                                              23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gccactcccc agtcccgccc agg                                              23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccgcccaggc cacgcctccc tgg                                              23

<210> SEQ ID NO 142
<211> LENGTH: 23
<212> TYPE: DNA
<213> ORGANISM: Human immunodeficiency virus 1

<400> SEQUENCE: 142
atcagatatc cactgacctt tgg                                              23

```
<210> SEQ ID NO 143
<211> LENGTH: 22
<212> TYPE: DNA
<213> ORGANISM: Human immunodeficiency virus 1

<400> SEQUENCE: 143
tcagatatcc actgaccttt gg                                            22

<210> SEQ ID NO 144
<211> LENGTH: 22
<212> TYPE: DNA
<213> ORGANISM: Human immunodeficiency virus 1

<400> SEQUENCE: 144
tcagatatcc actgaccttt gg                                            22

<210> SEQ ID NO 145
<211> LENGTH: 21
<212> TYPE: DNA
<213> ORGANISM: Human immunodeficiency virus 1

<400> SEQUENCE: 145
cagatatcca ctgacctttg g                                             21

<210> SEQ ID NO 146
<211> LENGTH: 21
<212> TYPE: DNA
<213> ORGANISM: Human immunodeficiency virus 1

<400> SEQUENCE: 146
cagatatcca ctgacctttg g                                             21

<210> SEQ ID NO 147
<211> LENGTH: 20
<212> TYPE: DNA
<213> ORGANISM: Human immunodeficiency virus 1

<400> SEQUENCE: 147
agatatccac tgacctttgg                                               20

<210> SEQ ID NO 148
<211> LENGTH: 20
<212> TYPE: DNA
<213> ORGANISM: Human immunodeficiency virus 1

<400> SEQUENCE: 148
agatatccac tgacctttgg                                               20

<210> SEQ ID NO 149
<211> LENGTH: 19
<212> TYPE: DNA
<213> ORGANISM: Human immunodeficiency virus 1

<400> SEQUENCE: 149
gatatccact gacctttgg                                                19

<210> SEQ ID NO 150
<211> LENGTH: 19
<212> TYPE: DNA
<213> ORGANISM: Human immunodeficiency virus 1

<400> SEQUENCE: 150
```

```
gatatccact gacctttgg                                          19

<210> SEQ ID NO 151
<211> LENGTH: 18
<212> TYPE: DNA
<213> ORGANISM: Human immunodeficiency virus 1

<400> SEQUENCE: 151
atatccactg acctttgg                                           18

<210> SEQ ID NO 152
<211> LENGTH: 18
<212> TYPE: DNA
<213> ORGANISM: Human immunodeficiency virus 1

<400> SEQUENCE: 152
atatccactg acctttgg                                           18

<210> SEQ ID NO 153
<211> LENGTH: 17
<212> TYPE: DNA
<213> ORGANISM: Human immunodeficiency virus 1

<400> SEQUENCE: 153
tatccactga ccttggg                                            17

<210> SEQ ID NO 154
<211> LENGTH: 17
<212> TYPE: DNA
<213> ORGANISM: Human immunodeficiency virus 1

<400> SEQUENCE: 154
tatccactga cctttgg                                            17

<210> SEQ ID NO 155
<211> LENGTH: 17
<212> TYPE: DNA
<213> ORGANISM: Human immunodeficiency virus 1

<400> SEQUENCE: 155
tatccactga cctttgg                                            17

<210> SEQ ID NO 156
<211> LENGTH: 17
<212> TYPE: DNA
<213> ORGANISM: Human immunodeficiency virus 1

<400> SEQUENCE: 156
tatccactga ccttaag                                            17

<210> SEQ ID NO 157
<211> LENGTH: 17
<212> TYPE: DNA
<213> ORGANISM: Human immunodeficiency virus 1

<400> SEQUENCE: 157
tatccactga ccttgag                                            17

<210> SEQ ID NO 158
<211> LENGTH: 16
<212> TYPE: DNA
<213> ORGANISM: Human immunodeficiency virus 1

<400> SEQUENCE: 158
```

-continued

```
atccactgac cttagg                                              16

<210> SEQ ID NO 159
<211> LENGTH: 16
<212> TYPE: DNA
<213> ORGANISM: Human immunodeficiency virus 1

<400> SEQUENCE: 159
atccactgac cttagg                                              16

<210> SEQ ID NO 160
<211> LENGTH: 16
<212> TYPE: DNA
<213> ORGANISM: Human immunodeficiency virus 1

<400> SEQUENCE: 160
atccactgac cttggg                                              16

<210> SEQ ID NO 161
<211> LENGTH: 16
<212> TYPE: DNA
<213> ORGANISM: Human immunodeficiency virus 1

<400> SEQUENCE: 161
atccactgac cttggg                                              16

<210> SEQ ID NO 162
<211> LENGTH: 16
<212> TYPE: DNA
<213> ORGANISM: Human immunodeficiency virus 1

<400> SEQUENCE: 162
atccactgac cttggg                                              16

<210> SEQ ID NO 163
<211> LENGTH: 16
<212> TYPE: DNA
<213> ORGANISM: Human immunodeficiency virus 1

<400> SEQUENCE: 163
atccactgac cttggg                                              16

<210> SEQ ID NO 164
<211> LENGTH: 16
<212> TYPE: DNA
<213> ORGANISM: Human immunodeficiency virus 1

<400> SEQUENCE: 164
atccactgac ctttgg                                              16

<210> SEQ ID NO 165
<211> LENGTH: 16
<212> TYPE: DNA
<213> ORGANISM: Human immunodeficiency virus 1

<400> SEQUENCE: 165
atccactgac ctttgg                                              16

<210> SEQ ID NO 166
<211> LENGTH: 16
<212> TYPE: DNA
<213> ORGANISM: Human immunodeficiency virus 1
```

```
<400> SEQUENCE: 166
atccactgac ctttgg                                              16

<210> SEQ ID NO 167
<211> LENGTH: 16
<212> TYPE: DNA
<213> ORGANISM: Human immunodeficiency virus 1

<400> SEQUENCE: 167
atccactgac cttaag                                              16

<210> SEQ ID NO 168
<211> LENGTH: 16
<212> TYPE: DNA
<213> ORGANISM: Human immunodeficiency virus 1

<400> SEQUENCE: 168
atccactgac cttaag                                              16

<210> SEQ ID NO 169
<211> LENGTH: 16
<212> TYPE: DNA
<213> ORGANISM: Human immunodeficiency virus 1

<400> SEQUENCE: 169
atccactgac cttcag                                              16

<210> SEQ ID NO 170
<211> LENGTH: 16
<212> TYPE: DNA
<213> ORGANISM: Human immunodeficiency virus 1

<400> SEQUENCE: 170
atccactgac cttcag                                              16

<210> SEQ ID NO 171
<211> LENGTH: 16
<212> TYPE: DNA
<213> ORGANISM: Human immunodeficiency virus 1

<400> SEQUENCE: 171
atccactgac cttgag                                              16

<210> SEQ ID NO 172
<211> LENGTH: 16
<212> TYPE: DNA
<213> ORGANISM: Human immunodeficiency virus 1

<400> SEQUENCE: 172
atccactgac cttgag                                              16

<210> SEQ ID NO 173
<211> LENGTH: 15
<212> TYPE: DNA
<213> ORGANISM: Human immunodeficiency virus 1

<400> SEQUENCE: 173
tccactgacc ttagg                                               15

<210> SEQ ID NO 174
<211> LENGTH: 15
<212> TYPE: DNA
<213> ORGANISM: Human immunodeficiency virus 1
```

```
<400> SEQUENCE: 174
tccactgacc ttagg                                                   15

<210> SEQ ID NO 175
<211> LENGTH: 15
<212> TYPE: DNA
<213> ORGANISM: Human immunodeficiency virus 1

<400> SEQUENCE: 175
tccactgacc ttagg                                                   15

<210> SEQ ID NO 176
<211> LENGTH: 15
<212> TYPE: DNA
<213> ORGANISM: Human immunodeficiency virus 1

<400> SEQUENCE: 176
tccactgacc ttagg                                                   15

<210> SEQ ID NO 177
<211> LENGTH: 15
<212> TYPE: DNA
<213> ORGANISM: Human immunodeficiency virus 1

<400> SEQUENCE: 177
tccactgacc ttagg                                                   15

<210> SEQ ID NO 178
<211> LENGTH: 15
<212> TYPE: DNA
<213> ORGANISM: Human immunodeficiency virus 1

<400> SEQUENCE: 178
tccactgacc ttagg                                                   15

<210> SEQ ID NO 179
<211> LENGTH: 15
<212> TYPE: DNA
<213> ORGANISM: Human immunodeficiency virus 1

<400> SEQUENCE: 179
tccactgacc ttggg                                                   15

<210> SEQ ID NO 180
<211> LENGTH: 15
<212> TYPE: DNA
<213> ORGANISM: Human immunodeficiency virus 1

<400> SEQUENCE: 180
tccactgacc ttggg                                                   15

<210> SEQ ID NO 181
<211> LENGTH: 15
<212> TYPE: DNA
<213> ORGANISM: Human immunodeficiency virus 1

<400> SEQUENCE: 181
tccactgacc ttggg                                                   15

<210> SEQ ID NO 182
<211> LENGTH: 15
<212> TYPE: DNA
```

-continued

<213> ORGANISM: Human immunodeficiency virus 1

<400> SEQUENCE: 182
tccactgacc ttggg                                                        15

<210> SEQ ID NO 183
<211> LENGTH: 15
<212> TYPE: DNA
<213> ORGANISM: Human immunodeficiency virus 1

<400> SEQUENCE: 183
tccactgacc ttggg                                                        15

<210> SEQ ID NO 184
<211> LENGTH: 15
<212> TYPE: DNA
<213> ORGANISM: Human immunodeficiency virus 1

<400> SEQUENCE: 184
tccactgacc ttggg                                                        15

<210> SEQ ID NO 185
<211> LENGTH: 15
<212> TYPE: DNA
<213> ORGANISM: Human immunodeficiency virus 1

<400> SEQUENCE: 185
tccactgacc ttggg                                                        15

<210> SEQ ID NO 186
<211> LENGTH: 15
<212> TYPE: DNA
<213> ORGANISM: Human immunodeficiency virus 1

<400> SEQUENCE: 186
tccactgacc ttggg                                                        15

<210> SEQ ID NO 187
<211> LENGTH: 15
<212> TYPE: DNA
<213> ORGANISM: Human immunodeficiency virus 1

<400> SEQUENCE: 187
tccactgacc tttgg                                                        15

<210> SEQ ID NO 188
<211> LENGTH: 15
<212> TYPE: DNA
<213> ORGANISM: Human immunodeficiency virus 1

<400> SEQUENCE: 188
tccactgacc tttgg                                                        15

<210> SEQ ID NO 189
<211> LENGTH: 15
<212> TYPE: DNA
<213> ORGANISM: Human immunodeficiency virus 1

<400> SEQUENCE: 189
tccactgacc tttgg                                                        15

<210> SEQ ID NO 190
<211> LENGTH: 15

```
<212> TYPE: DNA
<213> ORGANISM: Human immunodeficiency virus 1

<400> SEQUENCE: 190
tccactgacc tttgg                                                  15

<210> SEQ ID NO 191
<211> LENGTH: 15
<212> TYPE: DNA
<213> ORGANISM: Human immunodeficiency virus 1

<400> SEQUENCE: 191
tccactgacc tttgg                                                  15

<210> SEQ ID NO 192
<211> LENGTH: 15
<212> TYPE: DNA
<213> ORGANISM: Human immunodeficiency virus 1

<400> SEQUENCE: 192
tccactgacc tttgg                                                  15

<210> SEQ ID NO 193
<211> LENGTH: 15
<212> TYPE: DNA
<213> ORGANISM: Human immunodeficiency virus 1

<400> SEQUENCE: 193
tccactgacc tttgg                                                  15

<210> SEQ ID NO 194
<211> LENGTH: 15
<212> TYPE: DNA
<213> ORGANISM: Human immunodeficiency virus 1

<400> SEQUENCE: 194
tccactgacc tttgg                                                  15

<210> SEQ ID NO 195
<211> LENGTH: 15
<212> TYPE: DNA
<213> ORGANISM: Human immunodeficiency virus 1

<400> SEQUENCE: 195
tccactgacc tttgg                                                  15

<210> SEQ ID NO 196
<211> LENGTH: 15
<212> TYPE: DNA
<213> ORGANISM: Human immunodeficiency virus 1

<400> SEQUENCE: 196
tccactgacc ttaag                                                  15

<210> SEQ ID NO 197
<211> LENGTH: 15
<212> TYPE: DNA
<213> ORGANISM: Human immunodeficiency virus 1

<400> SEQUENCE: 197
tccactgacc ttaag                                                  15

<210> SEQ ID NO 198
```

<210> SEQ ID NO 198
<211> LENGTH: 15
<212> TYPE: DNA
<213> ORGANISM: Human immunodeficiency virus 1

<400> SEQUENCE: 198
tccactgacc ttaag                                                    15

<210> SEQ ID NO 199
<211> LENGTH: 15
<212> TYPE: DNA
<213> ORGANISM: Human immunodeficiency virus 1

<400> SEQUENCE: 199
tccactgacc ttaag                                                    15

<210> SEQ ID NO 200
<211> LENGTH: 15
<212> TYPE: DNA
<213> ORGANISM: Human immunodeficiency virus 1

<400> SEQUENCE: 200
tccactgacc ttaag                                                    15

<210> SEQ ID NO 201
<211> LENGTH: 15
<212> TYPE: DNA
<213> ORGANISM: Human immunodeficiency virus 1

<400> SEQUENCE: 201
tccactgacc ttcag                                                    15

<210> SEQ ID NO 202
<211> LENGTH: 15
<212> TYPE: DNA
<213> ORGANISM: Human immunodeficiency virus 1

<400> SEQUENCE: 202
tccactgacc ttcag                                                    15

<210> SEQ ID NO 203
<211> LENGTH: 15
<212> TYPE: DNA
<213> ORGANISM: Human immunodeficiency virus 1

<400> SEQUENCE: 203
tccactgacc ttcag                                                    15

<210> SEQ ID NO 204
<211> LENGTH: 15
<212> TYPE: DNA
<213> ORGANISM: Human immunodeficiency virus 1

<400> SEQUENCE: 204
tccactgacc ttcag                                                    15

<210> SEQ ID NO 205
<211> LENGTH: 15
<212> TYPE: DNA
<213> ORGANISM: Human immunodeficiency virus 1

<400> SEQUENCE: 205
tccactgacc ttcag                                                    15

```
<210> SEQ ID NO 206
<211> LENGTH: 15
<212> TYPE: DNA
<213> ORGANISM: Human immunodeficiency virus 1

<400> SEQUENCE: 206
tccactgacc ttcag                                              15

<210> SEQ ID NO 207
<211> LENGTH: 15
<212> TYPE: DNA
<213> ORGANISM: Human immunodeficiency virus 1

<400> SEQUENCE: 207
tccactgacc ttcag                                              15

<210> SEQ ID NO 208
<211> LENGTH: 15
<212> TYPE: DNA
<213> ORGANISM: Human immunodeficiency virus 1

<400> SEQUENCE: 208
tccactgacc ttcag                                              15

<210> SEQ ID NO 209
<211> LENGTH: 15
<212> TYPE: DNA
<213> ORGANISM: Human immunodeficiency virus 1

<400> SEQUENCE: 209
tccactgacc ttcag                                              15

<210> SEQ ID NO 210
<211> LENGTH: 15
<212> TYPE: DNA
<213> ORGANISM: Human immunodeficiency virus 1

<400> SEQUENCE: 210
tccactgacc ttcag                                              15

<210> SEQ ID NO 211
<211> LENGTH: 15
<212> TYPE: DNA
<213> ORGANISM: Human immunodeficiency virus 1

<400> SEQUENCE: 211
tccactgacc ttcag                                              15

<210> SEQ ID NO 212
<211> LENGTH: 15
<212> TYPE: DNA
<213> ORGANISM: Human immunodeficiency virus 1

<400> SEQUENCE: 212
tccactgacc ttcag                                              15

<210> SEQ ID NO 213
<211> LENGTH: 15
<212> TYPE: DNA
<213> ORGANISM: Human immunodeficiency virus 1

<400> SEQUENCE: 213
tccactgacc ttgag                                              15
```

<210> SEQ ID NO 214
<211> LENGTH: 15
<212> TYPE: DNA
<213> ORGANISM: Human immunodeficiency virus 1

<400> SEQUENCE: 214
tccactgacc ttgag                                                      15

<210> SEQ ID NO 215
<211> LENGTH: 15
<212> TYPE: DNA
<213> ORGANISM: Human immunodeficiency virus 1

<400> SEQUENCE: 215
tccactgacc ttgag                                                      15

<210> SEQ ID NO 216
<211> LENGTH: 15
<212> TYPE: DNA
<213> ORGANISM: Human immunodeficiency virus 1

<400> SEQUENCE: 216
tccactgacc ttgag                                                      15

<210> SEQ ID NO 217
<211> LENGTH: 15
<212> TYPE: DNA
<213> ORGANISM: Human immunodeficiency virus 1

<400> SEQUENCE: 217
tccactgacc ttgag                                                      15

<210> SEQ ID NO 218
<211> LENGTH: 15
<212> TYPE: DNA
<213> ORGANISM: Human immunodeficiency virus 1

<400> SEQUENCE: 218
tccactgacc ttgag                                                      15

<210> SEQ ID NO 219
<211> LENGTH: 15
<212> TYPE: DNA
<213> ORGANISM: Human immunodeficiency virus 1

<400> SEQUENCE: 219
tccactgacc ttgag                                                      15

<210> SEQ ID NO 220
<211> LENGTH: 15
<212> TYPE: DNA
<213> ORGANISM: Human immunodeficiency virus 1

<400> SEQUENCE: 220
tccactgacc ttgag                                                      15

<210> SEQ ID NO 221
<211> LENGTH: 15
<212> TYPE: DNA
<213> ORGANISM: Human immunodeficiency virus 1

<400> SEQUENCE: 221
tccactgacc ttgag                                                      15

```
<210> SEQ ID NO 222
<211> LENGTH: 15
<212> TYPE: DNA
<213> ORGANISM: Human immunodeficiency virus 1

<400> SEQUENCE: 222
tccactgacc tttag                                                    15

<210> SEQ ID NO 223
<211> LENGTH: 15
<212> TYPE: DNA
<213> ORGANISM: Human immunodeficiency virus 1

<400> SEQUENCE: 223
tccactgacc tttag                                                    15

<210> SEQ ID NO 224
<211> LENGTH: 15
<212> TYPE: DNA
<213> ORGANISM: Human immunodeficiency virus 1

<400> SEQUENCE: 224
tccactgacc tttag                                                    15

<210> SEQ ID NO 225
<211> LENGTH: 15
<212> TYPE: DNA
<213> ORGANISM: Human immunodeficiency virus 1

<400> SEQUENCE: 225
tccactgacc tttag                                                    15

<210> SEQ ID NO 226
<211> LENGTH: 15
<212> TYPE: DNA
<213> ORGANISM: Human immunodeficiency virus 1

<400> SEQUENCE: 226
tccactgacc tttag                                                    15

<210> SEQ ID NO 227
<211> LENGTH: 23
<212> TYPE: DNA
<213> ORGANISM: Human immunodeficiency virus 1

<400> SEQUENCE: 227
cagcagttct tgaagtactc cgg                                           23

<210> SEQ ID NO 228
<211> LENGTH: 22
<212> TYPE: DNA
<213> ORGANISM: Human immunodeficiency virus 1

<400> SEQUENCE: 228
agcagttctt gaagtactcc gg                                            22

<210> SEQ ID NO 229
<211> LENGTH: 21
<212> TYPE: DNA
<213> ORGANISM: Human immunodeficiency virus 1

<400> SEQUENCE: 229
```

```
gcagttcttg aagtactccg g                                              21
```

<210> SEQ ID NO 230
<211> LENGTH: 20
<212> TYPE: DNA
<213> ORGANISM: Human immunodeficiency virus 1

<400> SEQUENCE: 230

```
cagttcttga agtactccgg                                                20
```

<210> SEQ ID NO 231
<211> LENGTH: 19
<212> TYPE: DNA
<213> ORGANISM: Human immunodeficiency virus 1

<400> SEQUENCE: 231

```
agttcttgaa gtactccgg                                                 19
```

<210> SEQ ID NO 232
<211> LENGTH: 18
<212> TYPE: DNA
<213> ORGANISM: Human immunodeficiency virus 1

<400> SEQUENCE: 232

```
gttcttgaag tactccgg                                                  18
```

<210> SEQ ID NO 233
<211> LENGTH: 17
<212> TYPE: DNA
<213> ORGANISM: Human immunodeficiency virus 1

<400> SEQUENCE: 233

```
ttcttgaagt actccgg                                                   17
```

<210> SEQ ID NO 234
<211> LENGTH: 16
<212> TYPE: DNA
<213> ORGANISM: Human immunodeficiency virus 1

<400> SEQUENCE: 234

```
tcttgaagta ctccgg                                                    16
```

<210> SEQ ID NO 235
<211> LENGTH: 16
<212> TYPE: DNA
<213> ORGANISM: Human immunodeficiency virus 1

<400> SEQUENCE: 235

```
tcttgaagta ctctag                                                    16
```

<210> SEQ ID NO 236
<211> LENGTH: 15
<212> TYPE: DNA
<213> ORGANISM: Human immunodeficiency virus 1

<400> SEQUENCE: 236

```
cttgaagtac tcagg                                                     15
```

<210> SEQ ID NO 237
<211> LENGTH: 15
<212> TYPE: DNA
<213> ORGANISM: Human immunodeficiency virus 1

<400> SEQUENCE: 237

-continued

```
cttgaagtac tcagg                                                    15

<210> SEQ ID NO 238
<211> LENGTH: 15
<212> TYPE: DNA
<213> ORGANISM: Human immunodeficiency virus 1

<400> SEQUENCE: 238
cttgaagtac tcagg                                                    15

<210> SEQ ID NO 239
<211> LENGTH: 15
<212> TYPE: DNA
<213> ORGANISM: Human immunodeficiency virus 1

<400> SEQUENCE: 239
cttgaagtac tcagg                                                    15

<210> SEQ ID NO 240
<211> LENGTH: 15
<212> TYPE: DNA
<213> ORGANISM: Human immunodeficiency virus 1

<400> SEQUENCE: 240
cttgaagtac tccgg                                                    15

<210> SEQ ID NO 241
<211> LENGTH: 15
<212> TYPE: DNA
<213> ORGANISM: Human immunodeficiency virus 1

<400> SEQUENCE: 241
cttgaagtac tctgg                                                    15

<210> SEQ ID NO 242
<211> LENGTH: 15
<212> TYPE: DNA
<213> ORGANISM: Human immunodeficiency virus 1

<400> SEQUENCE: 242
cttgaagtac tcaag                                                    15

<210> SEQ ID NO 243
<211> LENGTH: 15
<212> TYPE: DNA
<213> ORGANISM: Human immunodeficiency virus 1

<400> SEQUENCE: 243
cttgaagtac tcaag                                                    15

<210> SEQ ID NO 244
<211> LENGTH: 15
<212> TYPE: DNA
<213> ORGANISM: Human immunodeficiency virus 1

<400> SEQUENCE: 244
cttgaagtac tcaag                                                    15

<210> SEQ ID NO 245
<211> LENGTH: 15
<212> TYPE: DNA
<213> ORGANISM: Human immunodeficiency virus 1
```

```
<400> SEQUENCE: 245
cttgaagtac tcaag                                                   15

<210> SEQ ID NO 246
<211> LENGTH: 15
<212> TYPE: DNA
<213> ORGANISM: Human immunodeficiency virus 1

<400> SEQUENCE: 246
cttgaagtac tcaag                                                   15

<210> SEQ ID NO 247
<211> LENGTH: 15
<212> TYPE: DNA
<213> ORGANISM: Human immunodeficiency virus 1

<400> SEQUENCE: 247
cttgaagtac tccag                                                   15

<210> SEQ ID NO 248
<211> LENGTH: 15
<212> TYPE: DNA
<213> ORGANISM: Human immunodeficiency virus 1

<400> SEQUENCE: 248
cttgaagtac tccag                                                   15

<210> SEQ ID NO 249
<211> LENGTH: 15
<212> TYPE: DNA
<213> ORGANISM: Human immunodeficiency virus 1

<400> SEQUENCE: 249
cttgaagtac tccag                                                   15

<210> SEQ ID NO 250
<211> LENGTH: 15
<212> TYPE: DNA
<213> ORGANISM: Human immunodeficiency virus 1

<400> SEQUENCE: 250
cttgaagtac tccag                                                   15

<210> SEQ ID NO 251
<211> LENGTH: 15
<212> TYPE: DNA
<213> ORGANISM: Human immunodeficiency virus 1

<400> SEQUENCE: 251
cttgaagtac tctag                                                   15

<210> SEQ ID NO 252
<211> LENGTH: 15
<212> TYPE: DNA
<213> ORGANISM: Human immunodeficiency virus 1

<400> SEQUENCE: 252
cttgaagtac tctag                                                   15

<210> SEQ ID NO 253
<211> LENGTH: 23
<212> TYPE: DNA
<213> ORGANISM: Human immunodeficiency virus 1
```

```
<400> SEQUENCE: 253
atcagatatc cactgaccttt tgg                                              23

<210> SEQ ID NO 254
<211> LENGTH: 22
<212> TYPE: DNA
<213> ORGANISM: Human immunodeficiency virus 1

<400> SEQUENCE: 254
tcagatatcc actgaccttt gg                                                22

<210> SEQ ID NO 255
<211> LENGTH: 22
<212> TYPE: DNA
<213> ORGANISM: Human immunodeficiency virus 1

<400> SEQUENCE: 255
tcagatatcc actgaccttt gg                                                22

<210> SEQ ID NO 256
<211> LENGTH: 21
<212> TYPE: DNA
<213> ORGANISM: Human immunodeficiency virus 1

<400> SEQUENCE: 256
cagatatcca ctgacctttg g                                                 21

<210> SEQ ID NO 257
<211> LENGTH: 21
<212> TYPE: DNA
<213> ORGANISM: Human immunodeficiency virus 1

<400> SEQUENCE: 257
cagatatcca ctgacctttg g                                                 21

<210> SEQ ID NO 258
<211> LENGTH: 20
<212> TYPE: DNA
<213> ORGANISM: Human immunodeficiency virus 1

<400> SEQUENCE: 258
agatatccac tgacctttgg                                                   20

<210> SEQ ID NO 259
<211> LENGTH: 20
<212> TYPE: DNA
<213> ORGANISM: Human immunodeficiency virus 1

<400> SEQUENCE: 259
agatatccac tgacctttgg                                                   20

<210> SEQ ID NO 260
<211> LENGTH: 19
<212> TYPE: DNA
<213> ORGANISM: Human immunodeficiency virus 1

<400> SEQUENCE: 260
gatatccact gacctttgg                                                    19

<210> SEQ ID NO 261
<211> LENGTH: 19
<212> TYPE: DNA
```

```
<213> ORGANISM: Human immunodeficiency virus 1

<400> SEQUENCE: 261
gatatccact gacctttgg                                          19

<210> SEQ ID NO 262
<211> LENGTH: 18
<212> TYPE: DNA
<213> ORGANISM: Human immunodeficiency virus 1

<400> SEQUENCE: 262
atatccactg acctttgg                                           18

<210> SEQ ID NO 263
<211> LENGTH: 18
<212> TYPE: DNA
<213> ORGANISM: Human immunodeficiency virus 1

<400> SEQUENCE: 263
atatccactg acctttgg                                           18

<210> SEQ ID NO 264
<211> LENGTH: 17
<212> TYPE: DNA
<213> ORGANISM: Human immunodeficiency virus 1

<400> SEQUENCE: 264
tatccactga ccttggg                                            17

<210> SEQ ID NO 265
<211> LENGTH: 17
<212> TYPE: DNA
<213> ORGANISM: Human immunodeficiency virus 1

<400> SEQUENCE: 265
tatccactga cctttgg                                            17

<210> SEQ ID NO 266
<211> LENGTH: 17
<212> TYPE: DNA
<213> ORGANISM: Human immunodeficiency virus 1

<400> SEQUENCE: 266
tatccactga cctttgg                                            17

<210> SEQ ID NO 267
<211> LENGTH: 17
<212> TYPE: DNA
<213> ORGANISM: Human immunodeficiency virus 1

<400> SEQUENCE: 267
tatccactga ccttaag                                            17

<210> SEQ ID NO 268
<211> LENGTH: 17
<212> TYPE: DNA
<213> ORGANISM: Human immunodeficiency virus 1

<400> SEQUENCE: 268
tatccactga ccttgag                                            17

<210> SEQ ID NO 269
<211> LENGTH: 16
```

<212> TYPE: DNA
<213> ORGANISM: Human immunodeficiency virus 1

<400> SEQUENCE: 269
atccactgac cttagg                                              16

<210> SEQ ID NO 270
<211> LENGTH: 16
<212> TYPE: DNA
<213> ORGANISM: Human immunodeficiency virus 1

<400> SEQUENCE: 270
atccactgac cttagg                                              16

<210> SEQ ID NO 271
<211> LENGTH: 16
<212> TYPE: DNA
<213> ORGANISM: Human immunodeficiency virus 1

<400> SEQUENCE: 271
atccactgac cttggg                                              16

<210> SEQ ID NO 272
<211> LENGTH: 16
<212> TYPE: DNA
<213> ORGANISM: Human immunodeficiency virus 1

<400> SEQUENCE: 272
atccactgac cttggg                                              16

<210> SEQ ID NO 273
<211> LENGTH: 16
<212> TYPE: DNA
<213> ORGANISM: Human immunodeficiency virus 1

<400> SEQUENCE: 273
atccactgac cttggg                                              16

<210> SEQ ID NO 274
<211> LENGTH: 16
<212> TYPE: DNA
<213> ORGANISM: Human immunodeficiency virus 1

<400> SEQUENCE: 274
atccactgac cttggg                                              16

<210> SEQ ID NO 275
<211> LENGTH: 16
<212> TYPE: DNA
<213> ORGANISM: Human immunodeficiency virus 1

<400> SEQUENCE: 275
atccactgac ctttgg                                              16

<210> SEQ ID NO 276
<211> LENGTH: 16
<212> TYPE: DNA
<213> ORGANISM: Human immunodeficiency virus 1

<400> SEQUENCE: 276
atccactgac ctttgg                                              16

<210> SEQ ID NO 277

```
<211> LENGTH: 16
<212> TYPE: DNA
<213> ORGANISM: Human immunodeficiency virus 1

<400> SEQUENCE: 277
atccactgac ctttgg                                                          16

<210> SEQ ID NO 278
<211> LENGTH: 16
<212> TYPE: DNA
<213> ORGANISM: Human immunodeficiency virus 1

<400> SEQUENCE: 278
atccactgac cttaag                                                          16

<210> SEQ ID NO 279
<211> LENGTH: 16
<212> TYPE: DNA
<213> ORGANISM: Human immunodeficiency virus 1

<400> SEQUENCE: 279
atccactgac cttaag                                                          16

<210> SEQ ID NO 280
<211> LENGTH: 16
<212> TYPE: DNA
<213> ORGANISM: Human immunodeficiency virus 1

<400> SEQUENCE: 280
atccactgac cttcag                                                          16

<210> SEQ ID NO 281
<211> LENGTH: 16
<212> TYPE: DNA
<213> ORGANISM: Human immunodeficiency virus 1

<400> SEQUENCE: 281
atccactgac cttcag                                                          16

<210> SEQ ID NO 282
<211> LENGTH: 16
<212> TYPE: DNA
<213> ORGANISM: Human immunodeficiency virus 1

<400> SEQUENCE: 282
atccactgac cttgag                                                          16

<210> SEQ ID NO 283
<211> LENGTH: 16
<212> TYPE: DNA
<213> ORGANISM: Human immunodeficiency virus 1

<400> SEQUENCE: 283
atccactgac cttgag                                                          16

<210> SEQ ID NO 284
<211> LENGTH: 15
<212> TYPE: DNA
<213> ORGANISM: Human immunodeficiency virus 1

<400> SEQUENCE: 284
tccactgacc ttagg                                                           15
```

```
<210> SEQ ID NO 285
<211> LENGTH: 15
<212> TYPE: DNA
<213> ORGANISM: Human immunodeficiency virus 1

<400> SEQUENCE: 285
tccactgacc ttagg                                                      15

<210> SEQ ID NO 286
<211> LENGTH: 15
<212> TYPE: DNA
<213> ORGANISM: Human immunodeficiency virus 1

<400> SEQUENCE: 286
tccactgacc ttagg                                                      15

<210> SEQ ID NO 287
<211> LENGTH: 15
<212> TYPE: DNA
<213> ORGANISM: Human immunodeficiency virus 1

<400> SEQUENCE: 287
tccactgacc ttagg                                                      15

<210> SEQ ID NO 288
<211> LENGTH: 15
<212> TYPE: DNA
<213> ORGANISM: Human immunodeficiency virus 1

<400> SEQUENCE: 288
tccactgacc ttagg                                                      15

<210> SEQ ID NO 289
<211> LENGTH: 15
<212> TYPE: DNA
<213> ORGANISM: Human immunodeficiency virus 1

<400> SEQUENCE: 289
tccactgacc ttagg                                                      15

<210> SEQ ID NO 290
<211> LENGTH: 15
<212> TYPE: DNA
<213> ORGANISM: Human immunodeficiency virus 1

<400> SEQUENCE: 290
tccactgacc ttggg                                                      15

<210> SEQ ID NO 291
<211> LENGTH: 15
<212> TYPE: DNA
<213> ORGANISM: Human immunodeficiency virus 1

<400> SEQUENCE: 291
tccactgacc ttggg                                                      15

<210> SEQ ID NO 292
<211> LENGTH: 15
<212> TYPE: DNA
<213> ORGANISM: Human immunodeficiency virus 1

<400> SEQUENCE: 292
tccactgacc ttggg                                                      15
```

<210> SEQ ID NO 293
<211> LENGTH: 15
<212> TYPE: DNA
<213> ORGANISM: Human immunodeficiency virus 1

<400> SEQUENCE: 293
tccactgacc ttggg                                                    15

<210> SEQ ID NO 294
<211> LENGTH: 15
<212> TYPE: DNA
<213> ORGANISM: Human immunodeficiency virus 1

<400> SEQUENCE: 294
tccactgacc ttggg                                                    15

<210> SEQ ID NO 295
<211> LENGTH: 15
<212> TYPE: DNA
<213> ORGANISM: Human immunodeficiency virus 1

<400> SEQUENCE: 295
tccactgacc ttggg                                                    15

<210> SEQ ID NO 296
<211> LENGTH: 15
<212> TYPE: DNA
<213> ORGANISM: Human immunodeficiency virus 1

<400> SEQUENCE: 296
tccactgacc ttggg                                                    15

<210> SEQ ID NO 297
<211> LENGTH: 15
<212> TYPE: DNA
<213> ORGANISM: Human immunodeficiency virus 1

<400> SEQUENCE: 297
tccactgacc ttggg                                                    15

<210> SEQ ID NO 298
<211> LENGTH: 15
<212> TYPE: DNA
<213> ORGANISM: Human immunodeficiency virus 1

<400> SEQUENCE: 298
tccactgacc tttgg                                                    15

<210> SEQ ID NO 299
<211> LENGTH: 15
<212> TYPE: DNA
<213> ORGANISM: Human immunodeficiency virus 1

<400> SEQUENCE: 299
tccactgacc tttgg                                                    15

<210> SEQ ID NO 300
<211> LENGTH: 15
<212> TYPE: DNA
<213> ORGANISM: Human immunodeficiency virus 1

<400> SEQUENCE: 300
tccactgacc tttgg                                                    15

<210> SEQ ID NO 301
<211> LENGTH: 15
<212> TYPE: DNA
<213> ORGANISM: Human immunodeficiency virus 1

<400> SEQUENCE: 301
tccactgacc tttgg                                                    15

<210> SEQ ID NO 302
<211> LENGTH: 15
<212> TYPE: DNA
<213> ORGANISM: Human immunodeficiency virus 1

<400> SEQUENCE: 302
tccactgacc tttgg                                                    15

<210> SEQ ID NO 303
<211> LENGTH: 15
<212> TYPE: DNA
<213> ORGANISM: Human immunodeficiency virus 1

<400> SEQUENCE: 303
tccactgacc tttgg                                                    15

<210> SEQ ID NO 304
<211> LENGTH: 15
<212> TYPE: DNA
<213> ORGANISM: Human immunodeficiency virus 1

<400> SEQUENCE: 304
tccactgacc tttgg                                                    15

<210> SEQ ID NO 305
<211> LENGTH: 15
<212> TYPE: DNA
<213> ORGANISM: Human immunodeficiency virus 1

<400> SEQUENCE: 305
tccactgacc tttgg                                                    15

<210> SEQ ID NO 306
<211> LENGTH: 15
<212> TYPE: DNA
<213> ORGANISM: Human immunodeficiency virus 1

<400> SEQUENCE: 306
tccactgacc tttgg                                                    15

<210> SEQ ID NO 307
<211> LENGTH: 15
<212> TYPE: DNA
<213> ORGANISM: Human immunodeficiency virus 1

<400> SEQUENCE: 307
tccactgacc ttaag                                                    15

<210> SEQ ID NO 308
<211> LENGTH: 15
<212> TYPE: DNA
<213> ORGANISM: Human immunodeficiency virus 1

<400> SEQUENCE: 308
tccactgacc ttaag                                                        15

<210> SEQ ID NO 309
<211> LENGTH: 15
<212> TYPE: DNA
<213> ORGANISM: Human immunodeficiency virus 1

<400> SEQUENCE: 309
tccactgacc ttaag                                                        15

<210> SEQ ID NO 310
<211> LENGTH: 15
<212> TYPE: DNA
<213> ORGANISM: Human immunodeficiency virus 1

<400> SEQUENCE: 310
tccactgacc ttaag                                                        15

<210> SEQ ID NO 311
<211> LENGTH: 15
<212> TYPE: DNA
<213> ORGANISM: Human immunodeficiency virus 1

<400> SEQUENCE: 311
tccactgacc ttaag                                                        15

<210> SEQ ID NO 312
<211> LENGTH: 15
<212> TYPE: DNA
<213> ORGANISM: Human immunodeficiency virus 1

<400> SEQUENCE: 312
tccactgacc ttcag                                                        15

<210> SEQ ID NO 313
<211> LENGTH: 15
<212> TYPE: DNA
<213> ORGANISM: Human immunodeficiency virus 1

<400> SEQUENCE: 313
tccactgacc ttcag                                                        15

<210> SEQ ID NO 314
<211> LENGTH: 15
<212> TYPE: DNA
<213> ORGANISM: Human immunodeficiency virus 1

<400> SEQUENCE: 314
tccactgacc ttcag                                                        15

<210> SEQ ID NO 315
<211> LENGTH: 15
<212> TYPE: DNA
<213> ORGANISM: Human immunodeficiency virus 1

<400> SEQUENCE: 315
tccactgacc ttcag                                                        15

<210> SEQ ID NO 316
<211> LENGTH: 15
<212> TYPE: DNA
<213> ORGANISM: Human immunodeficiency virus 1

<400> SEQUENCE: 316
tccactgacc ttcag                                                          15

<210> SEQ ID NO 317
<211> LENGTH: 15
<212> TYPE: DNA
<213> ORGANISM: Human immunodeficiency virus 1

<400> SEQUENCE: 317
tccactgacc ttcag                                                          15

<210> SEQ ID NO 318
<211> LENGTH: 15
<212> TYPE: DNA
<213> ORGANISM: Human immunodeficiency virus 1

<400> SEQUENCE: 318
tccactgacc ttcag                                                          15

<210> SEQ ID NO 319
<211> LENGTH: 15
<212> TYPE: DNA
<213> ORGANISM: Human immunodeficiency virus 1

<400> SEQUENCE: 319
tccactgacc ttcag                                                          15

<210> SEQ ID NO 320
<211> LENGTH: 15
<212> TYPE: DNA
<213> ORGANISM: Human immunodeficiency virus 1

<400> SEQUENCE: 320
tccactgacc ttcag                                                          15

<210> SEQ ID NO 321
<211> LENGTH: 15
<212> TYPE: DNA
<213> ORGANISM: Human immunodeficiency virus 1

<400> SEQUENCE: 321
tccactgacc ttcag                                                          15

<210> SEQ ID NO 322
<211> LENGTH: 15
<212> TYPE: DNA
<213> ORGANISM: Human immunodeficiency virus 1

<400> SEQUENCE: 322
tccactgacc ttcag                                                          15

<210> SEQ ID NO 323
<211> LENGTH: 15
<212> TYPE: DNA
<213> ORGANISM: Human immunodeficiency virus 1

<400> SEQUENCE: 323
tccactgacc ttcag                                                          15

<210> SEQ ID NO 324
<211> LENGTH: 15
<212> TYPE: DNA
<213> ORGANISM: Human immunodeficiency virus 1

<400> SEQUENCE: 324
tccactgacc ttgag                                                        15

<210> SEQ ID NO 325
<211> LENGTH: 15
<212> TYPE: DNA
<213> ORGANISM: Human immunodeficiency virus 1

<400> SEQUENCE: 325
tccactgacc ttgag                                                        15

<210> SEQ ID NO 326
<211> LENGTH: 15
<212> TYPE: DNA
<213> ORGANISM: Human immunodeficiency virus 1

<400> SEQUENCE: 326
tccactgacc ttgag                                                        15

<210> SEQ ID NO 327
<211> LENGTH: 15
<212> TYPE: DNA
<213> ORGANISM: Human immunodeficiency virus 1

<400> SEQUENCE: 327
tccactgacc ttgag                                                        15

<210> SEQ ID NO 328
<211> LENGTH: 15
<212> TYPE: DNA
<213> ORGANISM: Human immunodeficiency virus 1

<400> SEQUENCE: 328
tccactgacc ttgag                                                        15

<210> SEQ ID NO 329
<211> LENGTH: 15
<212> TYPE: DNA
<213> ORGANISM: Human immunodeficiency virus 1

<400> SEQUENCE: 329
tccactgacc ttgag                                                        15

<210> SEQ ID NO 330
<211> LENGTH: 15
<212> TYPE: DNA
<213> ORGANISM: Human immunodeficiency virus 1

<400> SEQUENCE: 330
tccactgacc ttgag                                                        15

<210> SEQ ID NO 331
<211> LENGTH: 15
<212> TYPE: DNA
<213> ORGANISM: Human immunodeficiency virus 1

<400> SEQUENCE: 331
tccactgacc ttgag                                                        15

<210> SEQ ID NO 332
<211> LENGTH: 15
<212> TYPE: DNA
<213> ORGANISM: Human immunodeficiency virus 1

<400> SEQUENCE: 332
tccactgacc ttgag                                                          15

<210> SEQ ID NO 333
<211> LENGTH: 15
<212> TYPE: DNA
<213> ORGANISM: Human immunodeficiency virus 1

<400> SEQUENCE: 333
tccactgacc tttag                                                          15

<210> SEQ ID NO 334
<211> LENGTH: 15
<212> TYPE: DNA
<213> ORGANISM: Human immunodeficiency virus 1

<400> SEQUENCE: 334
tccactgacc tttag                                                          15

<210> SEQ ID NO 335
<211> LENGTH: 15
<212> TYPE: DNA
<213> ORGANISM: Human immunodeficiency virus 1

<400> SEQUENCE: 335
tccactgacc tttag                                                          15

<210> SEQ ID NO 336
<211> LENGTH: 15
<212> TYPE: DNA
<213> ORGANISM: Human immunodeficiency virus 1

<400> SEQUENCE: 336
tccactgacc tttag                                                          15

<210> SEQ ID NO 337
<211> LENGTH: 15
<212> TYPE: DNA
<213> ORGANISM: Human immunodeficiency virus 1

<400> SEQUENCE: 337
tccactgacc tttag                                                          15

<210> SEQ ID NO 338
<211> LENGTH: 23
<212> TYPE: DNA
<213> ORGANISM: Human immunodeficiency virus 1

<400> SEQUENCE: 338
cagcagttct tgaagtactc cgg                                                 23

<210> SEQ ID NO 339
<211> LENGTH: 22
<212> TYPE: DNA
<213> ORGANISM: Human immunodeficiency virus 1

<400> SEQUENCE: 339
agcagttctt gaagtactcc gg                                                  22

<210> SEQ ID NO 340
<211> LENGTH: 21
<212> TYPE: DNA

```
<213> ORGANISM: Human immunodeficiency virus 1

<400> SEQUENCE: 340
gcagttcttg aagtactccg g                                         21

<210> SEQ ID NO 341
<211> LENGTH: 20
<212> TYPE: DNA
<213> ORGANISM: Human immunodeficiency virus 1

<400> SEQUENCE: 341
cagttcttga agtactccgg                                           20

<210> SEQ ID NO 342
<211> LENGTH: 19
<212> TYPE: DNA
<213> ORGANISM: Human immunodeficiency virus 1

<400> SEQUENCE: 342
agttcttgaa gtactccgg                                            19

<210> SEQ ID NO 343
<211> LENGTH: 18
<212> TYPE: DNA
<213> ORGANISM: Human immunodeficiency virus 1

<400> SEQUENCE: 343
gttcttgaag tactccgg                                             18

<210> SEQ ID NO 344
<211> LENGTH: 17
<212> TYPE: DNA
<213> ORGANISM: Human immunodeficiency virus 1

<400> SEQUENCE: 344
ttcttgaagt actccgg                                              17

<210> SEQ ID NO 345
<211> LENGTH: 16
<212> TYPE: DNA
<213> ORGANISM: Human immunodeficiency virus 1

<400> SEQUENCE: 345
tcttgaagta ctccgg                                               16

<210> SEQ ID NO 346
<211> LENGTH: 16
<212> TYPE: DNA
<213> ORGANISM: Human immunodeficiency virus 1

<400> SEQUENCE: 346
tcttgaagta ctctag                                               16

<210> SEQ ID NO 347
<211> LENGTH: 15
<212> TYPE: DNA
<213> ORGANISM: Human immunodeficiency virus 1

<400> SEQUENCE: 347
cttgaagtac tcagg                                                15

<210> SEQ ID NO 348
<211> LENGTH: 15
```

```
<212> TYPE: DNA
<213> ORGANISM: Human immunodeficiency virus 1

<400> SEQUENCE: 348
cttgaagtac tcagg                                                  15

<210> SEQ ID NO 349
<211> LENGTH: 15
<212> TYPE: DNA
<213> ORGANISM: Human immunodeficiency virus 1

<400> SEQUENCE: 349
cttgaagtac tcagg                                                  15

<210> SEQ ID NO 350
<211> LENGTH: 15
<212> TYPE: DNA
<213> ORGANISM: Human immunodeficiency virus 1

<400> SEQUENCE: 350
cttgaagtac tcagg                                                  15

<210> SEQ ID NO 351
<211> LENGTH: 15
<212> TYPE: DNA
<213> ORGANISM: Human immunodeficiency virus 1

<400> SEQUENCE: 351
cttgaagtac tccgg                                                  15

<210> SEQ ID NO 352
<211> LENGTH: 15
<212> TYPE: DNA
<213> ORGANISM: Human immunodeficiency virus 1

<400> SEQUENCE: 352
cttgaagtac tctgg                                                  15

<210> SEQ ID NO 353
<211> LENGTH: 15
<212> TYPE: DNA
<213> ORGANISM: Human immunodeficiency virus 1

<400> SEQUENCE: 353
cttgaagtac tcaag                                                  15

<210> SEQ ID NO 354
<211> LENGTH: 15
<212> TYPE: DNA
<213> ORGANISM: Human immunodeficiency virus 1

<400> SEQUENCE: 354
cttgaagtac tcaag                                                  15

<210> SEQ ID NO 355
<211> LENGTH: 15
<212> TYPE: DNA
<213> ORGANISM: Human immunodeficiency virus 1

<400> SEQUENCE: 355
cttgaagtac tcaag                                                  15

<210> SEQ ID NO 356
```

-continued

<210> SEQ ID NO 357
<211> LENGTH: 15
<212> TYPE: DNA
<213> ORGANISM: Human immunodeficiency virus 1

<400> SEQUENCE: 356
cttgaagtac tcaag                                                    15

<210> SEQ ID NO 357
<211> LENGTH: 15
<212> TYPE: DNA
<213> ORGANISM: Human immunodeficiency virus 1

<400> SEQUENCE: 357
cttgaagtac tcaag                                                    15

<210> SEQ ID NO 358
<211> LENGTH: 15
<212> TYPE: DNA
<213> ORGANISM: Human immunodeficiency virus 1

<400> SEQUENCE: 358
cttgaagtac tccag                                                    15

<210> SEQ ID NO 359
<211> LENGTH: 15
<212> TYPE: DNA
<213> ORGANISM: Human immunodeficiency virus 1

<400> SEQUENCE: 359
cttgaagtac tccag                                                    15

<210> SEQ ID NO 360
<211> LENGTH: 15
<212> TYPE: DNA
<213> ORGANISM: Human immunodeficiency virus 1

<400> SEQUENCE: 360
cttgaagtac tccag                                                    15

<210> SEQ ID NO 361
<211> LENGTH: 15
<212> TYPE: DNA
<213> ORGANISM: Human immunodeficiency virus 1

<400> SEQUENCE: 361
cttgaagtac tccag                                                    15

<210> SEQ ID NO 362
<211> LENGTH: 15
<212> TYPE: DNA
<213> ORGANISM: Human immunodeficiency virus 1

<400> SEQUENCE: 362
cttgaagtac tctag                                                    15

<210> SEQ ID NO 363
<211> LENGTH: 15
<212> TYPE: DNA
<213> ORGANISM: Human immunodeficiency virus 1

<400> SEQUENCE: 363
cttgaagtac tctag                                                    15

-continued

```
<210> SEQ ID NO 364
<211> LENGTH: 23
<212> TYPE: DNA
<213> ORGANISM: Human immunodeficiency virus 1

<400> SEQUENCE: 364
gatctgtgga tctaccacac aca                                          23

<210> SEQ ID NO 365
<211> LENGTH: 26
<212> TYPE: DNA
<213> ORGANISM: Human immunodeficiency virus 1

<400> SEQUENCE: 365
gatctgtgga tctaccacac acaagg                                       26

<210> SEQ ID NO 366
<211> LENGTH: 20
<212> TYPE: DNA
<213> ORGANISM: Human immunodeficiency virus 1

<400> SEQUENCE: 366
gattggcaga actacacacc                                              20

<210> SEQ ID NO 367
<211> LENGTH: 23
<212> TYPE: DNA
<213> ORGANISM: Human immunodeficiency virus 1

<400> SEQUENCE: 367
gattggcaga actacacacc agg                                          23

<210> SEQ ID NO 368
<211> LENGTH: 27
<212> TYPE: DNA
<213> ORGANISM: Human immunodeficiency virus 1

<400> SEQUENCE: 368
gccagggatc agatatccac tgacctt                                      27

<210> SEQ ID NO 369
<211> LENGTH: 30
<212> TYPE: DNA
<213> ORGANISM: Human immunodeficiency virus 1

<400> SEQUENCE: 369
gccagggatc agatatccac tgacctttgg                                   30

<210> SEQ ID NO 370
<211> LENGTH: 30
<212> TYPE: DNA
<213> ORGANISM: Human immunodeficiency virus 1

<400> SEQUENCE: 370
gagtacttca agaactgctg acatcgagct                                   30

<210> SEQ ID NO 371
<211> LENGTH: 33
<212> TYPE: DNA
<213> ORGANISM: Human immunodeficiency virus 1

<400> SEQUENCE: 371
ccggagtact tcaagaactg ctgacatcga gct                               33
```

<210> SEQ ID NO 372
<211> LENGTH: 20
<212> TYPE: DNA
<213> ORGANISM: Human immunodeficiency virus 1

<400> SEQUENCE: 372
gcgtggcctg ggcgggactg                                                 20

<210> SEQ ID NO 373
<211> LENGTH: 23
<212> TYPE: DNA
<213> ORGANISM: Human immunodeficiency virus 1

<400> SEQUENCE: 373
gcgtggcctg ggcgggactg ggg                                             23

<210> SEQ ID NO 374
<211> LENGTH: 22
<212> TYPE: DNA
<213> ORGANISM: Human immunodeficiency virus 1

<400> SEQUENCE: 374
tcagatgctg catataagca gc                                              22

<210> SEQ ID NO 375
<211> LENGTH: 25
<212> TYPE: DNA
<213> ORGANISM: Human immunodeficiency virus 1

<400> SEQUENCE: 375
ccctcagatg ctgcatataa gcagc                                           25

<210> SEQ ID NO 376
<211> LENGTH: 634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376
tggaagggct aattcactcc caacgaagac aagatatcct tgatctgtgg atctaccaca      60
cacaaggcta cttccctgat ggcagaact acacaccagg gccagggatc agatatccac      120
tgacctttgg atggtgctac aagctagtac cagttgagca agagaaggta gaagaagcca      180
atgaaggaga gaacacccgc ttgttacacc ctgtgagcct gcatgggatg gatgacccgg      240
agagagaagt attagagtgg aggtttgaca gccgcctagc atttcatcac atggcccgag      300
agctgcatcc ggagtacttc aagaactgct gacatcgagc ttgctacaag gactttccg       360 ctggggactt tccagggagg cgtggcctgg gcgggactgg ggagtggcga gccctcagat      420
gctgcatata agcagctgct ttttgcttgt actgggtctc tctggttaga ccagatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600
agaccctttt agtcagtgtg aaaatctct agca                                  634

<210> SEQ ID NO 377
<211> LENGTH: 453
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 377

```
tggaagggct aattcactcc caacgaagac aagatatcct tgatctgtgg atctaccaca      60
cacaaggcta cttccctgat tggcagaact acacaccagg gccagggatc agatatccac     120
tgacctttgg atggtgctac aagctagtac cagttgagca agagaaggta gaagaagcca     180
atgaaggaga gaacacccgc ttgttacacc ctgtgagcct gcatgggatg gatgacccgg     240
agagagaagt attagagtgg aggtttgaca gccgcctagc atttcatcac atggcccgag     300
agctgcatcc ggagtacttc aagaactgct gacatcgagc ttgctacaag ggactttccg     360
ctggggactt tccagggagg cgtggcctgg gcgggactgg ggagtggcga gccctcagat     420
gctgcatata agcagctgct ttttgcttgt act                                   453
```

<210> SEQ ID NO 378
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378

```
gggtctctct ggttagacca gatctgagcc tgggagctct ctggctaact agggaaccca      60
ctgcttaagc ctcaataaag cttgccttga gtgcttc                               97
```

<210> SEQ ID NO 379
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379

```
aagtagtgtg tgcccgtctg ttgtgtgact ctggtaacta gagatccctc agacccttt      60
agtcagtgtg gaaaatctct agca                                             84
```

<210> SEQ ID NO 380
<211> LENGTH: 818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 380

```
tggaagggat ttattacagt gcaagaagac atagaatctt agacatatac ttagaaaagg      60
aagaaggcat cataccagat tggcaggatt acacctcagg accaggaatt agatacccaa     120
agacatttgg ctggctatgg aaattagtcc ctgtaaatgt atcagatgag gcacaggagg     180
atgaggagca ttatttaatg catccagctc aaacttccca gtgggatgac ccttggggag     240
aggttctagc atggaagttt gatccaactc tggcctacac ttatgaggca tatgttagat     300
acccagaaga gtttggaagc aagtcaggcc tgtcagagga agaggttaga agaaggctaa     360
ccgcaagagg ccttcttaac atggctgaca gaaggaaac tcgctgaaac agcagggact     420
ttccacaagg ggatgttacg gggaggtact ggggaggagc cggtcgggaa cgcccacttt     480
cttgatgtat aaatatcact gcatttcgct ctgtattcag tcgctctgcg gagaggctgg     540
```

```
cagattgagc cctgggaggt tctctccagc actagcaggt agagcctggg tgttccctgc      600
tagactctca ccagcacttg gccggtgctg ggcagagtga ctccacgctt gcttgcttaa      660
agccctcttc aataaagctg ccattttaga agtaagctag tgtgtgttcc catctctcct      720
agccgccgcc tggtcaactc ggtactcaat aataagaaga ccctggtctg ttaggaccct      780
ttctgctttg ggaaaccgaa gcaggaaaat ccctagca                              818

<210> SEQ ID NO 381
<211> LENGTH: 517
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 381
tggaagggat ttattacagt gcaagaagac atagaatctt agacatatac ttagaaaagg       60
aagaaggcat cataccagat tggcaggatt acacctcagg accaggaatt agatacccaa      120
agacatttgg ctggctatgg aaattagtcc ctgtaaatgt atcagatgag gcacaggagg      180
atgaggagca ttatttaatg catccagctc aaacttccca gtgggatgac ccttggggag      240
aggttctagc atggaagttt gatccaactc tggcctacac ttatgaggca tatgttagat      300
acccagaaga gtttggaagc aagtcaggcc tgtcagagga agaggttaga agaaggctaa      360
ccgcaagagg ccttcttaac atggctgaca agaaggaaac tcgctgaaac agcagggact      420
ttccacaagg ggatgttacg gggaggtact ggggaggagc cggtcgggaa cgcccacttt      480
cttgatgtat aaatatcact gcatttcgct ctgtatt                               517

<210> SEQ ID NO 382
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 382
cagtcgctct gcggagaggc tggcagattg agccctggga ggttctctcc agcactagca       60
ggtagagcct gggtgttccc tgctagactc tcaccagcac ttggccggtg ctgggcagag      120
tgactccacg cttgcttgct aaagccctc ttcaataaag ctgccatttt agaagt           176

<210> SEQ ID NO 383
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 383
aagctagtgt gtgttcccat ctctcctagc cgccgcctgg tcaactcggt actcaataat       60
aagaagaccc tggtctgtta ggaccctttc tgctttggga aaccgaagca ggaaaatccc      120
tagca                                                                  125

<210> SEQ ID NO 384
<211> LENGTH: 14825
<212> TYPE: DNA
<213> ORGANISM: Human immunodeficiency virus 1
```

<400> SEQUENCE: 384

```
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
atgaaggaga gaacaacagc ttgttacacc ctatgagcca gcatgggatg gaggacccgg     240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccaggggag gtgtggcctg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata aagcttgcct     540
tgagtgctca aagtagtgtg tgcccgtctg ttgtgtgact ctggtaacta gagatccctc     600
agaccctttt agtcagtgtg gaaaatctct agcagtggcg cccgaacagg gacttgaaag     660
cgaaagtaaa gccagaggag atctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcggta ttaagcgggg gagaattaga taaatgggaa     840
aaaattcggt taaggccagg gggaagaaa caatataaac taaaacatat agtatgggca     900
agcagggagc tagaacgatt cgcagttaat cctggccttt tagagacatc agaaggctgt     960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200
ctccaggggc aaatggtaca tcaggccata tcacctagaa ctttaaatgc atgggtaaaa    1260
gtagtagaag agaaggcttt cagcccagaa gtaatacccca tgttttcagc attatcagaa    1320
ggagccaccc cacaagattt aaataccatg ctaaacacag tggggggaca tcaagcagcc    1380
atgcaaatgt taaaagagac catcaatgag gaagctgcag aatgggatag attgcatcca    1440
gtgcatgcag ggcctattgc accaggccag atgagagaac caaggggaag tgacatagca    1500
ggaactacta gtacccttca ggaacaaata ggatggatga cacataatcc acctatccca    1560
gtaggagaaa tctataaaag atggataatc ctgggattaa ataaaatagt aagaatgtat    1620
agccctacca gcattctgga cataagacaa ggaccaaagg aacccttag agactatgta    1680
gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga agaaatgatg acagcatgtc agggagtggg gggacccggc    1860
cataaagcaa gagttttggc tgaagcaatg agccaagtaa caaatccagc taccataatg    1920
atacagaaag gcaattttag gaaccaaaga aagactgtta agtgtttcaa ttgtggcaaa    1980
gaagggcaca tagccaaaaa ttgcagggcc cctaggaaaa agggctgttg gaaatgtgga    2040
aaggaaggac accaaatgaa agattgtact gagagacagg ctaattttt agggaagatc    2100
tggccttccc acaagggaag gccagggaat tttcttcaga gcagaccaga gccaacagcc    2160
ccaccagaag agagcttcag gtttggggaa gagacaacaa ctccctctca gaagcaggag    2220
ccgatagaca aggaactgta tcctttagct tccctcagat cactctttgg cagcgacccc    2280
```

```
tcgtcacaat aaagataggg gggcaattaa aggaagctct attagataca ggagcagatg   2340
atacagtatt agaagaaatg aatttgccag gaagatggaa accaaaaatg ataggggaa    2400 ttggaggttt tatcaaagta agacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180 ggtgggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaagta tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aatacccctc ccttagtgaa gttatggtac cagttagaga   3840
aagaacccat aataggagca gaaacttttct atgtagatgg ggcagccaat agggaaacta   3900
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagataaat   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatcct ggtagcagtt catgtagcca gtggatatat agaagcagaa gttattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
```

```
tagaatctat gaataaagaa ttaaagaaaa ttataggaca ggtaagagat caggctgaac    4740
atcttaagac agcagtacaa atggcagtat tcatccacaa ttttaaaaga aaagggggga    4800
ttgggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gttttttcaga atctgctata    5400
agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggacactaga gcttttagag gaacttaaga    5640
gtgaagctgt tagacatttt cctaggatat ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcagaat aggcgttact cgacagagga    5820
gagcaagaaa tggagccagt agatcctaga ctagagccct ggaagcatcc aggaagtcag    5880
cctaaaactg cttgtaccaa ttgctattgt aaaaagtgtt gctttcattg ccaagtttgt    5940
ttcatgacaa agccttaggc atctcctat ggcaggaaga agcggagaca gcgacgaaga    6000
gctcatcaga acagtcagac tcatcaagct tctctatcaa agcagtaagt agtacatgta    6060
atgcaaccta ataatagc aatagtagca ttagtagtag caataataat agcaatagtt    6120
gtgtggtcca tagtaatcat agaatatagg aaaatattaa gacaaagaaa aatagacagg    6180
ttaattgata gactaataga aagagcagaa gacagtggca atgagagtga aggagaagta    6240
tcagcacttg tggagatggg ggtggaaatg gggcaccatg ctccttggga tattgatgat    6300
ctgtagtgct acagaaaaat tgtgggtcac agtctattat ggggtacctg tgtggaagga    6360
agcaaccacc actctatttt gtgcatcaga tgctaaagca tatgatacag aggtacataa    6420
tgtttgggcc acacatgcct gtgtacccac agaccccaac ccacaagaag tagtattggt    6480
aaatgtgaca gaaaatttta acatgtggaa aaatgacatg gtagaacaga tgcatgagga    6540
tataatcagt ttatgggatc aaagcctaaa gccatgtgta aaattaaccc cactctgtgt    6600
tagtttaaag tgcactgatt tgaagaatga tactaatacc aatagtagta gcgggagaat    6660
gataatggag aaaggagaga taaaaaactg ctctttcaat atcagcacaa gcataagaga    6720
taaggtgcag aaagaatatg cattcttta taaacttgat atagtaccaa tagataatac    6780
cagctatagg ttgataagtt gtaacacctc agtcattaca caggcctgtc caaaggtatc    6840
ctttgagcca attcccatac attattgtgc cccggctggt tttgcgattc taaaatgtaa    6900
taataagacg ttcaatggaa caggaccatg tacaaatgtc agcacagtac aatgtacaca    6960
tggaatcagg ccagtagtat caactcaact gctgttaaat ggcagtctag cagaagaaga    7020
```

```
tgtagtaatt agatctgcca atttcacaga caatgctaaa accataatag tacagctgaa      7080
cacatctgta gaaattaatt gtacaagacc caacaacaat acaagaaaaa gtatccgtat      7140
ccagagggga ccagggagag catttgttac aataggaaaa ataggaaata tgagacaagc      7200
acattgtaac attagtagag caaaatggaa tgccacttta aaacagatag ctagcaaatt      7260
aagagaacaa tttggaaata ataaaacaat aatctttaag caatcctcag gaggggaccc      7320
agaaattgta acgcacagtt ttaattgtgg aggggaattt ttctactgta attcaacaca      7380
actgtttaat agtacttggt ttaatagtac ttggagtact gaagggtcaa ataacactga      7440
aggaagtgac acaatcacac tcccatgcag aataaaacaa tttataaaca tgtggcagga      7500
agtaggaaaa gcaatgtatg cccctcccat cagtggacaa attagatgtt catcaaatat      7560
tactgggctg ctattaacaa gagatggtgg taataacaac aatgggtccg agatcttcag      7620
acctggagga ggcgatatga gggacaattg gagaagtgaa ttatataaat ataaagtagt      7680
aaaaattgaa ccattaggag tagcacccac caaggcaaag agaagagtgg tgcagagaga      7740
aaaaagagca gtgggaatag gagctttgtt ccttgggttc ttgggagcag caggaagcac      7800
tatgggcgca gcgtcaatga cgctgacggt acaggccaga caattattgt ctgatatagt      7860
gcagcagcag aacaatttgc tgagggctat tgaggcgcaa cagcatctgt tgcaactcac      7920
agtctggggc atcaaacagc tccaggcaag aatcctggct gtggaaagat acctaaagga      7980
tcaacagctc ctggggattt ggggttgctc tggaaaactc atttgcacca ctgctgtgcc      8040
ttggaatgct agttggagta ataaatctct ggaacagatt tggaataaca tgacctggat      8100
ggagtgggac agagaaatta acaattacac aagcttaata cactccttaa ttgaagaatc      8160
gcaaaaccag caagaaaaga atgaacaaga attattggaa ttagataaat gggcaagttt      8220
gtggaattgg tttaacataa caaattggct gtggtatata aaattattca taatgatagt      8280
aggaggcttg gtaggtttaa gaatagtttt tgctgtactt tctatagtga atagagttag      8340
gcagggatat tcaccattat cgtttcagac ccacctccca atcccgaggg gacccgacag      8400
gcccgaagga atagaagaag aaggtggaga gagagacaga gacagatcca ttcgattagt      8460
gaacggatcc ttagcactta tctgggacga tctgcggagc ctgtgcctct tcagctacca      8520
ccgcttgaga gacttactct tgattgtaac gaggattgtg gaacttctgg gacgcagggg      8580
gtgggaagcc ctcaaatatt ggtggaatct cctacagtat tggagtcagg aactaaagaa      8640
tagtgctgtt aacttgctca atgccacagc catagcagta gctgagggga cagatagggt      8700
tatagaagta ttacaagcag cttatagagc tattcgccac atacctagaa gaataagaca      8760
gggcttggaa aggattttgc tataagatgg gtggcaagtg gtcaaaaagt agtgtgattg      8820
gatggcctgc tgtaagggaa agaatgagac gagctgagcc agcagcagat ggggtgggag      8880
cagtatctcg agacctagaa aaacatggag caatcacaag tagcaataca gcagctaaca      8940
atgctgcttg tgcctggcta gaagcacaag gaggaggaag ggtgggtttt ccagtcacac      9000
ctcaggtacc tttaagacca atgacttaca aggcagctgt agatcttagc cacttttaa       9060 aagaaagggg gggactggaa gggctaattc actcccaaag aagacaagat atccttgatc      9120
tgtggatcta ccacacacaa ggctacttcc ctgattggca gaactacaca ccagggccag      9180
gggtcagata tccactgacc tttggatggt gctacaagct agtaccagtt gagccagata      9240
aggtagaaga ggccaataaa ggagagaaca ccagcttgtt acaccctgtg agcctgcatg      9300
gaatggatga ccctgagaga gaagtgttag agtggaggtt tgacagccgc ctagcatttc      9360
atcacgtggc ccgagagctg catccggagt acttcaagaa ctgctgacat cgagcttgct      9420
```

```
acaagggact tccgctggg gactttccag ggaggcgtgg cctgggcggg actgggagt    9480
ggcgagccct cagatgctgc atataagcag ctgcttttgg cctgtactgg gtctctctgg  9540
ttagaccaga tctgagcctg ggagctctct ggctaactag ggaacccact gcttaagcct  9600
caataaagct tgccttgagt gcttcaagta gtgtgtgccc gtctgttgtg tgactctggt  9660
aactagagat ccctcagacc cttttagtca gtgtggaaaa tctctagcac ccaggaggta  9720
gaggttgcag tgagccaaga tcgcgccact gcattccagc ctgggcaaga aaacaagact  9780
gtctaaaata ataataataa gttaagggta ttaaatatat ttatacatgg aggtcataaa  9840
aatatatata tttgggctgg gcgcagtggc tcacacctgc gcccggccct ttgggaggcc  9900
gaggcaggtg gatcacctga gtttgggagt ccagaccag cctgaccaac atggagaaac    9960
cccttctctg tgtattttta gtagattta ttttatgtgt attttattca caggtatttc    10020
tggaaaactg aaactgtttt tcctctactc tgataccaca agaatcatca gcacagagga  10080
agacttctgt gatcaaatgt ggtgggagag ggaggttttc accagcacat gagcagtcag  10140
ttctgccgca gactcggcgg gtgtccttcg gttcagttcc aacaccgcct gcctggagag  10200
aggtcagacc acagggtgag ggctcagtcc ccaagacata aacacccaag acataaacac  10260
ccaacaggtc caccccgcct gctgcccagg cagagccgat tcaccaagac gggaattagg  10320
atagagaaag agtaagtcac acagagccgg ctgtgcggga aacggagtt ctattatgac    10380
tcaaatcagt ctccccaagc attcggggat cagagttttt aaggataact tagtgtgtag  10440
ggggccagtg agttggagat gaaagcgtag ggagtcgaag gtgtccttt gcgccgagtc    10500
agttcctggg tgggggccac aagatcggat gagccagttt atcaatccgg gggtgccagc  10560
tgatccatgg agtgcaggt ctgcaaaata tctcaagcac tgattgatct taggttttac    10620
aatagtgatg ttaccccagg aacaatttgg ggaaggtcag aatcttgtag cctgtagctg  10680
catgactcct aaaccataat ttcttttttg tttttttttt tttattttg agacagggtc    10740
tcactctgtc acctaggctg gagtgcagtg gtgcaatcac agctcactgc agcctcaacg  10800
tcgtaagctc aagcgatcct cccacctcag cctgcctggt agctgagact acaagcgacg  10860
ccccagttaa ttttgtatt tttggtagag gcagcgtttt gccgtgtggc cctggctggt    10920
ctcgaactcc tgggctcaag tgatccagcc tcagcctccc aaagtgctgg acaaccggg    10980
gccagtcact gcacctggcc ctaaaccata atttctaatc ttttggctaa tttgttagtc  11040
ctacaaaggc agtctagtcc ccaggcaaaa aggggtttg tttcgggaaa gggctgttac    11100
tgtctttgtt tcaaactata aactaagttc ctcctaaact tagttcggcc tacacccagg  11160
aatgaacaag gagagcttgg aggttagaag cacgatggaa ttggttaggt cagatctctt  11220
tcactgtctg agttataatt ttgcaatggt ggttcaaaga ctgcccgctt ctgacaccag  11280
tcgctgcatt aatgaatcgg ccaacgcgcg gggagaggcg gtttgcgtat gggcgctct    11340
tccgcttcct cgctcactga ctcgctgcgc tcggtcgttc ggctgcggcg agcggtatca  11400
gctcactcaa aggcggtaat acggttatcc acagaatcag gggataacgc aggaaagaac  11460
atgtgagcaa aaggccagca aaaggccagg aaccgtaaaa aggccgcgtt gctggcgttt  11520
ttccataggc tccgccccc tgacgagcat cacaaaaatc gacgctcaag tcagaggtgg    11580
cgaaacccga caggactata aagataccag gcgtttcccc ctggaagctc cctcgtgcgc  11640
tctcctgttc cgaccctgcc gcttaccgga tacctgtccg cctttctccc ttcgggaagc  11700
gtggcgcttt ctcatagctc acgctgtagg tatctcagtt cggtgtaggt cgttcgctcc  11760
```

```
aagctgggct gtgtgcacga acccccgtt cagcccgacc gctgcgcctt atccggtaac    11820
tatcgtcttg agtccaaccc ggtaagacac gacttatcgc cactggcagc agccactggt    11880
aacaggatta gcagagcgag gtatgtaggc ggtgctacag agttcttgaa gtggtggcct    11940
aactacggct acactagaag aacagtattt ggtatctgcg ctctgctgaa gccagttacc    12000
ttcggaaaaa gagttggtag ctcttgatcc ggcaaacaaa ccaccgctgg tagcggtggt    12060
ttttttgttt gcaagcagca gattacgcgc agaaaaaaag gatctcaaga agatcctttg    12120
atcttttcta cggggtctga cgctcagtgg aacgaaaact cacgttaagg gattttggtc    12180
atgagattat caaaaaggat cttcacctag atccttttaa attaaaaatg aagttttaaa    12240
tcaatctaaa gtatatatga gtaaacttgg tctgacagtt accaatgctt aatcagtgag    12300
gcacctatct cagcgatctg tctatttcgt tcatccatag ttgcctgact ccccgtcgtg    12360
tagataacta cgatacggga gggcttacca tctggcccca gtgctgcaat gataccgcga    12420
gacccacgct caccggctcc agatttatca gcaataaacc agccagccgg aagggccgag    12480
cgcagaagtg gtcctgcaac tttatccgcc tccatccagt ctattaattg ttgccgggaa    12540
gctagagtaa gtagttcgcc agttaatagt ttgcgcaacg ttgttgccat tgctacaggc    12600
atcgtggtgt cacgctcgtc gtttggtatg gcttcattca gctccggttc caacgatca    12660 aggcgagtta catgatcccc catgttgtgc aaaaaagcgg ttagctcctt cggtcctccg    12720
atcgttgtca gaagtaagtt ggccgcagtg ttatcactca tggttatggc agcactgcat    12780
aattctctta ctgtcatgcc atccgtaaga tgcttttctg tgactggtga gtactcaacc    12840
aagtcattct gagaatagtg tatgcggcga ccgagttgct cttgcccggc gtcaatacgg    12900
gataataccg cgccacatag cagaacttta aaagtgctca tcattggaaa acgttcttcg    12960
gggcgaaaac tctcaaggat cttaccgctg ttgagatcca gttcgatgta acccactcgt    13020
gcacccaact gatcttcagc atcttttact ttcaccagcg tttctgggtg agcaaaaaca    13080
ggaaggcaaa atgccgcaaa aaagggaata agggcgacac ggaaatgttg aatactcata    13140
ctcttccttt ttcaatatta ttgaagcatt tatcagggtt attgtctcat gagcggatac    13200
atatttgaat gtatttagaa aaataaacaa ataggggttc cgcgcacatt tccccgaaaa    13260
gtgccacctg acgtctaaga aaccattatt atcatgacat taacctataa aaataggcgt    13320
atcacgaggc cctttcgtct cgcgcgtttc ggtgatgacg gtgaaaacct ctgacacatg    13380
cagctcccgg agacggtcac agcttgtctg taagcggatg ccgggagcag acaagcccgt    13440
cagggcgcgt cagcgggtgt tggcgggtgt cggggctggc ttaactatgc ggcatcagag    13500
cagattgtac tgagagtgca ccatatgcgg tgtgaaatac cgcacagatg cgtaaggaga    13560
aaataccgca tcaggcgcca ttcgccattc aggctgcgca actgttggga agggcgatcg    13620
gtgcgggcct cttcgctatt acgccagggg aggcagagat tgcagtaagc tgagatcgca    13680
gcactgcact ccagcctggg cgacagagta agactctgtc tcaaaaataa aataaataaa    13740
tcaatcagat attccaatct tttcctttat ttatttattt attttctatt ttggaaacac    13800
agtccttcct tattccagaa ttacacatat attctatttt tctttatatg ctccagtttt    13860
ttttagacct tcacctgaaa tgtgtgtata caaaatctag gccagtccag cagagcctaa    13920
aggtaaaaaa taaaataata aaaataaat aaaatctagc tcactccttc acatcaaaat    13980
ggagatacag ctgttagcat taaataccaa ataaccatc ttgtcctcaa taattttaag    14040
cgcctctctc caccacatct aactcctgtc aaaggcatgt gccccttccg ggcgctctgc    14100
tgtgctgcca accaactggc atgtggactc tgcagggtcc ctaactgcca agccccacag    14160
```

```
tgtgccctga ggctgcccct tccttctagc ggctgccccc actcggcttt gctttcccta   14220
gtttcagtta cttgcgttca gccaaggtct gaaactaggt gcgcacagag cggtaagact   14280
gcgagagaaa gagaccagct ttacagggg tttatcacag tgcaccctga cagtcgtcag    14340
cctcacaggg ggттттaтcac attgcaccct gacagtcgtc agcctcacag gggtttatc   14400 acagtgcacc cttacaatca ttccatttga ttcacaattt ttttagtctc tactgtgcct   14460
aacttgtaag ttaaatttga tcagaggtgt gttcccagag gggaaaacag tatatacagg   14520
gttcagtact atcgcatttc aggcctccac ctgggtcttg gaatgtgtcc cccgaggggt   14580
gatgactacc tcagttggat ctccacaggt cacagtgaca caagataacc aagacacctc   14640
ccaaggctac cacaatgggc cgccctccac gtgcacatgg ccggaggaac tgccatgtcg   14700
gaggtgcaag cacacctgcg caтcagaгтc cttggtgtgg agggagggac cagcgcagct   14760

tccagccatc cacctgatga acagaaccta gggaaagccc cagttctact tacaccagga   14820
aaggc                                                                14825
```

<210> SEQ ID NO 385
<211> LENGTH: 10535
<212> TYPE: DNA
<213> ORGANISM: Simian immunodeficiency virus

<400> SEQUENCE: 385

```
gcatgcacat tttaaaggct tttgctaaat atagccaaaa gtccttctac aaattttcta     60
agagttctga tcaaaagcag taacaggcct tgtctcatca tgaactttgg catttcatct    120
acagctaagt ttatatcata aatagttctt tacaggcagc accaacttat acccttatag    180
catactttac tgtgtgaaaa ttgcatcttt cattaagctt actgtaaatt tactggctgt    240
cttccttgca ggtttctgga aggatttat tacagtgcaa gaagacatag aatcttagac    300
atatacttag aaaaggaaga aggcatcata ccagattggc aggattacac ctcaggacca    360
ggaattagat acccaaagac atttggctgg ctatggaaat tagtccctgt aaatgtatca    420
gatgaggcac aggaggatga ggagcattat ttaatgcatc cagctcaaac ttcccagtgg    480
gatgaccctt ggggagaggt tctagcatgg aagtttgatc caactctggc ctacacttat    540
gaggcatatg ttagataccc agaagagttt ggaagcaagt caggcctgtc agaggaagag    600
gttagaagaa ggctaaccgc aagaggcctt cttaacatgg ctgacaagaa ggaaactcgc    660

tgaaacagca gggactttcc acaaggggat gttacgggga ggtactgggg aggagccggt    720
cgggaacgcc cactttcttg atgtataaat atcactgcat ttcgctctgt attcagtcgc    780

tctgcggaga ggctggcaga ttgagccctg ggaggttctc tccagcacta gcaggtagag    840
cctgggtgtt ccctgctaga ctctcaccag cacttggccg gtgctgggca gagtgactcc    900
acgcttgctt gcttaaagcc ctcttcaata aagctgccat tttagaagta agctagtgtg    960

tgttcccatc tctcctagcc gccgcctggt caactcggta tcaataata agaagaccct   1020 ggtctgttag gaccctttct gctttgggaa accgaagcag gaaaatccct agcagattgg   1080
cgcctgaaca gggacttgaa ggagagtgag agactcctga gtacggctga gtgaaggcag   1140

taagggcggc aggaaccaac cacgacggag tgctcctata aggcgcgggt cggtaccag    1200 acggcgtgag gagcgggaga ggaagaggcc tccggttgca ggtaagtgca acacaaaaaa   1260
gaaatagctg tcttttatcc aggaaggggt aataagatag aгтgggagaт gggcgtgaga   1320 aactccgtct tgtcagggaa gaaagcagat gaattagaaa aaattaggct acgacccaac   1380
```

-continued

```
ggaaagaaaa agtacatgtt gaagcatgta gtatgggcag caaatgaatt agatagattt    1440
ggattagcag aaagcctgtt ggagaacaaa gaaggatgtc aaaaaatact ttcggtctta    1500
gctccattag tgccaacagg ctcagaaaat ttaaaaagcc tttataatac tgtctgcgtc    1560
atctggtgca ttcacgcaga agagaaagtg aaacacactg aggaagcaaa acagatagtg    1620
cagagacacc tagtggtgga acaggaaca acagaaacta tgccaaaaac aagtagacca    1680
acagcaccat ctagcggcag aggaggaaat tacccagtac aacaaatagg tggtaactat    1740
gtccacctgc cattaagccc gagaacatta aatgcctggg taaaattgat agaggaaaag    1800
aaatttggag cagaagtagt gccaggattt caggcactgt cagaaggttg cacccccat    1860 gacattaatc agatgttaaa ttgtgtggga gaccatcaag cggctatgca gattatcaga    1920
gatattataa acgaggaggc tgcagattgg gacttgcagc acccacaacc agctccacaa    1980
caaggacaac ttagggagcc gtcaggatca gatattgcag gaacaactag ttcagtagat    2040
gaacaaatcc agtggatgta cagacaacag aaccccatac cagtaggcaa catttacagg    2100
agatggatcc aactgggtt gcaaaaatgt gtcagaatgt ataacccaac aaacattcta    2160
gatgtaaaac aagggccaaa agagccattt cagagctatg tagacaggtt ctacaaaagt    2220
ttaagagcag aacagacaga tgcagcagta aagaattgga tgactcaaac actgctgatt    2280
caaaatgcta acccagattg caagctagtg ctgaaggggc tgggtgtgaa tcccacccta    2340
gaagaaatgc tgacggcttg tcaaggagta gggggggccgg gacagaaggc tagattaatg    2400
gcagaagccc tgaaagaggc cctcgcacca gtgccaatcc cttttgcagc agcccaacag    2460
aggggaccaa gaaagccaat taagtgtggg aattgtggga agagggacca ctctgcaagg    2520
caatgcagag ccccaagaag acagggatgc tggaaatgtg gaaaaatgga ccatgttatg    2580
gccaaatgcc cagacagaca ggcgggtttt ttaggccttg gtccatgggg aaagaagccc    2640
cgcaatttcc ccatggctca agtgcatcag gggctgatgc caactgctcc cccagaggac    2700
ccagctgtgg atctgctaaa gaactacatg cagttgggca agcagcagag agaaaagcag    2760
agagaaagca gagagaagcc ttacaaggag gtgacagagg atttgctgca cctcaattct    2820
ctctttggag gagaccagta gtcactgctc atattgaagg acagcctgta gaagtattac    2880
tggatacagg ggctgatgat tctattgtaa caggaataga gttaggtcca cattataccc    2940
caaaaatagt aggaggaata ggaggtttta ttaatactaa agaatacaaa aatgtagaaa    3000
tagaagtttt aggcaaaagg attaaaggga caatcatgac aggggacacc ccgattaaca    3060
tttttggtag aaatttgcta acagctctgg ggatgtctct aaattttccc atagctaaag    3120
tagagcctgt aaaagtcgcc ttaaagccag gaaaggatgg accaaaattg aagcagtggc    3180
cattatcaaa agaaaagata gttgcattaa gagaaatctg tgaaaagatg gaaaaggatg    3240
gtcagttgga ggaagctccc ccgaccaatc catacaacac ccccacattt gctataaaga    3300
aaaaggataa gaacaaatgg agaatgctga tagattttag gaactaaat agggtcactc    3360 aggactttac ggaagtccaa ttaggaatac cacacctgc aggactagca aaaggaaaa    3420 gaattacagt actggatata ggtgatgcat atttctccat acctctagat gaagaattta    3480
ggcagtacac tgcctttact ttaccatcag taaataatgc agagccagga aaacgataca    3540
tttataaggt tctgcctcag ggatggaagg ggtcaccagc catcttccaa tacactatga    3600
gacatgtgct agaacccttc aggaaggcaa atcagatgt gaccttagtc cagtatatgg    3660
atgacatctt aatagctagt gacaggacag acctggaaca tgcagggta gttttacagt    3720 caaaggaact cttgaatagc atagggtttt ctaccccaga agagaaattc caaaaagatc    3780
```

-continued

| | | | | |
|---|---|---|---|---|
| ccccatttca | atggatgggg | tacgaattgt | ggccaacaaa | atggaagttg caaaagatag | 3840 |
| agttgccaca | aagagagacc | tggacagtga | atgatataca | gaagttagta ggagtattaa | 3900 |
| attgggcagc | tcaaatttat | ccaggtataa | aaccaaaca | tctctgtagg ttaattagag | 3960 |
| gaaaaatgac | tctaacagag | gaagttcagt | ggactgagat | ggcagaagca gaatatgagg | 4020 |
| aaaataaaat | aattctcagt | caggaacaag | aaggatgtta | ttaccaagaa ggcaagccat | 4080 |
| tagaagccac | ggtaataaag | agtcaggaca | atcagtggtc | ttataaaatt caccaagaag | 4140 |
| acaaaatact | gaaagtagga | aaatttgcaa | agataaagaa | tacacatacc aatggagtga | 4200 |
| gactattagc | acatgtaata | cagaaaatag | gaaaggaagc | aatagtgatc tggggacagg | 4260 |
| tcccaaaatt | ccacttacca | gttgagaagg | atgtatggga | acagtggtgg acagactatt | 4320 |
| ggcaggtaac | ctggataccg | gaatgggatt | ttatctcaac | accaccgcta gtaagattag | 4380 |
| tcttcaatct | agtgaaggac | cctatagagg | gagaagaaac | ctattataca gatggatcat | 4440 |
| gtaataaaca | gtcaaaagaa | gggaaagcag | gatatatcac | agatagggc aaagacaaag | 4500 |
| taaaagtgtt | agaacagact | actaatcaac | aagcagaatt | ggaagcattt ctcatggcat | 4560 |
| tgacagactc | agggccaaag | gcaaatatta | tagtagattc | acaatatgtt atgggaataa | 4620 |
| taacaggatg | ccctacagaa | tcagagagca | ggctagttaa | tcaaataata gaagaaatga | 4680 |
| ttaaaaagtc | agaaatttat | gtagcatggg | taccagcaca | caaaggtata ggaggaaacc | 4740 |
| aagaaataga | ccacctagtt | agtcaaggga | ttagacaagt | tctcttcttg gaaaagatag | 4800 |
| agccagcaca | agaagaacat | gataaatacc | atagtaatgt | aaaagaattg gtattcaaat | 4860 |
| ttggattacc | cagaatagtg | gccagacaga | tagtagacac | ctgtgataaa tgtcatcaga | 4920 |
| aaggagaggc | tatacatggg | caggcaaatt | cagatctagg | gacttggcaa atggattgta | 4980 |
| cccatctaga | gggaaaaata | atcatagttg | cagtacatgt | agctagtgga ttcatagaag | 5040 |
| cagaggtaat | tccacaagag | acaggaagac | agacagcact | atttctgtta aaattggcag | 5100 |
| gcagatggcc | tattacacat | ctacacacag | ataatggtgc | taactttgct tcgcaagaag | 5160 |
| taaagatggt | tgcatggtgg | gcagggatag | agcacacctt | tggggtacca tacaatccac | 5220 |
| agagtcaggg | agtagtggaa | gcaatgaatc | accacctgaa | aaatcaaata gatagaatca | 5280 |
| gggaacaagc | aaattcagta | gaaaccatag | tattaatggc | agttcattgc atgaatttta | 5340 |
| aaagaagggg | aggaataggg | gatatgactc | cagcagaaaa | attaattaac atgatcacta | 5400 |
| cagaacaaga | gatacaattt | caacaatcaa | aaaactcaaa | attttaaaaat tttcgggtct | 5460 |
| attacagaga | aggcagagat | caactgtgga | agggacccgg | tgagctattg tggaaagggg | 5520 |
| aaggagcagt | catcttaaag | gtagggacag | acattaaggt | agtacccaga agaaaggcta | 5580 |
| aaattatcaa | agattatgga | ggaggaaaag | aggtggatag | cagttcccac atggaggata | 5640 |
| ccggagaggc | tagagaggtg | gcatagcctc | ataaatatc | tgaaatataa aactaaagat | 5700 |
| ctacaaaagg | tttgctatgt | gccccatttt | aaggtcggat | gggcatggtg gacctgcagc | 5760 |
| agagtaatct | tcccactaca | ggaaggaagc | catttagaag | tacaagggta ttggcatttg | 5820 |
| acaccagaaa | aagggtggct | cagtacttat | gcagtgagga | taacctggta ctcaaagaac | 5880 |
| ttttggacag | atgtaacacc | aaactatgca | gacattttac | tgcatagcac ttatttccct | 5940 |
| tgctttacag | cgggagaagt | gagaagggcc | atcaggggag | aacaactgct gtcttgctgc | 6000 |
| aggttcccga | gagctcataa | gtaccaggta | ccaagcctac | agtacttagc actgaaagta | 6060 |
| gtaagcgatg | tcagatccca | gggagagaat | cccacctgga | aacagtggag aagagacaat | 6120 |

```
aggagaggcc ttcgaatggc taaacagaac agtagaggag ataaacagag aggcggtaaa    6180
ccacctacca agggagctaa ttttccaggt ttggcaaagg tcttgggaat actggcatga    6240
tgaacaaggg atgtcaccaa gctatgtaaa atacagatac ttgtgtttaa tacaaaaggc    6300
tttatttatg cattgcaaga aaggctgtag atgtctaggg gaaggacatg gggcaggggg    6360
atggagacca ggacctcctc ctcctccccc tccaggacta gcataaatgg aagaaagacc    6420
tccagaaaat gaaggaccac aaagggaacc atgggatgaa tgggtagtgg aggttctgga    6480
agaactgaaa gaagaagctt taaaacattt tgatcctcgc ttgctaactg cacttggtaa    6540
tcatatctat aatagacatg gagacaccct tgagggagca ggagaactca ttagaatcct    6600
ccaacgagcg ctcttcatgc atttcagagg cggatgcatc cactccagaa tcggccaacc    6660
tgggggagga atcctctct cagctatacc gccctctaga agcatgctat aacacatgct     6720
attgtaaaaa gtgttgctac cattgccagt tttgtttcct taaaaaaggc ttggggatat    6780
gttatgagca atcacgaaag agaagaagaa ctccgaaaaa ggctaaggct aatacatctt    6840
ctgcatcaaa caagtaagta tgggatgtct tgggaatcag ctgcttatcg ccatcttgct    6900
tttaagtgtc tatgggatct attgtactct atatgtcaca gtcttttatg gtgtaccagc    6960
ttggaggaat gcgacaattc ccctcttttg tgcaaccaag aatagggata cttggggaac    7020
aactcagtgc ctaccagata atggtgatta ttcagaagtg gccccttaatg ttacagaaag    7080 ctttgatgcc tggaataata cagtcacaga acaggcaata gaggatgtat ggcaactctt    7140
tgagacctca ataaagcctt gtgtaaaatt atccccatta tgcattacta tgagatgcaa    7200
taaaagtgag acagatagat ggggattgac aaaatcaata caacaacag catcaacaac    7260 atcaacgaca gcatcagcaa aagtagacat ggtcaatgag actagttctt gtatagccca    7320
ggataattgc acaggcttgg aacaagagca aatgataagc tgtaaattca acatgacagg    7380
gttaaaaaga gacaagaaaa agagtacaa tgaaacttgg tactctgcag atttggtatg    7440
tgaacaaggg aataacactg gtaatgaaag tagatgttac atgaaccact gtaacacttc    7500
tgttatccaa gagtcttgtg acaaacatta ttgggatgct attagattta ggtattgtgc    7560
acctccaggt tatgctttgc ttagatgtaa tgacacaaat tattcaggct ttatgcctaa    7620
atgttctaag gtggtggtct cttcatgcac aaggatgatg gagacacaga cttctacttg    7680
gtttggcttt aatggaacta gagcagaaaa tagaacttat atttactggc atggtaggga    7740
taataggact ataattagtt taaataagta ttataatcta acaatgaaat gtagaagacc    7800
aggaaataag acagttttac cagtcaccat tatgtctgga ttggttttcc actcacaacc    7860
aatcaatgat aggccaaagc aggcatggtg ttggtttgga ggaaaatgga aggatgcaat    7920
aaaagaggtg aagcagacca ttgtcaaaca tcccaggtat actggaacta acaatactga    7980
taaaatcaat ttgacggctc ctggaggagg agatccggaa gttaccttca tgtggacaaa    8040
ttgcagagga gagttcctct actgtaaaat gaattggttt ctaaattggg tagaagatag    8100
gaatacagct aaccagaagc caaaggaaca gcataaaagg aattacgtgc catgtcatat    8160
tagacaaata atcaacactt ggcataaagt aggcaaaaat gtttatttgc ctccaagaga    8220
gggagacctc acgtgtaact ccacagtgac cagtctcata gcaaacatag attggattga    8280
tggaaaccaa actaatatca ccatgagtgc agaggtggca gaactgtatc gattggaatt    8340
gggagattat aaattagtag agatcactcc aattggcttg gccccacag atgtgaagag    8400 gtacactact ggtggcacct caagaaataa aagaggggtc tttgtgctag ggttcttggg    8460
ttttctcgca acggcaggtt ctgcaatggg cgcggcgtcg ttgacgctga ccgctcagtc    8520
```

```
ccgaacttta ttggctggga tagtgcagca acagcaacag ctgttggacg tggtcaagag    8580
acaacaagaa ttgttgcgac tgaccgtctg gggaacaaag aacctccaga ctagggtcac    8640
tgccatcgag aagtacttaa aggaccaggc gcagctgaat gcttggggat gtgcgtttag    8700
acaagtctgc cacactactg taccatggcc aaatgcaagt ctaacaccaa agtggaacaa    8760
tgagacttgg caagagtggg agcgaaaggt tgacttcttg aagaaaata taacagccct    8820 cctagaggag gcacaaattc aacaagagaa gaacatgtat gaattacaaa agttgaatag    8880
ctgggatgtg tttggcaatt ggtttgacct tgcttcttgg ataaagtata tacaatatgg    8940
agtttatata gttgtaggag taatactgtt aagaatagtg atctatatag tacaaatgct    9000
agctaagtta aggcaggggt ataggccagt gttctcttcc ccaccctctt atttccagca    9060
gacccatatc caacaggacc cggcactgcc aaccagagaa ggcaaagaaa gagacggtgg    9120
agaaggcggt ggcaacagct cctggccttg gcagatagaa tatattcatt tcctgatccg    9180
ccaactgata cgcctcttga cttggctatt cagcaactgc agaaccttgc tatcgagagt    9240
ataccagatc ctccaaccaa tactccagag gctctctgcg accctacaga ggattcgaga    9300
agtcctcagg actgaactga cctacctaca atatgggtgg agctatttcc atgaggcggt    9360
ccaggccgtc tggagatctg cgacagagac tcttgcgggc gcgtggggag acttatggga    9420
gactcttagg agaggtggaa gatggatact cgcaatcccc aggaggatta acaagggct    9480 tgagctcact ctcttgtgag ggacagaaat acaatcaggg acagtatatg aatactccat    9540
ggagaaaccc agctgaagag agagaaaaat tagcatacag aaaacaaaat atggatgata    9600
tagatgagta agatgatgac ttggtagggg tatcagtgag gccaaaagtt ccctaagaa    9660 caatgagtta caaattggca atagacatgt ctcattttat aaaagaaaag gggggactgg    9720
aagggattta ttacagtgca agaagacata gaatcttaga catatactta gaaaaggaag    9780
aaggcatcat accagattgg caggattaca cctcaggacc aggaattaga tacccaaaga    9840
catttggctg gctatggaaa ttagtccctg taaatgtatc agatgaggca caggaggatg    9900
aggagcatta tttaatgcat ccagctcaaa cttcccagtg gatgaccct tggggagagg    9960 ttctagcatg gaagtttgat ccaactctgg cctacactta tgaggcatat gttagatacc   10020
cagaagagtt tggaagcaag tcaggcctgt cagaggaaga ggttagaaga aggctaaccg   10080
caagaggcct tcttaacatg gctgacaaga aggaaactcg ctgaaacagc agggactttc   10140
cacaagggga tgttacgggg aggtactggg gaggagccgg tcgggaacgc ccactttctt   10200
gatgtataaa tatcactgca tttcgctctg tattcagtcg ctctgcggag aggctggcag   10260
attgagccct gggaggttct ctccagcact agcaggtaga gcctgggtgt tccctgctag   10320
actctcacca gcacttggcc ggtgctgggc agagtgactc cacgcttgct tgcttaaagc   10380
cctcttcaat aaagctgcca ttttagaagt aagctagtgt gtgttcccat ctctcctagc   10440
cgccgcctgg tcaactcggt actcaataat aagaagaccc tggtctgtta ggaccctttc   10500
tgctttggga aaccgaagca ggaaaatccc tagca                              10535
```

<210> SEQ ID NO 386
<211> LENGTH: 9713
<212> TYPE: DNA
<213> ORGANISM: Human immunodeficiency virus 2

<400> SEQUENCE: 386

```
agtcgctctg cggagaggct ggcagattga gccctgggag gttctctcca gcactagcag      60
```

```
gtagagcctg ggtgttccct gctagactct caccggtgct tggccggcac tgggcagacg      120
gctccacgct tgcttgctta aaagacctct taataaagct gccagttaga agcaagttaa      180
gtgtgtgttc ccatctctcc tagtcgccgc ctggtcattc ggtgttcatc tgaataacaa      240
gaccctggtc tgttaggacc ctttctgctt tgggaaacca aagcaggaaa atccctagca      300
ggttggcgcc cgaacaggga cttagagaag actgaaaagc cttggaacac ggctgagtga      360
aggcagtaag ggcggcagga acaaaccacg acggagtgct cctagaaagg cgcaggccaa      420
ggtaccaaag gcggcgtgtg gagcgggagt aaagaggcct ccgggtgaag gtaagtacct      480
acaccaaaaa attgtagcca ggaagggctt gttatcctac ctttagacag gtagaagatt      540
gtgggagatg ggcgcgagaa actccgtctt gaaagggaaa aaagcagacg aattagaaac      600
aattaggtta cggcccggcg gaaagaaaaa atacaggcta agcatattg tgtgggcagc       660 gaatgaattg gacagattcg gattagcaga gagcctgttg gagtcaaaag aaggttgcca      720
aagaattctt acagttttag gtccattagt accgacaggt tcagaaaatt taaaaagcct      780
ttttaatact gtctgcgtca tttggtgcat acacgcagaa gagaaagtga agatactga      840 aggagcaaaa caaatagtac agagacatct agcggcagaa acaggaactg cagagaaaat      900
gccaaataca agtagaccaa cagcaccacc tagcgggaag ggaggaaact tccccgtaca      960
acaagtaggc ggcaattata cccatgtgcc gctgagtcct cgaaccctaa atgcttgggt     1020
aaaattagta gaggaaaaga agttcgggc agaggtagtg ccaggatttc aggcactctc      1080
agaaggctgc acgccctatg atatcaacca aatgcttaat tgtgtgggcg accatcaagc     1140
agctatgcaa ataatcaggg agatcgttaa tgaagaagca gcagattggg atgtgcaaca     1200
tccaatacca ggtcccttac cagcggggca gcttagagaa ccaagagggt ctgacatagc     1260
agggacaaca agcacagtag atgaacagat ccagtggatg tttaggccac aaaatcccgt     1320
accagtggga aacatctata ggagatggat ccagatagga ctgcagaagt gcgtcaggat     1380
gtacaacccg accaacatcc tagacataaa acaaggacca aaggaaccat tccaaagtta     1440
tgtagataga ttctacaaaa gcttgagggc agaacaaaca gatccagcag tgaagaattg     1500
gatgacccag acactactag tacagaatgc caacccagac tgtaaattag tactaaaagg     1560
actagggatg aatcctacct tagaagagat gctaaccgcc tgccaagggg taggtgggcc     1620
aggccagaaa gctagactaa tggcagaagc cttaaaagag gccttgacac cagcccctat     1680
cccatttgca gcagcccagc agaaaaggac aattaaatgc tggaattgtg gaaaggaagg     1740
acactcggca gacaatgcc gagcacctag aagacagggc tgctggaagt gtggtaaacc      1800
aggacatgtc atagcaaatt gcccagatag acaggtgggt ttttaggga tgggccccg       1860 gggaaagaag ccccgcaact tccccgtggc ccaagtcccg caggggctaa caccaacagc     1920 accccccagta gatccagcag tggacctact ggagaattat atgcagcaag aaaaagaca     1980 aagaaacag agagagagac catacaaaga agtgacagag gacttactgc acctcgagca      2040
gggagaggca ccatgcagag agacgacaga ggacttgctg cacctcaatt ctctctttg     2100 aaaagaccag tagtcacggc atacgtcgag ggccagccag tagaagttct gctagacacg     2160
ggggctgacg actcaatagt agcagggata gagttaggga gcaattatag tccaaagata     2220
gtaggaggaa taggggatt cataaatacc aaggaatata aaaatgtaaa aatagaagtt      2280
ttaggtaaaa aggtaagggc caccataatg acaggtgaca ccccaatcaa cattttggc     2340 agaaatattc tgacagcctt aggcatgtca ttaaatttac cagtcgccaa aatagaacca     2400
ataaaaataa tgttaaagcc aggaaaagat ggaccaaaac tgaggcaatg gcccttaaca     2460
```

```
aaagaaaaaa tagaggcact aaaagaaatc tgtgaaaaaa tggaaagaga aggccagcta    2520
gaggaagcgc ctccaactaa tccttataac acccccacat ttgcaatcaa gaaaaaggac    2580
aaaaataaat ggaggatgct aatagatttt agagaactaa acaaggtaac tcaagatttc    2640
acagaaattc agttaggaat tccacaccca gcaggattgg ccaagaaaaa agaattact    2700 gtactagata tagggatgc ttacttttcc ataccactac atgaagactt tagacagtat     2760
actgcattta ctttaccatc aataaacaat gcagaaccag aaaaagata tatatataag     2820 gtcctgcctc agggatggaa ggggtcacca gcaatttttc aatacacaat gaggcaggtc    2880
ttagaaccat tcagaaaagc aaacctagat gtcattatca ttcagtacat ggatgatatc    2940
ctaatagcta gtgacaggac agatctagaa catgacaagg tggtcctgca gctaaaggaa    3000
cttctaaata acctaggatt ttctacccca gatgagaagt tccaaaagga ccctccatac    3060
cactggatgg gctatgaact gtggccaact aagtggaagc tgcagaagat acagttgccc    3120
caaaaagatg tatggacagt aaatgacatc caaaagttag tgggtgtctt aaactgggca    3180
gcacaaatct acccagggat aaaaaccaga cacttatgta agctaattag aggaaaaatg    3240
acactcacag aagaagtaca gtggacagaa ctagcagagg cggagttaga agagaacaag    3300
attatcttaa gccaggagca agagggacac tattaccaag aagaaaaaga gttagaagca    3360
acagtccaaa aggatcaaga caatcagtgg acatataaag tacaccaggg agagaaaatt    3420
ctaaaagtag ggaaatatgc aaagataaaa atacccata ccaatggggt cagattgtta     3480
gcacaagtag ttcaaaagat aggaaaagaa gcactaatca tttggggacg aataccaaaa    3540
tttcacctac cagtagaaag agagacatgg gaacagtggt gggatgacta ctggcaggtg    3600
acatggatcc ctgactggga cttcgtatct accccgccgc tggtcagact agcatttaac    3660
ctggtaaaag atcctatacc aagaacagag actttctaca cagatggatc ctgcaatagg    3720
caatcaaagg aaggaaaagc aggatatgta acagatagag ggagagacaa ggtaaggatg    3780
ctagaacaaa ctaccaatca gcaagcagaa ttagaagcct ttgcaatggc actaacagac    3840
tcaggtccaa aagccaatat tatagtagac tcacagtatg taatggggat agtagcaggc    3900
cagccaacag aatcagagag tagaatagta aatcaaatca tagaggagat gataaaaaag    3960
gaagcaatct atgttgcatg ggtcccagcc cataaaggca taggagggaa tcaggagta    4020 gatcagttag taagtcaggg catcagacaa gtgttgttcc tggaaaaat agagcccgct     4080 caggaagaac atgagaaata ccatagcaat gtaaaagaac tatcccataa atttggattg    4140
cccaaattag tagcaagaca aatagtaaac acatgtgccc aatgtcaaca gaaggggag     4200 gctatacatg gcaagtaga tgcagaatta ggcacttggc aaatggactg cacacactta    4260
gaaggaaaga tcattatagt agcagtacat gttgcaagtg gattcataga agcagaagtc    4320
atcccacagg aatcaggaag gcagacagca ctcttcctat aaaactggc cagtaggtgg     4380 ccaataacac acttgcacac agataatggt gccaacttca cttcacagga agtaaaaatg    4440
gtagcatggt gggtaggtat agaacaatct ttcggagtac cttacaatcc acaaagccaa    4500
ggagtagtag aagcaatgaa tcaccaccta aaaaatcaga taagtagaat tagagaacag    4560
gcaaatacag tagaaacaat agtactgatg gcaacacact gcatgaattt taaaagaagg    4620
ggaggaatag gggatatgac cccagcagaa agactaatca atatgatcac cacagaacaa    4680
gaaatacaat tcctccacgc caaaaattca aaattaaaaa attttcgggt ctatttcaga    4740
gaaggcagag atcagctgtg gaaaggaccc ggggaactac tgtggaaggg agacggagca    4800
```

```
gtcatagtca aggtagggac agacataaaa gtagtaccaa ggaggaaagc caagatcatc    4860
aaagactatg gaggaaggca agaactggat agtggttccc acttggaggg tgccagggag    4920
gatggagaaa tggcatagcc ttgtcaaata tctaaaatac agaacaaaag atctagaaga    4980
cgtgtgctat gttccccacc ataaagtagg atgggcatgg tggacttgca gcagggtaat    5040
attcccatta aagggaaaca gtcatctaga aatacaggca tattggaacc taacgccaga    5100
aaaaggatgg ctctcctctt attcagtaag aatgacttgg tatacggaaa ggttctggac    5160
agatgttacc ccagactgtg cagactccct aatacatagc acttatttct cttgctttac    5220
agcaggtgaa gtaagaagag ccatcagagg ggaaaagtta ttgtcctgct gcaattatcc    5280
ccaagcccat agagcccagg taccgtcact ccaattttg gccttagtgg tagtgcagca    5340
aaatgacaga ccccagagaa acggtacccc caggaaacag tggcgaagag actatcgaag    5400
aggccttcaa ttggctagac aggacggtag aagccataaa cagagaggca gtgaatcacc    5460
tgccccgaga gcttattttc caggtgtggc agaggtcctg gagatactgg catgatgaac    5520
aagggatgtc acaaagttac acaaagtata gatatttgtg cttaatacag aaggctatgt    5580
tcacacattg taagagaggg tgcacttgcc tgggggagg acatgggcca ggagggtgga    5640
gaccaggacc tccccctcct cccctccag gtctagtcta atgactgaag caccaacaga    5700 gtttccccg aggatgggga ccccaccgag ggaaccaggg gatgagtgga taatagaaat    5760
cctgagaaaa ataagaaag aagctttaaa gcattttgac cctcgcttgc taactgctct    5820
tggcaactat atccatacta gacatggaga cacccttgaa ggcgccagag agctcattaa    5880
tgtcctacaa cgagccctct tcatgcactt cagagcggga tgtaggctct caagaattgg    5940
ccaaacaggg ggaagaactc cttccccagc tacatcgacc cctagaacca tgcaataaca    6000
aatgctattg taaaggatgc tgcttccact gccagctgtg ttttttaaac aaggggctcg    6060
ggatatgtta tgaccggaag ggcagacgaa gaagaactcc gaagaaaact aaggctcatt    6120
catcttctgc atcagacaag tgagtatgat gggtggtaga aatcagctgc ttgttgccat    6180
tttgctaact agtacttgct tgatatattg caccaattat gtgactgttt tctatggcat    6240
acccgcgtgg agaaatgcat ccattcccct cttttgtgca accaagaata gggatacttg    6300
gggaaccata cagtgcttgc cagacaatga tgattatcag gagataactt tgaatgtgac    6360
agaggctttc gatgcatggg ataatacagt aacagaacaa gcaatagaag atgtctggaa    6420
tctatttgag acatcaataa aaccatgtgt caaattaacg cctttatgtg tagcaatgag    6480
atgtaacaac acagatgcaa ggaacacaac cacacccaca acagcatccc cgcgtacaat    6540
aaaacccgtg acagagataa gtgagaattc ctcatgcata cgcgcaaaca actgctcagg    6600
attgggagaa gaagaggtgg tcaattgtca attcaatatg acaggattag agagagataa    6660
gaaaaagcaa tatagtgaga catggtactc gaaggatgta gtttgtgaag gaaatggcac    6720
cacagataca tgttacatga accattgcaa cacatcggtc atcacagagt catgtgacaa    6780
gcactattgg gatgctatga ggtttagata ctgtgcacca ccaggttttg ccctactaag    6840
atgcaatgat accaattatt caggctttgc gcccaattgc tctaaggtag tagctgctac    6900
atgcaccaga atgatggaaa cgcaaacttc tacatggttt ggctttaatg cactagagc    6960 agaaaataga acatttatct attggcatgg tagggataac agaactatca tcagcttaaa    7020
caaatattat aatctcacta tacattgtaa gaggccagga aataagacag tggtaccaat    7080
aacacttatg tcagggttaa ggtttcactc ccagccggtc atcaataaaa gacccagaca    7140
agcatggtgt tggttcaaag gtgaatggaa gggagccatg caggaggtga aggaaaccct    7200
```

```
tgcaaaacat cccaggtata aaggaaccaa tgaaacaaag aatattaact ttacagcacc   7260
aggaaagggc tcagacccag aggtggcata catgtggact aactgcagag gagaatttct   7320
ctactgcaac atgacttggt tcctcaattg gatagaaaat aagacacacc gcaattatgt   7380
accgtgccat ataagacaaa taattaacac ctggcataag gtagggaaaa atgtatattt   7440
gcctcccagg gaaggggagt tgacctgcaa ctcaacagta actagcataa ttgctaacat   7500
tgatgcaaat ggaaataata caaatattac ctttagtgca gaggtggcag aactataccg   7560
attagagttg ggagattata aattggtaga aataacacca attggcttcg cacctacagc   7620
agaaaaaaga tactcctcta ctccaatgag gaacaagaga ggtgtgttcg tgctagggtt   7680
cttgggtttt ctcgcaacag caggctctgc aatgggcgcg gcgtccttaa cgctgtcggc   7740
tcagtctcgg actttactgg ccgggatagt gcagcaacag caacagctgt tggacgtggt   7800
caagagacaa caggaaatgt tgcgactgac cgtctgggga acaaaaaatc tccaggcaag   7860
agtcactgct atcgagaagt acttaaagga ccaggcgcaa ctaaattcat ggggatgtgc   7920
atttagacaa gtctgccaca ctactgtacc atgggtaaat gatacctta cgcctgagtg    7980 gaacaatatg acgtggcaag aatgggaagg caaaatccgc gacctggagg caaatatcag   8040
tcaacaatta gaacaagcac aaattcagca agagaagaat atgtatgaac tacaaaagtt   8100
aaatagctgg gatgtttttg gtaactggtt tgacttaacc tcctggatca agtatattca   8160
atatggagtt tatataataa taggaatagt agttcttaga atagtaatat atatagtaca   8220
gatgttaagt agacttagaa agggctatag gcctgttttc tcttccccc ccggttacct    8280 ccaacagatc catatccaca aggactggga acagccagcc agagaagaaa cagaagaaga   8340
cgttggaaac aacgttggag acagctcgtg gccttggccg ataagatata cattcct     8400 gatccaccag ctgattcgcc tcttggccgg actatacaac atctgcagga acttactatc   8460
caggatctcc ctgaccctcc gaccagtttt ccagagtctt cagagggcac tgacagcaat   8520
cagagactgg ctaagaactg acgcagccta cttgcagtat gggtgcgagt ggatccaagg   8580
agcgttccag gccttcgcaa gggctacgag agagactctt gcgggcacgt ggagagactt   8640 gtgggggca ctgcagcgga tcgggagggg aatacttgca gtcccaagaa gaatcaggca    8700
gggagcagag atcgccctcc tatgagggac agcggtatca gcaggagac tttatgaata    8760 ccccatggag aaccccagca aagaagggg agaagaatt gtacaagcaa caaaatagag     8820
atgatgtaga ttcggatgat gatgacctag tagggggtctc tgtcacacca agagtaccac   8880
taagagaatt gacacataga ttagcaatag atgtgtcaca ttttataaaa gaaaagggg     8940 gactggaagg gatgtattac agtgagagaa gacatagaat cttagacata taccttgaaa   9000
aggaagaagg gataattgca gattggcaga actatactca tgggccagga ataagatacc   9060
caatgttctt tgggtggcta tggaagctag taccagtaga tgtcacacga caggaggagg   9120
acgatgggac tcactgttta ctacacccag cacaaacaag caggtttgat gacccgcatg   9180
gggaaacact gatatggaag tttgacccca cgctggctca tgattacaag gcttttatcc   9240
tgcacccaga ggaatttggg cataagtcag gcctgccaga agaagactgg aaggcaagac   9300
tgaaagcaag agggatacca tttagttaga gacaggaaca gctatatttg gccagggcag   9360
gaaataacta ctgaaaacag ctgagactgc agggactttc gaaggggct gtaaccaggg    9420 gagggacatg ggaggagccg gtggggaacg ccctcatact ttctgtataa agatacccgc   9480
tgcttgcatt gtacttcagt cgctctgcgg agaggctggc agattgagcc ctgggaggtt   9540
```

-continued

```
ctctccagca ctagcaggta gagcctgggt gttccctgct agactctcac cggtgcttgg    9600
ccggcactgg gcagacggct ccacgcttgc ttgcttaaaa gacctcttaa taaagctgcc    9660
agttagaagc aagttaagtg tgtgttccca tctctcctag tcgccgcctg gtc           9713

<210> SEQ ID NO 387
<211> LENGTH: 11878
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387
gcctcactga ttaagcattg gtaactgtca gaccaagttt actcatatat actttagatt      60
gatttaaaac ttcattttta atttaaaagg atctaggtga agatcctttt tgataatctc     120
atgaccaaaa tcccttaacg tgagttttcg ttccactgag cgtcagaccc cgtagaaaag    180
atcaaaggat cttcttgaga tccttttttt ctgcgcgtaa tctgctgctt gcaaacaaaa    240
aaaccaccgc taccagcggt ggtttgtttg ccggatcaag agctaccaac tcttttttccg    300 aaggtaactg gcttcagcag agcgcagata ccaaatactg ttcttctagt gtagccgtag    360
ttaggccacc acttcaagaa ctctgtagca ccgcctacat acctcgctct gctaatcctg    420
ttaccagtgg ctgctgccag tggcgataag tcgtgtctta ccgggttgga ctcaagacga    480
tagttaccgg ataaggcgca gcggtcgggc tgaacggggg gttcgtgcac acagcccagc    540
ttggagcgaa cgacctacac cgaactgaga tacctacagc gtgagctatg agaaagcgcc    600
acgcttcccg aagggagaaa ggcggacagg tatccggtaa gcggcagggt cggaacagga    660
gagcgcacga gggagcttcc agggggaaac gcctggtatc tttatagtcc tgtcgggttt    720
cgccacctct gacttgagcg tcgatttttg tgatgctcgt caggggggcg gagcctatgg    780
aaaaacgcca gcaacgcggc ctttttacgg ttcctggcct tttgctggcc ttttgctcac    840
atgttctttc ctgcgttatc ccctgattct gtggataacc gtattaccgc ctttgagtga    900
gctgataccg ctcgccgcag ccgaacgacc gagcgcagcg agtcagtgag cgaggaagcg    960
gaagagcgcc caatacgcaa accgcctctc cccgcgcgtt ggccgattca ttaatgcagc   1020
tggcacgaca ggtttcccga ctggaaagcg ggcagtgagc gcaacgcaat taatgtgagt   1080
tagctcactc attaggcacc ccaggcttta cactttatgc ttccggctcg tatgttgtgt   1140
ggaattgtga gcggataaca atttcacaca ggaaacagct atgaccatga ttacgccaag   1200
ctatttaggt gacactatag aatactcaag cttgggggga tcctctagag tcgacctgca   1260
ggcatgctat tgatgaatt aactacactt aaaataatac aattattatt aaattttttt   1320
ttgatttatt tattaatttt taaacttaat catttgtatt tgggaggaat tatatatatc   1380
tttataatta ttttattttt ttttattttt ttattttttt attattatta ttttttttta   1440
tttttttttt ttactgtatc aaagaaaaac ctttaaaaaa aaaattataa tttccccatc   1500
ttactatatt tttaatacat acgttttaag gaattaaatt agacaaaagc tatattatgc   1560
tttacatata attagaattt ataaacgttt ggttattaga tatttcatgt ctcagtaaag   1620
tctttcaata catatgtaaa aaaatatata tgaatacaca taagttgtta atatatttta   1680
tatgcataaa tgtataaata tatatatata tatatatata tgtatgtatg tatatgtgtg   1740
tatatgaaat tatttcaatg tttaattttt taaattttaa tttttttttt ttttttttt    1800 tttattatgt atattgatct ttattattta aatattactt ttttcgtttt ttcttctttt   1860
```

```
tattattttt tttttttttt atattttata caaatggtaa ttcaaataaa aggtataaat    1920
ttatatttaa ttttctttta tggataaata aagaaaaat ataaatatat aaaaatataa    1980
aaatatatat atgtatattg gggtgatgat aaaatgaaag ataatatata tatatatata    2040
tctttatttt ttttttttg tagacccat tgtgagtaca taaatatatt atataactcg    2100
ggagcatcag tcatggaatt cttatttctt tttcttttt gcctggccgg ccttttcgt    2160 ggccgccggc cttttgtcgc ctcccagctg agacaggtcg atccgtgtct cgtacaggcc    2220
ggtgatgctc tggtggatca gggtggcgtc cagcacctct ttggtgctgg tgtacctctt    2280
ccggtcgatg gtggtgtcaa agtacttgaa ggcggcaggg gctcccagat tggtcagggt    2340
aaacaggtgg atgatattct cggcctgctc tctgatgggc ttatcccggt gcttgttgta    2400
ggcggacagc actttgtcca gattagcgtc ggccaggatc actctcttgg agaactcgct    2460
gatctgctcg atgatctcgt ccaggtagtg cttgtgctgt ccacaaaca gctgtttctg    2520 ctcattatcc tcggggagc ccttcagctt ctcatagtgg ctggccaggt acaggaagtt    2580
cacatatttg gagggcaggg ccagttcgtt tcccttctgc agttcgccgg cagaggccag    2640
cattctcttc cggccgtttt ccagctcgaa cagggagtac ttaggcagct tgatgatcag    2700 gtccttttc acttctttgt agcccttggc ttccagaaag tcgatgggat tcttctcgaa    2760
gctgcttctt tccatgatgg tgatccccag cagctctttc acactcttca gtttcttgga    2820
cttgcccttt tccactttgg ccaccaccag cacagaatag gccacggtgg ggctgtcgaa    2880
gccgccgtac ttcttagggt cccagtcctt ctttctggcg atcagcttat cgctgttcct    2940
cttgggcagg atagactctt tgctgaagcc gcctgtctgc acctcggtct ttttcacgat    3000
attcacttgg ggcatgctca gcactttccg cacggtggca aaatcccggc ccttatccca    3060
cacgatctcc ccgtttcgc cgtttgtctc gatcagaggc cgcttccgga tctcgccgtt    3120
ggccagggta atctcggtct tgaaaagtt catgatgttg ctgtagaaga agtacttggc    3180
ggtagccttg ccgatttcct gctcgctctt ggcgatcatc ttccgcacgt cgtacacctt    3240
gtagtcgccg tacacgaact cgctttccag cttagggtac ttttttgatca gggcggttcc    3300 cacgacggcg ttcaggtagg cgtcgtgggc gtggtggtag ttgttgatct cgcgcactt    3360 gtaaaactgg aaatccttcc ggaaatcgga caccagcttg acttcagggg tgatcacttt    3420
cacttcccgg atcagcttgt cattctcgtc gtacttagtg ttcatccggg agtccaggat    3480
ctgtgccacg tgctttgtga tctgccgggt ttccaccagc tgtctcttga tgaagccggc    3540
cttatccagt cgctcaggc cgcctctctc ggccttggtc agattgtcga actttctctg    3600
ggtaatcagc ttggcgttca gcagctgccg ccagtagttc ttcatcttct tcacgacctc    3660
ttcggagggc acgttgtcgc tcttgccccg gttcttgtcg cttctggtca gcaccttgtt    3720
gtcgatggag tcgtccttca gaaagctctg aggcacgata tggtccacat cgtagtcgga    3780
cagccggttg atgtccagtt cctggtccac gtacatatcc cgcccattct gcaggtagta    3840
caggtacagc ttctcgttct gcagctgggt gttttccacg gggtgttctt tcaggatctg    3900
gctgcccagc tctttgatgc cctcttcgat ccgcttcatt ctctcgcggc tgttcttctg    3960
tcccttctgg gtggtctggt tctctctggc catttcgatc acgatgttct cgggcttgtg    4020
ccggcccatc actttcacga gctcgtccac caccttcact gtctgcagga tgcccttctt    4080
aatggcgggg ctgccggcca gattggcaat gtgctcgtgc aggctatcgc cctggccgga    4140
cacctgggct ttctgatgt cctctttaaa ggtcaggctg tcgtcgtgga tcagctgcat    4200
gaagtttctg ttggcgaagc cgtcggactt caggaaatcc aggattgtct tgccggactg    4260
```

```
cttgtcccgg atgccgttga tcagcttccg gctcagcctg ccccagccgg tgtatctccg    4320
ccgcttcagc tgcttcatca ctttgtcgtc gaacaggtgg gcataggttt tcagccgttc    4380
ctcgatcatc tctctgtcct caaacagtgt cagggtcagc acgatatctt ccagaatgtc    4440
ctcgttttcc tcattgtcca ggaagtcctt gtccttgata attttcagca gatcgtggta    4500
tgtgcccagg gaggcgttga accgatcttc cacgccggag atttccacgg agtcgaagca    4560
ctcgattttc ttgaagtagt cctctttcag ctgcttcacg gtcactttcc ggttggtctt    4620
gaacagcagg tccacgatgg cctttttctg ctcgccgctc aggaaggcgg gctttctcat    4680
tccctcggtc acgtatttca ctttggtcag ctcgttatac acggtgaagt actcgtacag    4740
caggctgtgc ttgggcagca ccttctcgtt gggcaggttc ttatcgaagt tggtcatccg    4800
ctcgatgaag ctctgggcgg aagcgccctt gtccaccact tcctcgaagt tccaggggggt    4860 gatggtttcc tcgctctttc tggtcatcca ggcgaatctg ctgtttcccc tggccagagg    4920
gcccacgtag taggggatgc ggaaggtcag gatcttctcg atcttttccc ggttgtcctt    4980
caggaatggg taaaaatctt cctgccgccg cagaatggcg tgcagctctc ccaggtggat    5040
ctggtggggg atgctgccgt tgtcgaaggt ccgctgcttc cgcagcaggt cctctctgtt    5100
cagcttcacg agcagttcct cggtgccgtc catcttttcc aggatgggct tgatgaactt    5160
gtagaactct tcctggctgg ctccgccgtc aatgtagccg gcgtagccgt tcttgctctg    5220
gtcgaagaaa atctctttgt acttctcagg cagctgctgc cgcacgagag ctttcagcag    5280
ggtcaggtcc tggtggtgct cgtcgtatct cttgatcata gaggcgctca gggggggcctt    5340 ggtgatctcg gtgttcactc tcaggatgtc gctcagcagg atggcgtcgg acaggttctt    5400
ggcggccaga acaggtcgg cgtactggtc gccgatctgg gccagcaggt tgtccaggtc    5460
gtcgtcgtag gtgtccttgc tcagctgcag tttggcatcc tcggccaggt cgaagttgct    5520
cttgaagttg ggggtcaggc ccaggctcag ggcaatcagg tttccgaaca ggccattctt    5580
cttctcgccg ggcagctggg cgatcagatt ttccagccgt ctgctcttgc tcagtctggc    5640
agacaggatg gccttggcgt ccacgccgct ggcgttgatg gggttttcct cgaacagctg    5700
gttgtaggtc tgcaccagct ggatgaacag cttgtccacg tcgctgttgt cggggttcag    5760
gtcgccctcg atcaggaagt ggccccggaa cttgatcatg tgggccaggg ccagatagat    5820
cagccgcagg tcggccttgt cggtgctgtc caccagtttc tttctcaggt ggtagatggt    5880
ggggtacttc tcgtggtagg ccacctcgtc cacgatgttg ccgaagatgg ggtgccgctc    5940
gtgcttctta tcctcttcca ccaggaagga ctcttccagt ctgtggaaga agctgtcgtc    6000
caccttggcc atctcgttgc tgaagatctc ttgcagatag cagatccggt tcttccgtct    6060
ggtgtatctt cttctggcgg ttctcttcag ccgggtggcc tcggctgttt cgccgctgtc    6120
gaacagcagg gctccgatca ggttcttctt gatgctgtgc cggtcggtgt tgcccagcac    6180
cttgaatttc ttgctgggca ccttgtactc gtcggtgatc acggcccagc ccacagagtt    6240
ggtgccgatg tccaggccga tgctgtactt cttgtcggct gctgggactc cgtggatacc    6300
gaccttccgc ttcttctttg gggccatctt atcgtcatcg tctttgtaat caatatcatg    6360
atccttgtag tctccgtcgt ggtccttata gtccattttt ctcgagggat cctgatatat    6420
ttctattagg tatttattat tataaaatat aaatcttgaa tgataataaa taaaatatta    6480
gttattcctt ttcagtttta aaatatacat attataaata tatatatata tatatatatt    6540
tttattgtga caagaatata taattataaa ttatattatt tattttttgta ttttttttttt    6600
```

```
tttttttttt tttttcttttt tttgttttat ttttcttttt ttttataaat attatttttt    6660
tcttttatca tgcacattgg aataatacat taatatatat atatatatta tattatacat    6720
atattgaata atgtttataa aaaatgcata acttatatga atataatttt ttttaaatat    6780
gacaaaaaga aaaaaaaaaa aaaccaaaaa aaattaaaat tgaaatgaaa tatataaata    6840
tattatttat atatattata cattgtttaa tactactaca tgtatatata tatattatat    6900
atatatatat atatcaattt tttcaaaaat aaattaaaat aaaagagggg gaaaaaaaaa    6960
aaaaaaaaaa aaaaagata attaagtaag catttaaaaa tatataaatt gataatatat    7020
aaaattaatc acatataaaa gcttataaac actaggttag ctaattcgct tgtaagaggt    7080
actctcgttt atgcaaaact atttgatata gcattttaac aagtacacat atatatatgt    7140
aatatatata ctatatatat ctattgcatg tgtactaagc atgtgcatgg catccccttt    7200
ttctcgtgtt taaaacagtt tgtatgataa aatataaagg atttgaaaaa gagaaaaaaa    7260
tatatgatct catcctatat agcgccataa ttttttatttg ggttgaataa aattttctac    7320
taaatttagg tgtaagtaaa ataatggaat atatataagt acaataaaaa agtgcataaa    7380
ttaaaaaatt tttataataa atattttttt taaaaaagtc aataataata ttaaatatat    7440
ataacacagg attatatatg ttcactacaa ttttttatat tataatataa attcttttca    7500
attttcattt tattttacat acactttcct tttttgtcac tatattttaa tattcacata    7560
tttagtttaa atactggcta tttctttcta catttgctag taacaattgt gtagtgctta    7620
aatatataca cacacctaaa acttacaaag tatcctagga ccatggccaa gcctttgtct    7680
caagaagaat ccaccctcat tgaaagagca acggctacaa tcaacagcat ccccatctct    7740
gaagactaca gcgtcgccag cgcagctctc tctagcgacg gccgcatctt cactggtgtc    7800
aatgtatatc attttactgg gggaccttgt gcagaactcg tggtgctggg cactgctgct    7860
gctgcggcag ctggcaacct gacttgtatc gtcgcgatcg gaaatgagaa caggggcatc    7920
ttgagcccct gcggacggtg ccgacaggtg cttctcgatc tgcatcctgg gatcaaagcc    7980
atagtgaagg acagtgatgg acagccgacg gcagttggga ttcgtgaatt gctgccctct    8040
ggttatgtgt gggagggcta accgcgggta ccccattaaa tttatttaat aatagattaa    8100
aaatattata aaaataaaaa cataaacaca gaaattacaa aaaaaataca tatgaatttt    8160
ttttttgtaa tcttccttat aaatatagaa taatgaatca tataaaacat atcattattc    8220
atttatttac atttaaaatt attgtttcag tatctttaat ttattatgta tatataaaaa    8280
taacttacaa ttttattaat aaacaatata tgtttattaa ttcatgtttt gtaatttatg    8340
ggatagcgat ttttttttact gtctgtattt tcttttttaa ttatgtttta attgtattta    8400
ttttattttt attattgttc tttttatagt attattttaa aacaaaatgt attttctaag    8460
aacttataat aataataata taaattttaa taaaaattat atttatcttt tacaatatga    8520
acataaagta caacattaat atatagcttt taatattttt attcctaatc atgtaaatct    8580 taaattttc tttttaaaca tatgttaaat atttatttct cattatatat aagaacatat    8640
ttattacatc tagaggtacc gagctcgttt tcgacactgg atggcggcgt tagtatcgaa    8700
tcgacagcag tatagcgacc agcattcaca tacgattgac gcatgatatt actttctgcg    8760
cacttaactt cgcatctggg cagatgatgt cgaggcgaaa aaaatataaa atcacgctaa    8820
catttgatta aaatagaaca actacaatat aaaaaaacta tacaaatgac aagttcttga    8880
aaacaagaat cttttttattg tcagtactga ttagaaaaac tcatcgagca tcaaatgaaa    8940
ctgcaattta ttcatatcag gattatcaat accatatttt tgaaaaagcc gtttctgtaa    9000
```

```
tgaaggagaa aactcaccga ggcagttcca taggatggca agatcctggt atcggtctgc    9060
gattccgact cgtccaacat caatacaacc tattaatttc ccctcgtcaa aaataaggtt    9120
atcaagtgag aaatcaccat gagtgacgac tgaatccggt gagaatggca aaagcttatg    9180
catttctttc cagacttgtt caacaggcca gccattacgc tcgtcatcaa aatcactcgc    9240
atcaaccaaa ccgttattca ttcgtgattg cgcctgagcg agacgaaata cgcgatcgct    9300
gttaaaagga caattacaaa caggaatcga atgcaaccgg cgcaggaaca ctgccagcgc    9360
atcaacaata ttttcacctg aatcaggata ttcttctaat acctggaatg ctgttttgcc    9420
ggggatcgca gtggtgagta accatgcatc atcaggagta cggataaaat gcttgatggt    9480
cggaagaggc ataaattccg tcagccagtt tagtctgacc atctcatctg taacatcatt    9540
ggcaacgcta cctttgccat gtttcagaaa caactctggc gcatcgggct tcccatacaa    9600
tcgatagatt gtcgcacctg attgcccgac attatcgcga gcccatttat acccatataa    9660
atcagcatcc atgttggaat ttaatcgcgg cctcgaaacg tgagtctttt ccttacccat    9720
ggttgtttat gttcggatgt gatgtgagaa ctgtatccta gcaagatttt aaaaggaagt    9780
atatgaaaga agaacctcag tggcaaatcc taacctttta tatttctcta caggggcgcg    9840
gcgtggggac aattcaacgc gtctgtgagg ggagcgtttc cctgctcgca ggtctgcagc    9900
gaggagccgt aattttgct tcgcgccgtg cggccatcaa aatgtatgga tgcaaatgat     9960
tatacatggg gatgtatggg ctaaatgtac gggcgacagt cacatcatgc ccctgagctg   10020
cgcacgtcaa gactgtcaag gagggtattc tgggcctcca tgtcgctggc ctaacattag   10080
taatgtaggt ctgactttca ctcatataag tcttatggta actaaactaa ggtcttacct   10140
ttactgatat atgtcttact ttcactaact taggtattac ttttactaac ttaggtctta   10200
aattcagtaa ctaaggtcat acttcgacta actaaggtct tacattcact gatataggtc   10260
ttatgattac taacttaggt cctaatttga ctaacataag tcctaacatt agtaatgtag   10320
gtcttaactt aactaactta ggtcttacct tcactaatat aggtcttaat attactgact   10380
taagtaatta aggtactaac ttaggtcgta aggtaactaa tatataggtc ttaaggtaac   10440
taatttaggt cttgacttaa taaatatagg tcctaacata aatagtatag gtcctaatat   10500
aagtactata ggccttaact taaccaacat aggtcctaac ataagttata taggtcttaa   10560
cgtaactaac ataagtcatt aaggtactaa gtttggtctt aatttaacaa taacatgtcg   10620
ctggcctaac attagtaatg taggtctgac tttcactcat ataagtctta tggtaactaa   10680
actaaggtct tacctttact gatatatgtc ttactttcac taacttaggt attacttttta  10740 ctaacttagg tcttaaattc agtaactaag gtcatacttc gactaactaa ggtcttacat   10800
tcactgatat aggtcttatg attactaact taggtcctaa tttgactaac ataagtccta   10860
acattagtaa tgtaggtctt aacttaacta acttaggtct taccttcact aatataggtc   10920
ttaatattac tgacttaagt aattaaggta ctaacttagg tcgtaaggta actaatatat   10980
aggtcttaag gtaactaatt taggtcttga cttaataaat ataggtccta acataaatag   11040
tataggtcct aatataagta ctataggcct taacttaacc aacataggtc ctaacataag   11100
ttatataggt cttaacgtaa ctaacataag tcattaaggt actaagtttg gtcttaattt   11160
aacaataacc atgtcgctgg ccgggtggtc ttaatttaac aaatatagac catgtcgctg   11220
gccgggtgac ccggcgggga cgaggcaagc taaacagatc ctcgtgatac gcctattttt   11280
ataggttaat gtcatgataa taatggtttc ttaggacgga tcgcttgcct gtaacttaca   11340
```

```
cgcgcctcgt atcttttaat gatggaataa tttgggaatt tactctgtgt ttatttattt    11400
ttatgttttg tatttggatt ttagaaagta aataaagaag gtagaagagt tacggaatga    11460
agaaaaaaaa ataaacaaag gtttaaaaaa tttcaacaaa aagcgtactt tacatatata    11520
tttattagac aagaaaagca gattaaatag atatacattc gattaacgat aagtaaaatg    11580
taaaatcaca ggattttcgt gtgtggtctt ctacacagac aagatgaaac aattcggcat    11640
taatacctga gagcaggaag agcaagataa aaggtagtat ttgttggcga tcccctaga    11700 gtcttttaca tcttcggaaa acaaaaacta ttttttcttt aatttctttt tttactttct    11760
atttttaatt tatatattta tattaaaaaa tttaaattat aattattttt atagcacgtg    11820
atgaaaagga cccaggtggc acttttcggg gaaatctcga cctgcagcgt acgaagct     11878

<210> SEQ ID NO 388
<211> LENGTH: 12044
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 388
gcctcactga ttaagcattg gtaactgtca gaccaagttt actcatatat actttagatt      60
gatttaaaac ttcatttta atttaaaagg atctaggtga agatcctttt tgataatctc     120
atgaccaaaa tcccttaacg tgagttttcg ttccactgag cgtcagaccc cgtagaaaag    180
atcaaaggat cttcttgaga tcctttttt ctgcgcgtaa tctgctgctt gcaaacaaaa    240
aaaccaccgc taccagcggt ggtttgtttg ccggatcaag agctaccaac tcttttccg    300 aaggtaactg gcttcagcag agcgcagata ccaaatactg ttcttctagt gtagccgtag    360
ttaggccacc acttcaagaa ctctgtagca ccgcctacat acctcgctct gctaatcctg    420
ttaccagtgg ctgctgccag tggcgataag tcgtgtctta ccgggttgga ctcaagacga    480
tagttaccgg ataaggcgca gcggtcgggc tgaacggggg gttcgtgcac acagcccagc    540
ttggagcgaa cgacctacac cgaactgaga tacctacagc gtgagctatg agaaagcgcc    600
acgcttcccg aagggagaaa ggcggacagg tatccggtaa gcggcagggt cggaacagga    660
gagcgcacga gggagcttcc agggggaaac gcctggtatc tttatagtcc tgtcgggttt    720
cgccacctct gacttgagcg tcgatttttg tgatgctcgt caggggggcg gagcctatgg    780
aaaaacgcca gcaacgcggc cttttacgg ttcctggcct tttgctggcc ttttgctcac    840
atgttctttc ctgcgttatc ccctgattct gtggataacc gtattaccgc ctttgagtga    900
gctgataccg ctcgccgcag ccgaacgacc gagcgcagcg agtcagtgag cgaggaagcg    960
gaagagcgcc caatacgcaa accgcctctc cccgcgcgtt ggccgattca ttaatgcagc    1020
tggcacgaca ggtttcccga ctggaaagcg ggcagtgagc gcaacgcaat taatgtgagt    1080
tagctcactc attaggcacc ccaggcttta cactttatgc ttccggctcg tatgttgtgt    1140
ggaattgtga gcggataaca atttcacaca ggaaacagct atgaccatga ttacgccaag    1200
ctatttaggt gacactatag aatactcaag cttgggggga tcctctagag tcgactaata    1260
cgactcacta taggaacata atctatagcg gcgttttaga gctagaaata gcaagttaaa    1320
ataaggctag tccgttatca acttgaaaaa gtggcaccga gtcggtgcta gcataacccc    1380
ttggggcctc taaacgggtc ttgaggggtt ttttggtcga cctgcaggca tgctatttga    1440
tgaattaact acacttaaaa taatacaatt attattaaat ttttttttga tttatttatt    1500
```

```
aatttttaaa cttaatcatt tgtatttggg aggaattata tatatcttta taattatttt    1560 atttttttt attttttat ttttttatta ttattatttt tttttatttt ttttttttac      1620
tgtatcaaag aaaaaccttt aaaaaaaaaa ttataatttc cccatcttac tatattttta    1680
atacatacgt tttaaggaat taaattagac aaaagctata ttatgcttta catataatta    1740
gaatttataa acgtttggtt attagatatt tcatgtctca gtaaagtctt tcaatacata    1800
tgtaaaaaaa tatatatgaa tacacataag ttgttaatat attttatatg cataaatgta    1860
taaatatata tatatatata tatatatgta tgtatgtata tgtgtgtata tgaaattatt    1920
tcaatgttta atttttaaa ttttaatttt tttttttttt tttttttta ttatgtatat      1980 tgatctttat tatttaaata ttactttttt cgttttttct tcttttatt attttttttt     2040 tttttatat tttatacaaa tggtaattca aataaaaggt ataaatttat atttaatttt     2100
cttttatgga taaataaaag aaaaatataa atatataaaa atataaaaat atatatatgt    2160
atattggggt gatgataaaa tgaaagataa tatatatata tatatatctt tattttttt    2220 tttttgtaga ccccattgtg agtacataaa tatattat aactcgggag catcagtcat      2280
ggaattctta tttctttttc tttttgcct ggccggcctt tttcgtggcc gccggccttt     2340
tgtcgcctcc cagctgagac aggtcgatcc gtgtctcgta caggccggtg atgctctggt    2400
ggatcagggt ggcgtccagc acctctttgg tgctggtgta cctcttccgg tcgatggtgg    2460
tgtcaaagta cttgaaggcg gcaggggctc ccagattggt cagggtaaac aggtggatga    2520
tattctcggc ctgctctctg atgggcttat cccggtgctt gttgtaggcg gacagcactt    2580
tgtccagatt agcgtcggcc aggatcactc tcttggagaa ctcgctgatc tgctcgatga    2640
tctcgtccag gtagtgcttg tgctgttcca caaacagctg tttctgctca ttatcctcgg    2700
gggagccctt cagcttctca tagtggctgg ccaggtacag gaagttcaca tatttggagg    2760
gcagggccag ttcgtttccc ttctgcagtt cgccggcaga ggccagcatt ctcttccggc    2820
cgttttccag ctcgaacagg gagtacttag gcagcttgat gatcaggtcc ttttcactt     2880 ctttgtagcc cttggcttcc agaaagtcga tgggattctt ctcgaagctg cttctttcca    2940
tgatggtgat ccccagcagc tctttcacac tcttcagttt cttggacttg ccctttttcca   3000 ctttggccac caccagcaca gaataggcca cggtgggggct gtcgaagccg ccgtacttct    3060
tagggtccca gtccttcttt ctggcgatca gcttatcgct gttcctcttg ggcaggatag    3120
actctttgct gaagccgcct gtctgcacct cggtcttttt cacgatattc acttggggca    3180
tgctcagcac tttccgcacg gtggcaaaat cccggccctt atcccacacg atctccccgg    3240
tttcgccgtt tgtctcgatc agaggccgct tccggatctc gccgttggcc agggtaatct    3300
cggtcttgaa aaagttcatg atgttgctgt agaagaagta cttggcggta gccttgccga    3360
tttcctgctc gctcttggcg atcatcttcc gcacgtcgta caccttgtag tcgccgtaca    3420
cgaactcgct ttccagctta gggtactttt tgatcagggc ggttcccacg acggcgttca    3480
ggtaggcgtc gtgggcgtgg tggtagttgt tgatctcgcg cactttgtaa aactggaaat    3540
ccttccggaa atcggacacc agcttggact tcagggtgat cactttcact tcccggatca    3600
gcttgtcatt ctcgtcgtac ttagtgttca tccgggagtc caggatctgt gccacgtgct    3660
ttgtgatctg ccgggtttcc accagctgtc tcttgatgaa gccggcctta tccagttcgc    3720
tcaggccgcc tctctcggcc ttggtcagat tgtcgaactt tctctgggta atcagcttgg    3780
cgttcagcag ctgccgccag tagttcttca tcttcttcac gacctcttcg gagggcacgt    3840
tgtcgctctt gccccggttc ttgtcgcttc tggtcagcac cttgttgtcg atggagtcgt    3900
```

```
ccttcagaaa gctctgaggc acgatatggt ccacatcgta gtcggacagc cggttgatgt    3960
ccagttcctg gtccacgtac atatcccgcc cattctgcag gtagtacagg tacagcttcc    4020
cgttctgcag ctgggtgttt tccacggggt gttctttcag gatctggctg cccagctctt    4080
tgatgccctc ttcgatccgc ttcattctct cgcggctgtt cttctgtccc ttctgggtgg    4140
tctggttctc tctggccatt tcgatcacga tgttctcggg cttgtgccgg cccatcactt    4200
tcacgagctc gtccaccacc ttcactgtct gcaggatgcc cttcttaatg gcgggggctgc   4260 cggccagatt ggcaatgtgc tcgtgcaggc tatcgccctg gccggacacc tgggctttct    4320
ggatgtcctc tttaaaggtc aggctgtcgt cgtggatcag ctgcatgaag tttctgttgg    4380
cgaagccgtc ggacttcagg aaatccagga ttgtcttgcc ggactgcttg tcccggatgc    4440
cgttgatcag cttccggctc agcctgcccc agccggtgta tctccgccgc ttcagctgct    4500
tcatcacttt gtcgtcgaac aggtgggcat aggttttcag ccgttcctcg atcatctctc    4560
tgtcctcaaa cagtgtcagg gtcagcacga tatcttccag aatgtcctcg ttttcctcat    4620
tgtccaggaa gtccttgtcc ttgataattt tcagcagatc gtggtatgtg cccagggagg    4680
cgttgaaccg atcttccacg ccggagattt ccacggagtc gaagcactcg attttcttga    4740
agtagtcctc tttcagctgc ttcacggtca ctttccggtt ggtcttgaac agcaggtcca    4800
cgatggcctt tttctgctcg ccgctcagga aggcgggctt tctcattccc tcggtcacgt    4860
atttcacttt ggtcagctcg ttatacacgg tgaagtactc gtacagcagg ctgtgcttgg    4920
gcagcacctt ctcgttgggc aggttcttat cgaagttggt catccgctcg atgaagctct    4980
gggcggaagc gcccttgtcc accacttcct cgaagttcca gggggtgatg gtttcctcgc    5040
tctttctggt catccaggcg aatctgctgt ttccccctggc cagagggccc acgtagtagg    5100
ggatgcggaa ggtcaggatc ttctcgatct tttcccggtt gtccttcagg aatgggtaaa    5160
aatcttcctg ccgccgcaga atggcgtgca gctctcccag gtggatctgg tggggggatgc   5220 tgccgttgtc gaaggtccgc tgcttccgca gcaggtcctc tctgttcagc ttcacgagca    5280
gttcctcggt gccgtccatc ttttccagga tgggcttgat gaacttgtag aactcttcct    5340
ggctggctcc gccgtcaatg tagccggcgt agccgttctt gctctggtcg aagaaaatct    5400
ctttgtactt ctcaggcagc tgctgccgca cgagagcttt cagcagggtc aggtcctggt    5460
ggtgctcgtc gtatctcttg atcatagagg cgctcagggg ggccttggtg atctcggtgt    5520
tcactctcag gatgtcgctc agcaggatgg cgtcggacag gttcttggcg gccagaaaca    5580
ggtcggcgta ctggtcgccg atctgggcca gcaggttgtc caggtcgtcg tcgtaggtgt    5640
ccttgctcag ctgcagtttg gcatcctcgg ccaggtcgaa gttgctcttg aagttggggg    5700
tcaggcccag gctcagggca atcaggtttc cgaacaggcc attcttcttc tcgccgggca    5760
gctgggcgat cagattttcc agccgtctgc tcttgctcag tctggcagac aggatggcct    5820
tggcgtccac gccgctggcg ttgatggggt tttcctcgaa cagctggttg taggtctgca    5880
ccagctggat gaacagcttg tccacgtcgc tgttgtcggg gttcaggtcg ccctcgatca    5940
ggaagtggcc ccggaacttg atcatgtggg ccagggccag atagatcagc gcaggtcgg    6000 ccttgtcggt gctgtccacc agtttctttc tcaggtggta gatggtgggg tacttctcgt    6060
ggtaggccac ctcgtccacg atgttgccga agatggggtg ccgctcgtgc ttcttatcct    6120
cttccaccag gaaggactct tccagtctgt ggaagaagct gtcgtccacc ttggccatct    6180
cgttgctgaa gatctcttgc agatagcaga tccggttctt ccgtctggtg tatcttcttc    6240
```

```
tggcggttct cttcagccgg gtggcctcgg ctgtttcgcc gctgtcgaac agcagggctc    6300
cgatcaggtt cttcttgatg ctgtgccggt cggtgttgcc cagcaccttg aatttcttgc    6360
tgggcacctt gtactcgtcg gtgatcacgg cccagcccac agagttggtg ccgatgtcca    6420
ggccgatgct gtacttcttg tcggctgctg ggactccgtg gataccgacc ttccgcttct    6480
tctttggggc catcttatcg tcatcgtctt tgtaatcaat atcatgatcc ttgtagtctc    6540
cgtcgtggtc cttatagtcc attttttctcg agggatcctg atatatttct attaggtatt    6600
tattattata aaatataaat cttgaatgat aataaataaa atattagtta ttccttttct    6660
agtttaaaat atacatatta taaatatata tatatatata tatatttttta ttgtgacaag    6720 aatatataat tataaattat attatttatt tttgtatttt ttttttttttt tttttttttt    6780 tcttttttg ttttatttt ctttttttt ataaatatta tttttttctt ttatcatgca    6840
cattggaata atacattaat atatatatat atattatatt atacatatat tgaataatgt    6900
ttataaaaaa tgcataactt atatgaatat aattttttt aaatatgaca aaagagaaaa    6960
aaaaaaaaac caaaaaaaat taaaattgaa atgaaatata taaatatatt atttatatat    7020
attatacatt gtttaatact actacatgta tatatatata ttatatatat atatatatat    7080 caatttttc aaaaataaat taatataaaa agaggggaaa aaaaaaaaa aaaaaaaaa    7140 aagataatta agtaagcatt taaaaatata taaattgata atatataaaa ttaatcacat    7200
ataaaagctt ataaacacta ggttagctaa ttcgcttgta agaggtactc tcgtttatgc    7260
aaaactattt gatatagcat tttaacaagt acacatatat atatgtaata tatatactat    7320
atatatctat tgcatgtgta ctaagcatgt gcatggcatc ccctttttct cgtgtttaaa    7380
acagtttgta tgataaaata taaggatttt gaaaagaga aaaaaatata tgatctcatc    7440
ctatatagcg ccataatttt tatttgggtt gaataaaatt ttctactaaa tttaggtgta    7500
agtaaaataa tggaatatat ataagtacaa taaaaaagtg cataaattaa aaaatttta    7560 taataaaatat ttttttttaaa aaagtcaata ataatattaa atatatataa cacaggatta    7620
tatatgttca ctacaatttt ttatattata atataaattc ttttcaattt tcatttttatt    7680 ttacatacac tttccttttt tgtcactata ttttaatatt cacatattta gtttaaaatac    7740 tggctatttc tttctacatt tgctagtaac aattgtgtag tgcttaaata tatacacaca    7800
cctaaaactt acaaagtatc ctaggaccat ggccaagcct ttgtctcaag aagaatccac    7860
cctcattgaa agagcaacgg ctacaatcaa cagcatcccc atctctgaag actacagcgt    7920
cgccagcgca gctctctcta gcgacggccg catcttcact ggtgtcaatg tatatcattt    7980
tactggggga ccttgtgcag aactcgtggt gctgggcact gctgctgctg cggcagctgg    8040
caacctgact tgtatcgtcg cgatcggaaa tgagaacagg ggcatcttga gccctgcgg    8100 acggtgccga caggtgcttc tcgatctgca tcctgggatc aaagccatag tgaaggacag    8160
tgatggacag ccgacggcag ttgggattcg tgaattgctg ccctctggtt atgtgtggga    8220
gggctaaccg cgggtacccc attaaattta tttaataata gattaaaaat attataaaaa    8280
taaaaacata aacacagaaa ttacaaaaaa aatacatatg aatttttttt ttgtaatctt    8340
ccttataaat atagaataat gaatcatata aaacatatca ttattcattt atttacattt    8400
aaaattattg tttcagtatc tttaatttat tatgtatata taaaaataac ttacaatttt    8460
attaataaac aatatatgtt tattaattca tgttttgtaa tttatgggat agcgattttt    8520
tttactgtct gtatttttctt ttttaattat gtttaattg tatttatttt atttttatta    8580
ttgttctttt tatagtatta ttttaaaaca aaatgtattt tctaagaact tataataata    8640
```

```
ataatataaa ttttaataaa aattatattt atcttttaca atatgaacat aaagtacaac    8700
attaatatat agcttttaat attttttattc ctaatcatgt aaatcttaaa tttttctttt    8760
taaacatatg ttaaatattt atttctcatt atatataaga acatatttat tacatctaga    8820
ggtaccgagc tcgttttcga cactggatgg cggcgttagt atcgaatcga cagcagtata    8880
gcgaccagca ttcacatacg attgacgcat gatattactt tctgcgcact taacttcgca    8940
tctgggcaga tgatgtcgag gcgaaaaaaa atataaatca cgctaacatt tgattaaaat    9000
agaacaacta caatataaaa aaactataca aatgacaagt tcttgaaaac aagaatcttt    9060
ttattgtcag tactgattag aaaaactcat cgagcatcaa atgaaactgc aatttattca    9120
tatcaggatt atcaatacca tattttttgaa aaagccgttt ctgtaatgaa ggagaaaact    9180
caccgaggca gttccatagg atggcaagat cctggtatcg gtctgcgatt ccgactcgtc    9240
caacatcaat acaacctatt aatttcccct cgtcaaaaat aaggttatca agtgagaaat    9300
caccatgagt gacgactgaa tccggtgaga atggcaaaag cttatgcatt tctttccaga    9360
cttgttcaac aggccagcca ttacgctcgt catcaaaatc actcgcatca accaaaccgt    9420
tattcattcg tgattgcgcc tgagcgagac gaaatacgcg atcgctgtta aaaggacaat    9480
tacaaacagg aatcgaatgc aaccggcgca ggaacactgc cagcgcatca acaatatttt    9540
cacctgaatc aggatattct tctaatacct ggaatgctgt tttgccgggg atcgcagtgg    9600
tgagtaacca tgcatcatca ggagtacgga taaaatgctt gatggtcgga agaggcataa    9660
attccgtcag ccagtttagt ctgaccatct catctgtaac atcattgca acgctacctt    9720 tgccatgttt cagaaacaac tctggcgcat cgggcttccc atacaatcga tagattgtcg    9780
cacctgattg cccgacatta tcgcgagccc atttatacccc atataaatca gcatccatgt    9840
tggaatttaa tcgcggcctc gaaacgtgag tcttttcctt acccatggtt gtttatgttc    9900
ggatgtgatg tgagaactgt atcctagcaa gatttaaaaa ggaagtatat gaaagaagaa    9960
cctcagtggc aaatcctaac cttttatatt tctctacagg ggcgcggcgt ggggacaatt   10020
caacgcgtct gtgaggggag cgtttccctg ctcgcaggtc tgcagcgagg agccgtaatt   10080
tttgcttcgc gccgtgcggc catcaaaatg tatggatgca aatgattata catggggatg   10140
tatgggctaa atgtacgggc gacagtcaca tcatgcccct gagctgcgca cgtcaagact   10200
gtcaaggagg gtattctggg cctccatgtc gctggcctaa cattagtaat gtaggtctga   10260
ctttcactca tataagtctt atggtaacta aactaaggtc ttacctttac tgatatatgt   10320
cttactttca ctaacttagg tattactttt actaacttag gtcttaaatt cagtaactaa   10380
ggtcatactt cgactaacta aggtcttaca ttcactgata taggtcttat gattactaac   10440
ttaggtccta atttgactaa cataagtcct aacattagta atgtaggtct aacttaact    10500 aacttaggtc ttaccttcac taatataggt cttaatatta ctgacttaag taattaaggt   10560
actaacttag gtcgtaaggt aactaatata taggtcttaa ggtaactaat ttaggtcttg   10620
acttaataaa tataggtcct aacataaata gtataggtcc taatataagt actataggcc   10680
ttaacttaac caacataggt cctaacataa gttatatagg tcttaacgta actaacataa   10740
gtcattaagg tactaagttt ggtcttaatt taacaataac atgtcgctgg cctaacatta   10800
gtaatgtagg tctgactttc actcatataa gtcttatggt aactaaacta aggtcttacc   10860
tttactgata tatgtcttac tttcactaac ttaggtatta cttttactaa cttaggtctt   10920
aaattcagta actaaggtca tacttcgact aactaaggtc ttacattcac tgatataggt   10980
```

```
cttatgatta ctaacttagg tcctaatttg actaacataa gtcctaacat tagtaatgta   11040
ggtcttaact taactaactt aggtcttacc ttcactaata taggtcttaa tattactgac   11100
ttaagtaatt aaggtactaa cttaggtcgt aaggtaacta atatataggt cttaaggtaa   11160
ctaatttagg tcttgactta ataaatatag gtcctaacat aaatagtata ggtcctaata   11220
taagtactat aggccttaac ttaaccaaca taggtcctaa cataagttat ataggtctta   11280
acgtaactaa cataagtcat taaggtacta agtttggtct taatttaaca ataaccatgt   11340
cgctggccgg gtggtcttaa tttaacaaat atagaccatg tcgctggccg ggtgacccgg   11400
cggggacgag gcaagctaaa cagatcctcg tgatacgcct atttttatag gttaatgtca   11460
tgataataat ggtttcttag gacggatcgc ttgcctgtaa cttacacgcg cctcgtatct   11520
tttaatgatg gaataatttg ggaatttact ctgtgtttat ttattttttat gttttgtatt   11580 tggattttag aaagtaaata aagaaggtag aagagttacg gaatgaagaa aaaaaaataa   11640
acaaaggttt aaaaaatttc aacaaaaagc gtactttaca tatatattta ttagacaaga   11700
aaagcagatt aaatagatat acattcgatt aacgataagt aaaatgtaaa atcacaggat   11760
tttcgtgtgt ggtcttctac acagacaaga tgaaacaatt cggcattaat acctgagagc   11820
aggaagagca agataaaagg tagtatttgt tggcgatccc cctagagtct tttacatctt   11880
cggaaaacaa aaactatttt ttctttaatt tcttttttta ctttctattt ttaatttata   11940
tatttatatt aaaaaattta aattataatt attttatag cacgtgatga aaaggaccca   12000
ggtggcactt ttcggggaaa tctcgacctg cagcgtacga agct              12044
```

<210> SEQ ID NO 389
<211> LENGTH: 12044
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 389

```
gcctcactga ttaagcattg gtaactgtca gaccaagttt actcatatat actttagatt     60
gatttaaaac ttcatttta atttaaaagg atctaggtga agatcctttt tgataatctc    120
atgaccaaaa tcccttaacg tgagttttcg ttccactgag cgtcagaccc cgtagaaaag    180
atcaaaggat cttcttgaga tccttttttt ctgcgcgtaa tctgctgctt gcaaacaaaa    240
aaaccaccgc taccagcggt ggtttgtttg ccggatcaag agctaccaac tcttttccg    300 aaggtaactg gcttcagcag agcgcagata ccaaatactg ttcttctagt gtagccgtag    360
ttaggccacc acttcaagaa ctctgtagca ccgcctacat acctcgctct gctaatcctg    420
ttaccagtgg ctgctgccag tggcgataag tcgtgtctta ccgggttgga ctcaagacga    480
tagttaccgg ataaggcgca gcggtcgggc tgaacggggg gttcgtgcac acagcccagc    540
ttggagcgaa cgacctacac cgaactgaga tacctacagc gtgagctatg agaaagcgcc    600
acgcttcccg aagggagaaa ggcggacagg tatccggtaa gcggcagggt cggaacagga    660
gagcgcacga gggagcttcc agggggaaac gcctggtatc tttatagtcc tgtcgggttt    720
cgccacctct gacttgagcg tcgatttttg tgatgctcgt caggggggcg agcctatgg    780 aaaaacgcca gcaacgcggc ctttttacgg ttcctggcct tttgctggcc ttttgctcac    840
atgttctttc ctgcgttatc ccctgattct gtggataacc gtattaccgc ctttgagtga    900
gctgataccg ctcgccgcag ccgaacgacc gagcgcagcg agtcagtgag cgaggaagcg    960
```

-continued

```
gaagagcgcc caatacgcaa accgcctctc cccgcgcgtt ggccgattca ttaatgcagc    1020
tggcacgaca ggtttcccga ctggaaagcg ggcagtgagc gcaacgcaat taatgtgagt    1080
tagctcactc attaggcacc ccaggcttta cactttatgc ttccggctcg tatgttgtgt    1140
ggaattgtga gcggataaca atttcacaca ggaaacagct atgaccatga ttacgccaag    1200
ctatttaggt gacactatag aatactcaag cttgggggga tcctctagag tcgactaata    1260
cgactcacta taggaaatga tatggatttt gggttttaga gctagaaata gcaagttaaa    1320
ataaggctag tccgttatca acttgaaaaa gtggcaccga gtcggtgcta gcataacccc    1380
ttggggcctc taaacgggtc ttgaggggtt ttttggtcga cctgcaggca tgctatttga    1440
tgaattaact acacttaaaa taatacaatt attattaaat ttttttttga tttatttatt    1500
aattttaaa cttaatcatt tgtatttggg aggaattata tatatcttta taattatttt    1560
atttttttt attttttat ttttttatta ttattatttt tttttatttt ttttttttac    1620
tgtatcaaag aaaaacctt aaaaaaaaaa ttataatttc cccatcttac tatattttta    1680
atacatacgt tttaaggaat taaattagac aaaagctata ttatgcttta catataatta    1740
gaatttataa acgtttggtt attagatatt tcatgtctca gtaaagtctt tcaatacata    1800
tgtaaaaaaa tatatatgaa tacacataag ttgttaatat attttatatg cataaatgta    1860
taaatatata tatatatata tatatatgta tgtatgtata tgtgtgtata tgaaattatt    1920
tcaatgttta attttttaaa ttttaatttt ttttttttt ttttttttta ttatgtatat    1980
tgatctttat tatttaaata ttactttttt cgttttttct tctttttatt attttttttt    2040
tttttatat tttatacaaa tggtaattca aataaaaggt ataaatttat atttaatttt    2100
ctttttatgga taaataaaag aaaaatataa atatataaaa atataaaaat atatatatgt    2160
atattggggt gatgataaaa tgaaagataa tatatatata tatatatctt tattttttt    2220
tttttgtaga ccccattgtg agtacataaa tatattatat aactcgggag catcagtcat    2280
ggaattctta tttctttttc ttttttgcct ggccggcctt tttcgtggcc gccgccttt    2340
tgtcgcctcc cagctgagac aggtcgatcc gtgtctcgta caggccggtg atgctctggt    2400
ggatcagggg ggcgtccagc acctctttgg tgctggtgta cctcttccgg tcgatggtgg    2460
tgtcaaagta cttgaaggcg gcaggggctc ccagattggt cagggtaaac aggtggatga    2520
tattctcggc ctgctctctg atgggcttat cccggtgctt gttgtaggcg gacagcactt    2580
tgtccagatt agcgtcggcc aggatcactc tcttggagaa ctcgctgatc tgctcgatga    2640
tctcgtccag gtagtgcttg tgctgttcca caaacagctg tttctgctca ttatcctcgg    2700
gggagccctt cagcttctca tagtggctgg ccaggtacag gaagttcaca tatttggagg    2760
gcagggccag ttcgtttccc ttctgcagtt cgccggcaga ggccagcatt ctcttccggc    2820
cgttttccag ctcgaacagg gagtacttag gcagcttgat gatcaggtcc tttttcactt    2880
ctttgtagcc cttggcttcc agaaagtcga tgggattctt ctcgaagctg cttctttcca    2940
tgatggtgat ccccagcagc tctttcacac tcttcagttt cttggacttg ccctttccca    3000
ctttggccac caccagcaca gaataggcca cggtggggct gtcgaagccg ccgtacttct    3060
tagggtccca gtccttcttt ctggcgatca gcttatcgct gttcctcttg ggcaggatag    3120
actctttgct gaagccgcct gtctgcacct cggtcttttt cacgatattc acttggggca    3180
tgctcagcac tttccgcacg gtggcaaaat cccggccctt atcccacacg atctccccgg    3240
tttcgccgtt tgtctcgatc agaggccgct tccggatctc gccgttggcc agggtaatct    3300
cggtcttgaa aaagttcatg atgttgctgt agaagaagta cttggcggta gccttgccga    3360
```

```
tttcctgctc gctcttggcg atcatcttcc gcacgtcgta caccttgtag tcgccgtaca    3420
cgaactcgct ttccagctta gggtactttt tgatcagggc ggttcccacg acggcgttca    3480
ggtaggcgtc gtgggcgtgg tggtagttgt tgatctcgcg cactttgtaa aactggaaat    3540
ccttccggaa atcggacacc agcttggact tcagggtgat cactttcact tcccggatca    3600
gcttgtcatt ctcgtcgtac ttagtgttca tccgggagtc caggatctgt gccacgtgct    3660
ttgtgatctg ccgggtttcc accagctgtc tcttgatgaa gccggcctta tccagttcgc    3720
tcaggccgcc tctctcggcc ttggtcagat tgtcgaactt tctctgggta atcagcttgg    3780
cgttcagcag ctgccgccag tagttcttca tcttcttcac gacctcttcg gagggcacgt    3840
tgtcgctctt gccccggttc ttgtcgcttc tggtcagcac cttgttgtcg atggagtcgt    3900
ccttcagaaa gctctgaggc acgatatggt ccacatcgta gtcggacagc cggttgatgt    3960
ccagttcctg gtccacgtac atatcccgcc cattctgcag gtagtacagg tacagcttct    4020
cgttctgcag ctgggtgttt ccacgggggt gttctttcag gatctggctg cccagctctt    4080
tgatgccctc ttcgatccgc ttcattctct cgcggctgtt cttctgtccc ttctgggtgg    4140
tctggttctc tctggccatt tcgatcacga tgttctcggg cttgtgccgg cccatcactt    4200
tcacgagctc gtccaccacc ttcactgtct gcaggatgcc cttcttaatg gcggggctgc    4260
cggccagatt ggcaatgtgc tcgtgcaggc tatcgccctg gccggacacc tgggctttct    4320
ggatgtcctc tttaaaggtc aggctgtcgt cgtggatcag ctgcatgaag tttctgttgg    4380
cgaagccgtc ggacttcagg aaatccagga ttgtcttgcc ggactgcttg tcccggatgc    4440
cgttgatcag cttccggctc agcctgcccc agccggtgta tctccgccgc ttcagctgct    4500
tcatcacttt gtcgtcgaac aggtgggcat aggttttcag ccgttcctcg atcatctctc    4560
tgtcctcaaa cagtgtcagg gtcagcacga tatcttccag aatgtcctcg ttttcctcat    4620
tgtccaggaa gtccttgtcc ttgataattt tcagcagatc gtggtatgtg cccagggagg    4680
cgttgaaccg atcttccacg ccggagattt ccacggagtc gaagcactcg attttcttga    4740
agtagtcctc tttcagctgc ttcacggtca ctttccggtt ggtcttgaac agcaggtcca    4800
cgatggcctt tttctgctcg ccgctcagga aggcgggctt tctcattccc tcggtcacgt    4860
atttcacttt ggtcagctcg ttatacacgg tgaagtactc gtacagcagg ctgtgcttgg    4920
gcagcacctt ctcgttgggc aggttcttat cgaagttggt catccgctcg atgaagctct    4980
gggcggaagc gcccttgtcc accacttcct cgaagttcca gggggtgatg gtttcctcgc    5040
tctttctggt catccaggcg aatctgctgt ttccgctggc cagagggccc acgtagtagg    5100
ggatgcggaa ggtcaggatc ttctcgatct tttcccggtt gtccttcagg aatgggtaaa    5160
aatcttcctg ccgccgcaga atggcgtgca gctctcccag gtggatctgg tggggatgc    5220
tgccgttgtc gaaggtccgc tgcttccgca gcaggtcctc tctgttcagc ttcacgagca    5280
gttcctcggt gccgtccatc ttttccagga tgggcttgat gaacttgtag aactcttcct    5340
ggctggctcc gccgtcaatg tagccggcgt agccgttctt gctctggtcg aagaaaatct    5400
cttttgtactt ctcaggcagc tgctgccgca cgagagcttt cagcagggtc aggtcctggt    5460
ggtgctcgtc gtatctcttg atcatagagg cgctcagggg ggccttggtg atctcggtgt    5520
tcactctcag gatgtcgctc agcaggatgg cgtcggacag gttcttggcg gccagaaaca    5580
ggtcggcgta ctggtcgccg atctgggcca gcaggttgtc caggtcgtcg tcgtaggtgt    5640
ccttgctcag ctgcagtttg gcatcctcgg ccaggtcgaa gttgctcttg aagttggggg    5700
```

```
tcaggcccag gctcagggca atcaggtttc cgaacaggcc attcttcttc tcgccgggca   5760
gctgggcgat cagattttcc agccgtctgc tcttgctcag tctggcagac aggatggcct   5820
tggcgtccac gccgctggcg ttgatggggt tttcctcgaa cagctggttg taggtctgca   5880
ccagctggat gaacagcttg tccacgtcgc tgttgtcggg gttcaggtcg ccctcgatca   5940
ggaagtggcc ccggaacttg atcatgtggg ccagggccag atagatcagc cgcaggtcgg   6000
ccttgtcggt gctgtccacc agtttctttc tcaggtggta gatggtgggg tacttctcgt   6060
ggtaggccac ctcgtccacg atgttgccga agatggggtg ccgctcgtgc ttcttatcct   6120
cttccaccag gaaggactct tccagtctgt ggaagaagct gtcgtccacc ttggccatct   6180
cgttgctgaa gatctcttgc agatagcaga tccggttctt ccgtctggtg tatcttcttc   6240
tggcggttct cttcagccgg gtggcctcgg ctgtttcgcc gctgtcgaac agcagggctc   6300
cgatcaggtt cttcttgatg ctgtgccggt cggtgttgcc cagcaccttg aatttcttgc   6360
tgggcacctt gtactcgtcg gtgatcacgg cccagcccac agagttggtg ccgatgtcca   6420
ggccgatgct gtacttcttg tcggctgctg ggactccgtg gataccgacc ttccgcttct   6480
tctttggggc catcttatcg tcatcgtctt tgtaatcaat atcatgatcc ttgtagtctc   6540
cgtcgtggtc cttatagtcc attttttctcg agggatcctg atatatttct attaggtatt   6600
tattattata aaatataaat cttgaatgat aataaataaa atattagtta ttccttttct   6660
agtttaaaat atacatatta taaatatata tatatatata tatattttta ttgtgacaag   6720
aatatataat tataaattat attatttatt tttgtatttt ttttttttt ttttttttt   6780 tcttttttg ttttattttt ctttttttt ataaatatta ttttttttctt ttatcatgca   6840 cattggaata atacattaat atatatatat atattatatt atacatatat tgaataatgt   6900
ttataaaaaa tgcataactt tatgaatat aattttttt aaatatgaca aaagaaaaa   6960 aaaaaaaac caaaaaaat taaaattgaa atgaaatata taaatatatt atttatatat   7020
attatacatt gtttaatact actacatgta tatatatata ttatatatat atatatatat   7080 caatttttc aaaaataaat taatataaa agaggggaaa aaaaaaaaa aaaaaaaaa   7140 aagataatta agtaagcatt taaaaatata taaattgata atatataaaa ttaatcacat   7200
ataaaagctt ataaacacta ggttagctaa ttcgcttgta agaggtactc tcgtttatgc   7260
aaaactattt gatatagcat tttaacaagt acacatatat atatgtaata tatatactat   7320
atatatctat tgcatgtgta ctaagcatgt gcatggcatc ccctttttct cgtgttaaaa   7380
acagtttgta tgataaaata taaggattt gaaaaagaga aaaaatata tgatctcatc   7440 ctatatagcg ccataatttt tatttgggtt gaataaaatt ttctactaaa tttaggtgta   7500
agtaaaataa tggaatatat ataagtacaa taaaaaagtg cataaattaa aaatttta   7560 taataaatat ttttttaaa aaagtcaata ataatattaa atatatataa cacaggatta   7620
tatatgttca ctacaattt ttatattata atataaattc ttttcaattt tcattttatt   7680
ttacatacac tttcctttt tgtcactata ttttaatatt cacatattta gtttaaatac   7740
tggctatttc tttctacatt tgctagtaac aattgtgtag tgcttaaata tatacacaca   7800
cctaaaactt acaagtatc ctaggaccat ggccaagcct ttgtctcaag aagaatccac   7860
cctcattgaa agagcaacgg ctacaatcaa cagcatcccc atctctgaag actacagcgt   7920
cgccagcgca gctctctcta gcgacggccg catcttcact ggtgtcaatg tatatcattt   7980
tactggggga ccttgtgcag aactcgtggt gctgggcact gctgctgctg cggcagctg   8040 caacctgact tgtatcgtcg cgatcggaaa tgagaacagg ggcatcttga gcccctgcgg   8100
```

```
acggtgccga caggtgcttc tcgatctgca tcctgggatc aaagccatag tgaaggacag    8160
tgatggacag ccgacggcag ttgggattcg tgaattgctg ccctctggtt atgtgtggga    8220
gggctaaccg cgggtacccc attaaattta tttaataata gattaaaaat attataaaaa    8280
taaaaacata aacacagaaa ttacaaaaaa aatacatatg aatttttttt ttgtaatctt    8340
ccttataaat atagaataat gaatcatata aacatatca ttattcattt atttacattt    8400
aaaattattg tttcagtatc tttaatttat tatgtatata taaaaataac ttacaatttt    8460
attaataaac aatatatgtt tattaattca tgttttgtaa tttatgggat agcgattttt    8520
tttactgtct gtattttctt ttttaattat gttttaattg tattattttt attttttatta   8580 ttgttctttt tatagtatta ttttaaaaca aaatgtattt tctaagaact tataataata    8640
ataatataaa ttttaataaa aattatattt atcttttaca atatgaacat aaagtacaac    8700
attaatatat agcttttaat attttttattc ctaatcatgt aaatcttaaa ttttttctttt  8760 taaacatatg ttaaatattt atttctcatt atatataaga acatatttat tacatctaga    8820
ggtaccgagc tcgttttcga cactggatgg cggcgttagt atcgaatcga cagcagtata    8880
gcgaccagca ttcacatacg attgacgcat gatattactt tctgcgcact taacttcgca    8940
tctgggcaga tgatgtcgag gcgaaaaaaa atataaatca cgctaacatt tgattaaaat    9000
agaacaacta caatataaaa aaactataca aatgacaagt tcttgaaaac aagaatcttt    9060
ttattgtcag tactgattag aaaaactcat cgagcatcaa atgaaactgc aatttattca    9120
tatcaggatt atcaatacca tattttttgaa aaagccgttt ctgtaatgaa ggagaaaact   9180
caccgaggca gttccatagg atggcaagat cctggtatcg gtctgcgatt ccgactcgtc    9240
caacatcaat acaacctatt aatttcccct cgtcaaaaat aaggttatca agtgagaaat    9300
caccatgagt gacgactgaa tccggtgaga atggcaaaag cttatgcatt tctttccaga    9360
cttgttcaac aggccagcca ttacgctcgt catcaaaatc actcgcatca accaaaccgt    9420
tattcattcg tgattgcgcc tgagcgagac gaaatacgcg atcgctgtta aaaggacaat    9480
tacaaacagg aatcgaatgc aaccggcgca ggaacactgc cagcgcatca acaatatttt   9540
cacctgaatc aggatattct tctaatacct ggaatgctgt tttgccgggg atcgcagtgg    9600
tgagtaacca tgcatcatca ggagtacgga taaaatgctt gatggtcgga agaggcataa    9660
attccgtcag ccagtttagt ctgaccatct catctgtaac atcattggca acgctacctt    9720
tgccatgttt cagaaacaac tctggcgcat cgggcttccc atacaatcga tagattgtcg    9780
cacctgattg cccgacatta tcgcgagccc atttataccc ataaaatca gcatccatgt    9840 tggaatttaa tcgcggcctc gaaacgtgag tcttttcctt acccatggtt gtttatgttc    9900
ggatgtgatg tgagaactgt atcctagcaa gatttttaaaa ggaagtatat gaaagaagaa    9960
cctcagtggc aaatcctaac ctttatatt tctctacagg ggcgcggcgt ggggacaatt    10020
caacgcgtct gtgaggggag cgtttccctg ctcgcaggtc tgcagcgagg agccgtaatt    10080
tttgcttcgc gccgtgcggc catcaaaatg tatggatgca aatgattata catggggatg    10140
tatgggctaa atgtacgggc gacagtcaca tcatgcccct gagctgcgca cgtcaagact    10200
gtcaaggagg gtattctggg cctccatgtc gctggcctaa cattagtaat gtaggtctga    10260
ctttcactca tataagtctt atggtaacta aactaaggtc ttacctttac tgatatatgt    10320
cttactttca ctaacttagg tattacttttt actaacttag gtcttaaatt cagtaactaa    10380
ggtcatactt cgactaacta aggtcttaca ttcactgata taggtcttat gattactaac    10440
```

```
ttaggtccta atttgactaa cataagtcct aacattagta atgtaggtct taacttaact    10500
aacttaggtc ttaccttcac taatataggt cttaatatta ctgacttaag taattaaggt    10560
actaacttag gtcgtaaggt aactaatata taggtcttaa ggtaactaat ttaggtcttg    10620
acttaataaa tataggtcct aacataaata gtataggtcc taatataagt actataggcc    10680
ttaacttaac caacataggt cctaacataa gttatatagg tcttaacgta actaacataa    10740
gtcattaagg tactaagttt ggtcttaatt taacaataac atgtcgctgg cctaacatta    10800
gtaatgtagg tctgactttc actcatataa gtcttatggt aactaaacta aggtcttacc    10860
tttactgata tatgtcttac tttcactaac ttaggtatta cttttactaa cttaggtctt    10920
aaattcagta actaaggtca tacttcgact aactaaggtc ttacattcac tgatataggt    10980
cttatgatta ctaacttagg tcctaatttg actaacataa gtcctaacat tagtaatgta    11040
ggtcttaact taactaactt aggtcttacc ttcactaata taggtcttaa tattactgac    11100
ttaagtaatt aaggtactaa cttaggtcgt aaggtaacta atatataggt cttaaggtaa    11160
ctaatttagg tcttgactta ataaatatag gtcctaacat aaatagtata ggtcctaata    11220
taagtactat aggccttaac ttaaccaaca taggtcctaa cataagttat ataggtctta    11280
acgtaactaa cataagtcat taaggtacta agtttggtct taatttaaca ataaccatgt    11340
cgctggccgg gtggtcttaa tttaacaaat atagaccatg tcgctggccg ggtgacccgg    11400
cggggacgag gcaagctaaa cagatcctcg tgatacgcct atttttatag gttaatgtca    11460
tgataataat ggtttcttag gacggatcgc ttgcctgtaa cttacacgcg cctcgtatct    11520
tttaatgatg gaataatttg ggaatttact ctgtgtttat ttatttttat gttttgtatt    11580
tggattttag aaagtaaata aagaaggtag aagagttacg gaatgaagaa aaaaaaataa    11640
acaaaggttt aaaaaatttc aacaaaaagc gtactttaca tatatattta ttagacaaga    11700
aaagcagatt aaatagatat acattcgatt aacgataagt aaaatgtaaa atcacaggat    11760
tttcgtgtgt ggtcttctac acagacaaga tgaaacaatt cggcattaat acctgagagc    11820
aggaagagca agataaaagg tagtatttgt tggcgatccc cctagagtct tttacatctt    11880
cggaaaacaa aaactatttt ttctttaatt tcttttttta ctttctattt ttaatttata    11940
tatttatatt aaaaaatttta aattataatt atttttatag cacgtgatga aaaggaccca    12000
ggtggcactt ttcggggaaa tctcgacctg cagcgtacga agct                     12044
```